US010612018B2

(12) United States Patent
Seitz et al.

(10) Patent No.: US 10,612,018 B2
(45) Date of Patent: Apr. 7, 2020

(54) NUCLEIC ACID TRANSCRIPTION METHOD

(71) Applicant: LEXOGEN GMBH, Vienna (AT)

(72) Inventors: Alexander Seitz, Vienna (AT); Pamela Moll, Vienna (AT); Magdalena Anna Napora, Vienna (AT)

(73) Assignee: LEXOGEN GMBH, Vienna (AT)

(*) Notice: Subject to any disclaimer, the term of this patent is extended or adjusted under 35 U.S.C. 154(b) by 118 days.

(21) Appl. No.: 14/241,311

(22) PCT Filed: Sep. 17, 2012

(86) PCT No.: PCT/EP2012/068250
§ 371 (c)(1),
(2) Date: Feb. 26, 2014

(87) PCT Pub. No.: WO2013/038010
PCT Pub. Date: Mar. 21, 2013

(65) Prior Publication Data
US 2015/0152409 A1    Jun. 4, 2015

(30) Foreign Application Priority Data

Sep. 16, 2011  (EP) .................................. 11181546
Jul. 24, 2012  (EP) .................................. 12177647

(51) Int. Cl.
*C12N 15/10*   (2006.01)
*C12Q 1/6853*  (2018.01)
*C12Q 1/6816*  (2018.01)

(52) U.S. Cl.
CPC ....... *C12N 15/1096* (2013.01); *C12Q 1/6816* (2013.01); *C12Q 1/6853* (2013.01)

(58) Field of Classification Search
None
See application file for complete search history.

(56) References Cited

U.S. PATENT DOCUMENTS 5,876,932 A   3/1999  Fischer
6,261,770 B1  7/2001  Warthoe
(Continued)

FOREIGN PATENT DOCUMENTS

EP         233104     8/1987
WO      9313216 A1    7/1993
(Continued)

OTHER PUBLICATIONS

Latorra et al., "Enhanced Allele-Specific PCR Discrimination in SNP Genotyping Using 3' Locked Nucleic Acid (LNA) Primers," Human Mutations, 2003, vol. 22, pp. 79-85.*
(Continued)

*Primary Examiner* — Samuel C Woolwine
(74) *Attorney, Agent, or Firm* — Wagenknecht IP Law Group PC

(57) ABSTRACT

The present invention relates to methods for generating an amplified nucleic acid portion of a template nucleic acid, comprising obtaining said template nucleic acid, annealing at least one oligonucleotide primer to said template nucleic acid, annealing at least one oligonucleotide stopper to said template nucleic acid, elongating the at least one oligonucleotide primer in a template specific manner until the elongating product nucleic acid reaches the position of an annealed oligonucleotide stopper, whereby the elongation reaction is stopped, wherein in said elongation reaction said oligonucleotide stopper is not elongated, and wherein the elongated product nucleic acid is ligated to the 3' end of said oligonucleotide stopper—said stopper may also be a primer itself and uses and kits for performing said method.

32 Claims, 16 Drawing Sheets

Specification includes a Sequence Listing.

(56) References Cited

U.S. PATENT DOCUMENTS

| | | | |
|---|---|---|---|
| 9,334,532 B2 | 5/2016 | Seitz et al. | |
| 2003/0108913 A1* | 6/2003 | Schouten | C12Q 1/686 |
| | | | 435/6.18 |
| 2004/0009512 A1 | 1/2004 | Ares et al. | |
| 2005/0100911 A1 | 5/2005 | Patil et al. | |
| 2009/0203531 A1* | 8/2009 | Kurn | C12Q 1/686 |
| | | | 506/6 |
| 2010/0009355 A1* | 1/2010 | Kolodney | C12Q 1/6858 |
| | | | 435/6.18 |
| 2010/0035303 A1* | 2/2010 | Rhee | C12Q 1/6844 |
| | | | 435/91.2 |
| 2012/0238457 A1 | 9/2012 | Seitz et al. | |
| 2017/0321248 A1 | 11/2017 | Paul et al. | |
| 2017/0342409 A1 | 11/2017 | Seitz et al. | |

FOREIGN PATENT DOCUMENTS

| | | |
|---|---|---|
| WO | 9417210 A1 | 8/1994 |
| WO | 9802449 A1 | 1/1998 |
| WO | 1999/055913 | 11/1999 |
| WO | 2006/137734 | 12/2006 |
| WO | 2007/073171 | 6/2007 |
| WO | 2008/093098 | 8/2008 |
| WO | 2009/073629 | 6/2009 |
| WO | 2009/116863 | 9/2009 |
| WO | 2016/005524 | 1/2016 |

OTHER PUBLICATIONS

Johnson et al., "A third pair for the polymerase chain reaction: inserting isoC and isoG," Nucleic Acids Research, 2004, vol. 32, No. 6, pp. 1937-1941.*
Park et al., "Detection of Hepatitis C Virus RNA using Ligation-Dependent Polymerase Chain Reaction in Formalin-Fixed, Paraffin-Embedded Liver Tissues," American Journal of Pathology, Nov. 1996, vol. 149, No. 5, pp. 1485-1491.*
European Search Report for 11181546.0, dated May 2012
Written Opinion IPEA for International Application No. PCT/EP2012/068250, dated May 2013.
Seyfang A et al: "Multiple site-directed mutagenesis of more than 10 sites simultaneously and in a single round," in Analytical Biochemistry, Academic Press Inc. New York. vol. 324 No. 2; Jan. 15, 2004 pp. 285-291.
Hogrefe H H et al: "Creating Randomized Amino Acid Libraries with the Quikchange Multi Site-Directed Mutagenesis Kit," Biotechniques, Informa Healthcare, US. vol. 33, No. 5; Nov. 1, 2002 pp. 1158-1160+1162.
H. Li et al: "Determination of tag density required for digital transcriptome analysis: Application to an androgen-sensitive prostate cancer model," PNAS, vol. 105, No. 51 , Dec. 23, 2008 pp. 20179-20184.
Valerio Costa et al: "Uncovering the Complexity of Transcriptomes with RNA-Seq", Journal of Biomedicine and Biotechnology, vol. 7, No. 7, Art. 1 12, Jan. 1, 2010 pp. 1299-1320.
Margulies et al. "Genome sequencing in microfabricated high-density picolitre reactors," Nature, 2005, 437 (15):376-380.
Kuhn et al. "Poly(A) Tail Length is Controlled by the Nuclear Poly(A)-binding Protein Regulating the Interaction between Poly(A) Polymerase and the Cleavage and Polyadenylation Specificity Factor," Journal of Biological Chemistry, 2009, 284(34):22803-22814.
EP10788340.7 European Communication pursuant to Article 94(3) EPC datd Jun. 6, 2014.
Surinder et al. "Myeloma V-L and V-H gene sequences reveal a complementary imprint of antigen selection in tumor cells," Blood, 1997, 89(1):219-226.
EP10788340.7 European Communication pursuant to Article 94(3) EPC dated Jul. 29, 2013.
Pansri et al. "A compact phage display human scFv library for selection of antibodies to a wide variety of antigens," BMC Biotechnology, 2009, 9:6.
Yeakley et al. "Profiling alternative splicing on fiber-optic arrays," Nature Biotechnology, Apr. 2002, 20(4):353-358.
Abe et al. "Rapid DNA Chemical Ligation for Amplification of RNA and DNA Signal," Bioconjugate Chemistry, Jan. 2008, 19(1):327-333.
Nilsson et al. "RNA-templated DNA ligation for transcript analysis," Nucleic Acids Research, Jan. 2001, 29 (2):578-581.
Cao et al. "Recent developments in ligase-mediated amplification and detection," Trends in Biotechnology, Jan. 2004, 22(1):38-44.
EP17184341.0 Extended European Search Report dated Nov. 14, 2017.
Chen et al. "Mapping translocation breakpoints by next-generation sequencing," Genome Res., 2008, 18:1143-1149.
Fredriksson et al. "Multiplex amplification of all coding sequences within 10 cancer genes by Gene-Collector," Nucleic Acids Research, 2007, 35(7):e47.
Armour et al. "Digital transcriptome profiling using selective hexamer priming for cDNA synthesis," Nature Methods, 2009, 6(9):647-650.
Breyne et al. "Quantitative cDNA-AFLP analysis for genome-wide expression studies," Mol. Gen. Genomics, 2003, 269:173-179.
Liang et al. "Differential display of eukaryotic messenger RNA by means of the polymerase chain reaction," Science, 1992, 257:967-971.
Maruyama et al. "Oligo-capping: a simple method to replace the cap structure of eukaryotic mRNAs with oligoribonucleotides," Gene, 1994, 138:171-174.
Matz et al. "Ordered differential display: a simple method for systematic comparison of gene expression profiles," Nucleic Acids Research, 1997, 25(12):2541-2542.
Nagalakshmi et al. "The transcriptional landscape of the yeast genome defined by RNA sequencing," Science, 2008, 320:1344-1349.
Shiraki et al. "Cap analysis gene expression for high-throughput analysis of transcriptional starting point and identification of promoter usage," PNAS, 2003, 100(26):15776-15781.
Wilhelm et al. "RNA-seq-quantitative measurement of expression through massively parallel RNA-sequencing," Methods, 2009, 48:249-257.
Aird et al. "Quantitative high-throughput profiling of snake venom gland transcriptomes and proteomes (Ovaphis okinavensis and Protobothrops flavorviridis)," BMC Genomics, 2013, 14:790.
Baker et al. "The External RNA Controls Consortium: a progress report," Nature Methods, Oct. 2005, 2 (10):731-734.
Benson et al. "Genbank," Nucleic Acid Research, 2013, 41:D36-42.
Blomquist et al. "Targeted RNA-Sequencing with Competitive Multiplex-PCR Amplicon Libraries," Plos One, 2013, 8(11):e79120.
Brennecke et al. "Accounting for technical noise in single-cell RNA-seq experiments," Nature Methods, Nov. 2013, 10(11):1093-1098.
Bullard et al. "Evaluation of statistical methods for normalization and differential expression in mRNA-Seq experiments," BMC Bioinformatics, 2010, 11:94-107.
Cronin et al. "Universal RNA Reference Materials for Gene Expression," Clinical Chemistry, 2004, 50(8):1464-1471.
Devonshire et al. "Evaluation of external RNA controls for the standardisation of gene expression biomarker measurements," BNC Genomics, 2010, 11:662.
Hu et al. "PennSeq: accurate isoform-specific gene expression quanitification in RNA-Seq by modeling non-uniform read distribution," Nucleic Acids Research, 2014, 42(3):e20.
Jiang et al. "Synthetic spike-in standards for RNA-seq experiments," Genome Res., 2011, 21:1543-1551.
Karlin et al. "Methods for assessing the statistical significance of molecular sequence features by using general scoring schemes," Proc. Natl. Acad. Sci., Mar. 1990, 87:2264-2268.
Koscielny et al. "ASTD: The Alternative Splicing and Transcript Diversity database," Genomics, 2009, 93:213-220.
Lin et al. "Transcriptional Amplification in Tumor Cells with Elevated c-Myc," Cell, Sep. 28, 2012, 151(1):56-67.
Loven et al. "Revisiting Global Gene Expression Analysis," Cell, Oct. 26, 2012, 151(3):476-482.
Nilsen et al. "Expansion of the eukaryotic proteome by alternative splicing," Nature, Jan. 28, 2010, 463:457-463.

(56) References Cited

OTHER PUBLICATIONS

Rapaport et al. "Comprehensive evaluation of differential gene expression analysis methods for RNA-seq data," Genome Biology, 2013, 14:R95.
Reid et al. "Proposed methods for testing and selecting the ERCC external RNA controls," BMC Genomics, 2005, 6:150.
Rice et al. "Emboss: The European Molecular Biology Open Software Suite," TIG, Jun. 2000, 16(6):276-277.
Roberts et al. "Improving RNA-Seq expression estimates by correcting for fragment bias," Genome Biology, 2011, 12:R22.
Sanna et al. "Overlapping genes in the human and mouse genomes," BMC Genomics, 2008, 9:169.
Shi et al. "The MicroArray Quality Control (MAQC) project shows inter- and intraplatform reproducibility of gene expression measurements," Nature Biotechnology, Sep. 2006, 24(9):1151-1161.
Shippy et al. "Using RNA sample titrations to assess microarray platform performance and normalization techniques," Nat. Biotechnol., Sep. 2006, 24(9):1123-1131.
Sun et al. "Simultaneous quantification of alternatively spliced transcripts in a single droplet digital PCR reaction," BioTechniques, Jun. 2014, 56:319-325.
Trapnell et al. "Transcript assembly and quantification by RNA-Seq reveals unannotated transcripts and isoform switching during cell differentiation," Nature Biotechnology, May 2010, 28(5):511-518.
Wang et al. "Alternative isoform regulation in human tissue transcriptomes," Nature, Nov. 27, 2008, 456:470-476.
Wang et al. "RNA-Seq: a revolutionary tool for transcriptomics," Nat. Rev. Genet. Jan. 2009, 10(1):57-63.
Xin et al. "Alternative Promoters Influence Alternative Splicing at the Genomic Level," Plos One, 2008, 3(6):e2377.
Yoon et al. "Genetics and Regulatory Impact of Alternative Polyadenylation in Human B-Lymphoblastoid Cells," Plus Genet., Aug. 2012, 8(8):e1002882.
Zhang et al. "SASD: the Synthetic Alternative Splicing Database for identifying novel isoform from proteomics," BMC Bioinformatics, 2013, 14(Suppl 14):S13.
EP14176417.5 Extended European Search Report dated Apr. 2, 2015.
PCT/EP2015/065756 International Search Report and Written Opinion dated Aug. 25, 2015.
Prashar et al. "Analysis of differential gene expression by display of 3' end restriction fragments of cDNA," PNAS, 1996, 93:659-663.
Meyer et al. "Targeted high-throughput sequencing of tagged nucleic acid samples," Nucleic Acids Research, 2007, 35(15):e97.
Parkhomchuk et al. "Transcriptome analysis by strand-specific sequencing of complementary DNA," Nucleic Acids Research, 2009, 37(18):e123.
Craig et al. "Identification of genetic variants using bar-coded multiplexed sequencing," Nature Methods, 2008, 5 (10):887-893.
KR10-2014-7010187 Korean Office Action dated Dec. 13, 2018.

\* cited by examiner

SEQUENCE LISTING

```
<160> NUMBER OF SEQ ID NOS: 38

<210> SEQ ID NO 1
<211> LENGTH: 36
<212> TYPE: DNA
<213> ORGANISM: Artificial
<220> FEATURE:
<223> OTHER INFORMATION: primer oligonucleotide

<400> SEQUENCE: 1
gctaatacga ctcactatag ttgtcaccag catccc                               36

<210> SEQ ID NO 2
<211> LENGTH: 43
<212> TYPE: DNA
<213> ORGANISM: Artificial
<220> FEATURE:
<223> OTHER INFORMATION: primer oligonucleotide

<400> SEQUENCE: 2
tttttttttt tttttttttt tttttttcga atgggccgca gga                      43

<210> SEQ ID NO 3
<211> LENGTH: 130
<212> TYPE: DNA
<213> ORGANISM: Artificial
<220> FEATURE:
<223> OTHER INFORMATION: PCR product

<400> SEQUENCE: 3
gctaatacga ctcactatag ttgtcaccag catccctaga cccgtacagt gcccactccc    60
cttcccagtt tccgactgtc cccggcctcc tgcggcccat tcgaaaaaaa aaaaaaaaaa   120
aaaaaaaaaa                                                          130

<210> SEQ ID NO 4
<211> LENGTH: 111
<212> TYPE: RNA
<213> ORGANISM: Artificial
<220> FEATURE:
<223> OTHER INFORMATION: PCR product

<400> SEQUENCE: 4
guugucacca gcaucccuag acccguacag ugcccacucc ccuucccagu uuccgacugu    60
ccccggccuc cugcggccca uucgaaaaaa aaaaaaaaaa aaaaaaaaa a             111
```

```
<210> SEQ ID NO 5
<211> LENGTH: 12
<212> TYPE: DNA
<213> ORGANISM: Artificial
<220> FEATURE:
<223> OTHER INFORMATION: stopper oligonucleotide
<220> FEATURE:
<221> NAME/KEY: misc_feature
<222> LOCATION: (1)..(1)
<223> OTHER INFORMATION: LNA

<400> SEQUENCE: 5
gggcactgta cg                                              12

<210> SEQ ID NO 6
<211> LENGTH: 12
<212> TYPE: DNA
<213> ORGANISM: Artificial
<220> FEATURE:
<223> OTHER INFORMATION: stopper oligonucleotide

<400> SEQUENCE: 6
gggcactgta cg                                              12

<210> SEQ ID NO 7
<211> LENGTH: 11
<212> TYPE: DNA
<213> ORGANISM: Artificial
<220> FEATURE:
<223> OTHER INFORMATION: stopper oligonucleotide
<220> FEATURE:
<221> NAME/KEY: misc_feature
<222> LOCATION: (1)..(2)
<223> OTHER INFORMATION: phosphorothioate backbone
<220> FEATURE:
<221> NAME/KEY: misc_feature
<222> LOCATION: (10)..(11)
<223> OTHER INFORMATION: phosphorothioate backbone

<400> SEQUENCE: 7
gggcactgta c                                               11

<210> SEQ ID NO 8
<211> LENGTH: 11
<212> TYPE: DNA
<213> ORGANISM: Artificial
<220> FEATURE:
<223> OTHER INFORMATION: stopper oligonucleotide
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (10)..(11)
<223> OTHER INFORMATION: phosphorothioate backbone

<400> SEQUENCE: 8
gggcactgta c                                               11

<210> SEQ ID NO 9
<211> LENGTH: 55
<212> TYPE: DNA
<213> ORGANISM: Artificial
<220> FEATURE:
<223> OTHER INFORMATION: primer oligonucleotide

<400> SEQUENCE: 9
acggagccta tctatatgtt cttgacattt tttttttttt tttttttttt ttttv    55
```

<210> SEQ ID NO 10
<211> LENGTH: 35
<212> TYPE: DNA
<213> ORGANISM: Artificial
<220> FEATURE:
<223> OTHER INFORMATION: PCR product

<400> SEQUENCE: 10
gggcactgta cgggtctagg gatgctggtg acaac                              35

<210> SEQ ID NO 11
<211> LENGTH: 103
<212> TYPE: DNA
<213> ORGANISM: Artificial
<220> FEATURE:
<223> OTHER INFORMATION: PCR product

<400> SEQUENCE: 11
acggagccta tctatatgtt cttgacattt tttttttttt tttttttttt ttttcgaatg    60
ggccgcagga ggccggggac agtcggaaac tgggaagggg agt                    103

<210> SEQ ID NO 12
<211> LENGTH: 138
<212> TYPE: DNA
<213> ORGANISM: Artificial
<220> FEATURE:
<223> OTHER INFORMATION: PCR product

<400> SEQUENCE: 12
acggagccta tctatatgtt cttgacattt tttttttttt tttttttttt ttttcgaatg    60
ggccgcagga ggccggggac agtcggaaac tgggaagggg agtgggcact gtacgggtct   120
agggatgctg gtgacaac                                                138

<210> SEQ ID NO 13
<211> LENGTH: 6
<212> TYPE: DNA
<213> ORGANISM: Artificial
<220> FEATURE:
<223> OTHER INFORMATION: random hexamer oligonucleotide
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (4)..(6)
<223> OTHER INFORMATION: n is a, c, g, or t

<400> SEQUENCE: 13 nnnnnn                                                               6

<210> SEQ ID NO 14
<211> LENGTH: 6
<212> TYPE: DNA
<213> ORGANISM: Artificial
<220> FEATURE:
<223> OTHER INFORMATION: random hexamer oligonucleotide
<220> FEATURE:
<221> NAME/KEY: misc_feature
<222> LOCATION: (1)..(6)
<223> OTHER INFORMATION: n is a, c, g, or t

<400> SEQUENCE: 14 nnnnnn                                                               6

```
<210> SEQ ID NO 15
<211> LENGTH: 12
<212> TYPE: DNA
<213> ORGANISM: Artificial
<220> FEATURE:
<223> OTHER INFORMATION: primer oligonucleotide
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (7)..(12)
<223> OTHER INFORMATION: n is a, c, g, or t

<400> SEQUENCE: 15
ggghhhnnnn nn                                                      12

<210> SEQ ID NO 16
<211> LENGTH: 12
<212> TYPE: DNA
<213> ORGANISM: Artificial
<220> FEATURE:
<223> OTHER INFORMATION: primer oligonucleotide
<220> FEATURE:
<221> NAME/KEY: misc_feature
<222> LOCATION: (7)..(12)
<223> OTHER INFORMATION: n is a, c, g, or t

<400> SEQUENCE: 16
ggghhhnnnn nn                                                      12

<210> SEQ ID NO 17
<211> LENGTH: 23
<212> TYPE: DNA
<213> ORGANISM: Artificial
<220> FEATURE:
<223> OTHER INFORMATION: primer oligonucleotide

<400> SEQUENCE: 17
ggcgtttttt tttttttttt ttv                                          23

<210> SEQ ID NO 18
<211> LENGTH: 21
<212> TYPE: DNA
<213> ORGANISM: Artificial
<220> FEATURE:
<223> OTHER INFORMATION: primer oligonucleotide

<400> SEQUENCE: 18
ctggatgaat ggcttgagtg t                                            21

<210> SEQ ID NO 19
<211> LENGTH: 21
<212> TYPE: DNA
<213> ORGANISM: Artificial
<220> FEATURE:
<223> OTHER INFORMATION: primer oligonucleotide

<400> SEQUENCE: 19
gcaactccac gctcatagaa g                                            21

<210> SEQ ID NO 20
<211> LENGTH: 25
<212> TYPE: DNA
<213> ORGANISM: Artificial
<220> FEATURE:
<223> OTHER INFORMATION: primer oligonucleotide
```

<400> SEQUENCE: 20
ccttccagga ggagttcatg ccagt    25

<210> SEQ ID NO 21
<211> LENGTH: 26
<212> TYPE: DNA
<213> ORGANISM: Artificial
<220> FEATURE:
<223> OTHER INFORMATION: primer oligonucleotide

<400> SEQUENCE: 21
cacacggaga gatgaatgag gggaga    26

<210> SEQ ID NO 22
<211> LENGTH: 23
<212> TYPE: DNA
<213> ORGANISM: Artificial
<220> FEATURE:
<223> OTHER INFORMATION: primer oligonucleotide

<400> SEQUENCE: 22
gccttcatgg ctgtgtgcat tga    23

<210> SEQ ID NO 23
<211> LENGTH: 27
<212> TYPE: DNA
<213> ORGANISM: Artificial
<220> FEATURE:
<223> OTHER INFORMATION: primer oligonucleotide

<400> SEQUENCE: 23
catcctgccc tgtagaaagt cctcttg    27

<210> SEQ ID NO 24
<211> LENGTH: 25
<212> TYPE: DNA
<213> ORGANISM: Artificial
<220> FEATURE:
<223> OTHER INFORMATION: primer oligonucleotide

<400> SEQUENCE: 24
ccagtgtcac aagtgcaggt ccatc    25

<210> SEQ ID NO 25
<211> LENGTH: 26
<212> TYPE: DNA
<213> ORGANISM: Artificial
<220> FEATURE:
<223> OTHER INFORMATION: primer oligonucleotide

<400> SEQUENCE: 25
gcggtcagct ttgtccagaa gtgtgt    26

<210> SEQ ID NO 26
<211> LENGTH: 25
<212> TYPE: DNA
<213> ORGANISM: Artificial
<220> FEATURE:
<223> OTHER INFORMATION: primer oligonucleotide

<400> SEQUENCE: 26
gtaagatggt ggatggggtg ggtgt    25

```
<210> SEQ ID NO 27
<211> LENGTH: 25
<212> TYPE: DNA
<213> ORGANISM: Artificial
<220> FEATURE:
<223> OTHER INFORMATION: primer oligonucleotide

<400> SEQUENCE: 27
tcgctctgaa atgctgactc cttca                                              25

<210> SEQ ID NO 28
<211> LENGTH: 25
<212> TYPE: DNA
<213> ORGANISM: Artificial
<220> FEATURE:
<223> OTHER INFORMATION: primer oligonucleotide

<400> SEQUENCE: 28
acccaggttc tactgcgtcc tgtcc                                              25

<210> SEQ ID NO 29
<211> LENGTH: 25
<212> TYPE: DNA
<213> ORGANISM: Artificial
<220> FEATURE:
<223> OTHER INFORMATION: primer oligonucleotide

<400> SEQUENCE: 29
cctccagggc tgtcacgttc ttctt                                              25

<210> SEQ ID NO 30
<211> LENGTH: 27
<212> TYPE: DNA
<213> ORGANISM: Artificial
<220> FEATURE:
<223> OTHER INFORMATION: primer oligonucleotide

<400> SEQUENCE: 30
tttttttttt tttttttttt ttttttt                                            27

<210> SEQ ID NO 31
<211> LENGTH: 36
<212> TYPE: DNA
<213> ORGANISM: Artificial
<220> FEATURE:
<223> OTHER INFORMATION: primer oligonucleotide
<220> FEATURE:
<221> NAME/KEY: misc_feature
<222> LOCATION: (34)..(36)
<223> OTHER INFORMATION: n is a, c, g, or t

<400> SEQUENCE: 31
tccctacacg acgctcttcc gatctgactg gggnnn                                  36

<210> SEQ ID NO 32
<211> LENGTH: 30
<212> TYPE: DNA
<213> ORGANISM: Artificial
<220> FEATURE:
<223> OTHER INFORMATION: primer oligonucleotide

<400> SEQUENCE: 32
cagtcagatc ggaagagcgt cgtgtaggga                                         30
```

```
<210> SEQ ID NO 33
<211> LENGTH: 34
<212> TYPE: DNA
<213> ORGANISM: Artificial
<220> FEATURE:
<223> OTHER INFORMATION: stopper oligonucleotide
<220> FEATURE:
<221> NAME/KEY: misc_feature
<222> LOCATION: (6)..(9)
<223> OTHER INFORMATION: n is a, c, g, or t

<400> SEQUENCE: 33
ggghhnnnna gatcggaaga gcggttcagc agga                               34

<210> SEQ ID NO 34
<211> LENGTH: 25
<212> TYPE: DNA
<213> ORGANISM: Artificial
<220> FEATURE:
<223> OTHER INFORMATION: stopper oligonucleotide

<400> SEQUENCE: 34
tcctgctgaa ccgctcttcc gatct                                        25

<210> SEQ ID NO 35
<211> LENGTH: 58
<212> TYPE: DNA
<213> ORGANISM: Artificial
<220> FEATURE:
<223> OTHER INFORMATION: primer oligonucleotide

<400> SEQUENCE: 35
aatgatacgg cgaccaccga gatctacact ctttccctac acgacgctct tccgatct    58

<210> SEQ ID NO 36
<211> LENGTH: 61
<212> TYPE: DNA
<213> ORGANISM: Artificial
<220> FEATURE:
<223> OTHER INFORMATION: primer oligonucleotide

<400> SEQUENCE: 36
caagcagaag acggcatacg agatcggtct cggcattcct gctgaaccgc tcttccgatc  60
t                                                                  61

<210> SEQ ID NO 37
<211> LENGTH: 34
<212> TYPE: DNA
<213> ORGANISM: Artificial
<220> FEATURE:
<223> OTHER INFORMATION: primer oligonucleotide
<220> FEATURE:
<221> NAME/KEY: misc_feature
<222> LOCATION: (29)..(34)
<223> OTHER INFORMATION: n is a, c, g, or t

<400> SEQUENCE: 37
tccctacacg acgctcttcc gatctagcnn nnnn                              34

<210> SEQ ID NO 38
<211> LENGTH: 34
<212> TYPE: DNA
<213> ORGANISM: Artificial
<220> FEATURE:
<223> OTHER INFORMATION: oligonucleotide stopper
```

```
<220> FEATURE:
<221> NAME/KEY: misc_feature
<222> LOCATION: (1)..(9)
<223> OTHER INFORMATION: n is a, c, g, or t

<400> SEQUENCE: 38
nnnnnnnnna gatcggaaga gcggttcagc agga                                  34
```

NUCLEIC ACID TRANSCRIPTION METHOD

CROSS REFERENCE TO RELATED APPLICATIONS

This is a national phase patent application under 35 U.S.C. § 371 of international patent application serial no. PCT/EP2012/068250, filed Sep. 17, 2012, which claims priority to European patent application serial no. 11181546.0, filed Sep. 16, 2011 and European patent application serial no. 12177647.0 filed Jul. 24, 2012; the contents of each are herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with file "LEXA03U1_SEQListing_ST25" created on 26 Feb. 2014 and having a size of 9 Kilobytes. The sequence listing contained in this ASCII formatted document forms part of the specification and is herein incorporated by reference in its entirety.

FIELD OF INVENTION

The present invention relates to the field of amplifying or analyzing samples of nucleic acids by amplification of defined sequence portions.

BACKGROUND

Numerous amplification-based methods for the amplification and detection of target nucleic acids are well known and established in the art. The polymerase chain reaction, commonly referred to as PCR, uses multiple cycles of denaturation, annealing of primer pairs to opposite strands, and primer extension to exponentially increase copy numbers of the target sequence (U.S. Pat. Nos. 4,683,195; 4,683,202; 4,800,159; 5,804,375). In a variation called RT-PCR, reverse transcriptase (RT) is used to make a complementary DNA (cDNA) from RNA, and the cDNA is then amplified by PCR to produce multiple copies of DNA (U.S. Pat. Nos. 5,322,770; 5,310,652).

PCR reactions generally comprise carrying out multiple cycles of:
(A) hybridizing (annealing) a first primer to a site in a nucleic acid strand at one end of the target nucleic acid sequence, and hybridizing a second primer to a site corresponding to the opposite end of the target sequence in the complementary nucleic acid strand;
(B) synthesizing (extending) a nucleic acid sequence from each respective primer; and
(C) denaturing the double stranded nucleic acid produced in step (B) so as to form single stranded nucleic acid.
Denaturation is generally carried out at from 80 to 100° C., hybridization (annealing) is generally carried out at from 40 to 80° C., and extension is generally carried out at from 50 to 80° C. A typical cycle is denaturation: about 94° C. for about 1 min, hybridization: about 58° C. for about 2 min, and extension: about 72° C. for about 1 min. The exact protocol depends on factors such as the length and sequence of the primers and target sequence, and the enzyme used.

PCR has been adopted for various applications. E.g., GB 2293238 describes methods to reduce non-specific priming and amplifying nucleic acid sequences. Blocking "primers" (or oligonucleotides) are disclosed that produce misalignment and reduce non-specific priming by creating competitive primer annealing reactions to the amplification primers. For example, mixtures of random blocking primers are used that comprise a ddNTP at the 3' position to prevent initiation of extension reactions. Only correct amplification primers displace their blocking primers and can initiate the amplification reaction.

Methods have been established for using blocking primers that specifically bind to unwanted target oligonucleotide molecules in a sample to prevent amplification thereof in a PCR reaction of unblocked oligonucleotide molecules. Unblocked oligonucleotides can be amplified without further measures to ensure target specificity—in the absence of amplifiable competitive oligonucleotide molecules that are not intended for amplification (US 2002/0076767 A1 and U.S. Pat. No. 6,391,592 B1; WO 99/61661).

A similar method is disclosed in the WO 02/086155, wherein blocking oligonucleotides bound to an undesired template result in premature termination of an elongation reaction. The blocking oligonucleotides bind specifically to one template in a mixture while leaving other templates free for amplification.

U.S. Pat. No. 5,849,497 describes the use of blocking oligonucleotides during a PCR method with a DNA polymerase lacking 5' exonuclease activity. This DNA polymerase cannot digest the blocking oligonucleotides that prevent amplification. Such a system has been selected to avoid using PNA (peptide nucleic acids) as blocking oligonucleotides. A similar system is described in WO 2009/019008 that however contemplates the use of PNA and LNA, among others, as blocking oligonucleotides.

All these methods have in common that amplification of unwanted templates is specifically suppressed by hybridization of a specific blocking oligonucleotide.

In patent application WO 98/02449 A1 (U.S. Pat. No. 6,090,552) a "triamplification" DNA amplification method is described. It is based on the use of a hairpin primer that is extended and ligated to a blocker. Both primer and blocker bind to one template DNA strand. The second primer binds to the complementary DNA strand. The blocker and one primer are partially complementary with the primer containing a donor and the blocker containing an acceptor moiety for FRET (Fluorescence Resonance Energy Transfer). An extension of the primer and a ligation of an extension product to the blocker leads to a decrease in fluorescence, because they are no longer in close proximity in a blocker primer hybrid. This triamplification method is limited to the use of template DNA and does not relate to RNA methods.

WO 94/17210 A1 relates to a PCT method using multiple primers for both anti-sense and sense strand of a target DNA.

Seyfang et al. [1] describe the use of multiple phosphorylated oligonucleotides in order to introduce mutations into a DNA strand. T4 DNA polymerase, which lacks any detectable strand displacement activity or 5'-3' exonuclease activity, is used, which is unsuitable for RNA templates.

Hogrefe et al. [2] describe the generation of randomized amino acid libraries with the QuikChange Multi Site-Deirected Mutagenisis Kit. Specific primers containing 3 degenerate nucleotides in the center complementary to a known single stranded target DNA are used. The described kit uses PfuTurbo DNA polymerase which is unsuitable for RNA templates.

The analysis of RNA regularly starts with reverse transcribing RNA into cDNA as DNA is more stable than RNA and many methods exist for analyzing DNA. Whatever protocol is used to analyze the cDNA, it is important that the cDNA generated during reverse transcription (RT) represents the RNA that needs to be analyzed in sequence and concentration as closely as possible.

Reverse transcription is generally carried out using reverse transcriptases. These enzymes require an oligonucleotide primer that hybridizes to the RNA to start (prime) the template dependent polymerization of the cDNA. The two most common priming strategies used are oligo dT priming and random priming.

Oligo dT priming is used for RT of mRNAs that have a poly A tail on their 3' end. The oligo dT primes the RNA at the 3' end and the reverse transcriptase copies the mRNA up to its 5' end. One drawback of this approach is that high quality mRNA is needed as any mRNA degradation will lead to a strong overrepresentation of the 3' ends of mRNAs.

Even if un-degraded mRNA is used the cDNA molecules may still be truncated due to premature polymerization stop events. A frequent cause is secondary and tertiary structure formation in highly structured RNA regions. Especially when the GC content is high the reverse transcriptase might not read through these regions and thus the cDNA becomes truncated. The likelihood of such events to occur increases the longer the mRNA is that needs to be copied. Therefore oligo dT primed cDNA can show a strong bias towards over-representing the 3' ends of RNAs. Thus, 3' end priming suffers from a concentration bias that leads to an increase of sequences at or near the 3' end with gradually reduced representation of sequences in the direction of the 5' end (see FIG. 15, triangles, for qPCR measurement of the bias). This is problematic in quantitative approaches, e.g. in the determination of the degree of expression of a particular gene, in difference analysis or in complete expression profiling of a cell.

Approaches have been developed to overcome RNA secondary structure termination especially when long mRNAs need to be reverse transcribed into full length cDNAs. One such method for instance involves a mixture of 2 reverse transcriptases, one highly processive such as MMLV or AMV and mutants thereof, first incubating the reaction mixture at a normal temperature range to allow first strand synthesis plus using a thermostable enzyme composition having reverse transcriptase activity and then incubating the reaction mixture at a temperature that inhibits the presence of secondary mRNA structures to generate a first strand (U.S. Pat. No. 6,406,891). However, buffers for reverse transcriptases contain high concentrations of $MgCl_2$ (3-10 mM) or $Mn^{2+}$ (e.g for Tth DNA polymerase) and RNA is highly ²unstable and susceptible to breaks and/or degradation at higher temperatures especially in the presence of these divalent cations. The cycling method between two temperatures to bypass secondary structures might also lead to random priming by short RNA fragments that were generated during high temperatures. Such short RNA fragments will be used by MMLV-H or other viral reverse transcriptases as a primer [3]. Again this would lead to a bias in the synthesized cDNA.

Another approach is random priming that has the advantage of hybridizing at multiple locations along the RNA and hence also blocking those sequences from taking part in secondary structure formation. In random priming an oligonucleotide population of random sequence, usually a random hexamer is used to prime the RT anywhere within the template nucleic acid strand. Random priming is used for both, reverse transcription or regular transcription using DNA as template. When product DNA was analyzed it was found that random priming does not result in equal efficiencies of reverse transcription for all targets in the sample [4, 5]. Furthermore there is no linear correlation between the amount of template nucleic acid input and product DNA output when specific targets are measured [4, 5]. Indeed, it has been shown that the use of random primers can lead to overestimate some template copy numbers by up to 19-fold compared to sequence-specific primed templates [6]. Although a lot was speculated about the underlying causes for these phenomena, no conclusive rational has been put forward.

OBJECTIVE

The present inventors have observed that there is a general bias in such randomly primed cDNA libraries, in the form that the sequence parts on the 5' ends of RNA molecules are overrepresented when compared to the parts on 3' ends. The reason for this phenomenon is to be found in the combination of random priming and the strong strand displacement activity of the reverse transcriptases. As RNA has a high degree of secondary structure, reverse transcriptases had to evolve a strong strand displacement activity to overcome this secondary structure and to effectively generate cDNA. Given the strong strand displacement activity of reverse transcriptase the 5' side of any RNA will be represented several times in a cDNA library when random oligonucleotides are used for priming. A similar effect happens during extension of (e.g. random) primer combinations having primers that anneal to a more 3' position on the template RNA (upstream primers in the direction of the extension products), wherein the reverse transcriptase will displace the extension products of all primers that have hybridized to a more 5' position on the template RNA (downstream primers in the direction of the extension products). Therefore random priming is a DNA synthesis method with a strong bias to overrepresent the 5' ends of a given template nucleic acid (see also FIG. 1 for a schematic representation of the problem and FIG. 15 for qPCR measurements of the bias). Besides using randomers (e.g.: random hexamers) for cDNA library preparation and in radio labeling of DNA probes [7, 8], they are also used to detect Single Nucleotide Polymorphisms (SNPs) as well as small scale chromosome events, primarily insertions or deletions [5, 6]. Comparative Genomic Hybridization (CGH) has been developed to elucidate genome-wide sequence copy-number variation (CNV) between different genomes, such as the differential amplification or deletion of genetic regions between tumor DNA and normal DNA from neighboring unaffected tissue [9, 10].

Currently one of the most complete analysis methods for DNA libraries is Next Generation Sequencing (NGS) [for review see 11]. NGS is a generic term for parallel sequencing through polymerization in a high throughput manner. NGS is based on obtaining sequencing reads from small fragments. In the generation of cDNA libraries, either the mRNA is fragmented before cDNA synthesis or single stranded or double stranded cDNA is fragmented. However, any fragmentation of template nucleic acids (chemical or physical) introduces an undefined and not foreseeable bias and will deplete the template. In NGS, the complete sequence is obtained by alignment of those reads which is a challenging task due to the sheer number of small reads that have to be assembled to a complete sequence. To date many reads provide just limited information. For instance many of the reads cannot be assigned uniquely and therefore are discarded. Sequence generation is further hindered by representation bias of sequence fragments.

Therefore there is the need for improved methods for amplifying template nucleic acids that yield less bias in the amplified amount, e.g. for NGS or for the generation of DNA libraries to improve representation of the sequence concentration of the original template.

SUMMARY OF THE INVENTION

Therefore the present invention provides a method for generating an amplified nucleic acid portion of a template nucleic acid, comprising
obtaining said template nucleic acid,
annealing at least one oligonucleotide primer to said template nucleic acid,
annealing at least one oligonucleotide stopper to said template nucleic acid,
elongating the at least one oligonucleotide primer in a template specific manner until the elongating product nucleic acid reaches the position of an annealed oligonucleotide stopper, whereby the elongation reaction is stopped, wherein in said elongation reaction said oligonucleotide stopper is not elongated, and
wherein the elongated product nucleic acid is labelled at the 3' end at a position adjacent to said oligonucleotide stopper and/or
wherein the elongated product nucleic acid is ligated to the 5' end of said oligonucleotide stopper; thus obtaining an amplified nucleic acid portion.

In a further aspect the present invention provides a method of generating an amplified nucleic acid of a template nucleic acid, comprising
obtaining said template nucleic acid,
annealing a first oligonucleotide primer to said template nucleic acid,
annealing at least one further oligonucleotide primer to said template nucleic acid,
elongating said first oligonucleotide primer in a template specific manner until the elongating product nucleic acid reaches the position of one of said further oligonucleotide primers, whereby the elongation reaction is stopped, and at least one further oligonucleotide primer is elongated in a template specific manner, wherein the elongated product nucleic acid is labelled at the 3' end at a position adjacent to said further oligonucleotide primer and/or wherein the stopped elongated product nucleic acid is ligated to the 5' end of said further oligonucleotide primer; thus obtaining an amplified nucleic acid portion. In this method said further oligonucleotide primer serves both as a stopper, which prevents further elongation of an amplification reaction that reaches the position of the annealed stopper, and as a primer itself, i.e. as an initiator of elongation.

The template nucleic acid can comprise or substantially consist of RNA or DNA, in preferred embodiments said template is RNA.

In a preferred aspect the present invention provides a method of generating an amplified nucleic acid of a template nucleic acid, which is RNA, comprising
obtaining said template RNA,
annealing a first oligonucleotide primer to said template RNA,
annealing at least one further oligonucleotide primer to said template RNA and/or at least one oligonucleotide stopper,
elongating said first oligonucleotide primer in a template specific manner until the elongating product nucleic acid reaches the position of one of said further oligonucleotide primers or oligonucleotide stopper, whereby the elongation reaction is stopped,
wherein in said elongation reaction said optional oligonucleotide stopper is not elongated and/or at least one further oligonucleotide primer is elongated in a template specific manner. In preferred embodiments the elongated product nucleic acid is ligated to the 5' end of said oligonucleotide stopper or further primer.

In a further aspect, the present invention provides the use of the inventive methods to generate a sequence library of one or more template nucleic acids comprising a mixture of, preferably overlapping, amplified nucleic acid portions of said template nucleic acids. A sequence library is a collection of DNA fragments that can be stored and copied through any process known in the art. For instance a sequence library can be obtained through the process of molecular cloning. Sequence libraries can also be amplified through e.g. PCR using universal sequences on the ends of the DNA fragments.

The invention also relates to a kit for generating amplified nucleic acid portions of a template nucleic acid or for generating a sequence library as mentioned above. An inventive kit comprises a reverse transcriptase, random oligonucleotide primers which comprise a modification that increases the Tm (melting temperature) and random oligonucleotide stoppers that are unsuitable for nucleotide extension and comprise a modification that increases the Tm, optionally further one or more of reaction buffers comprising $Mn^{2+}$ or $Mg^{2+}$, a ligase, preferably a DNA ligase or RNA ligase with DNA ligating activity, PEG.

The following detailed disclosure reads on all aspects and embodiments of the present invention.

DETAILED DISCLOSURE OF THE INVENTION

Figure 1:
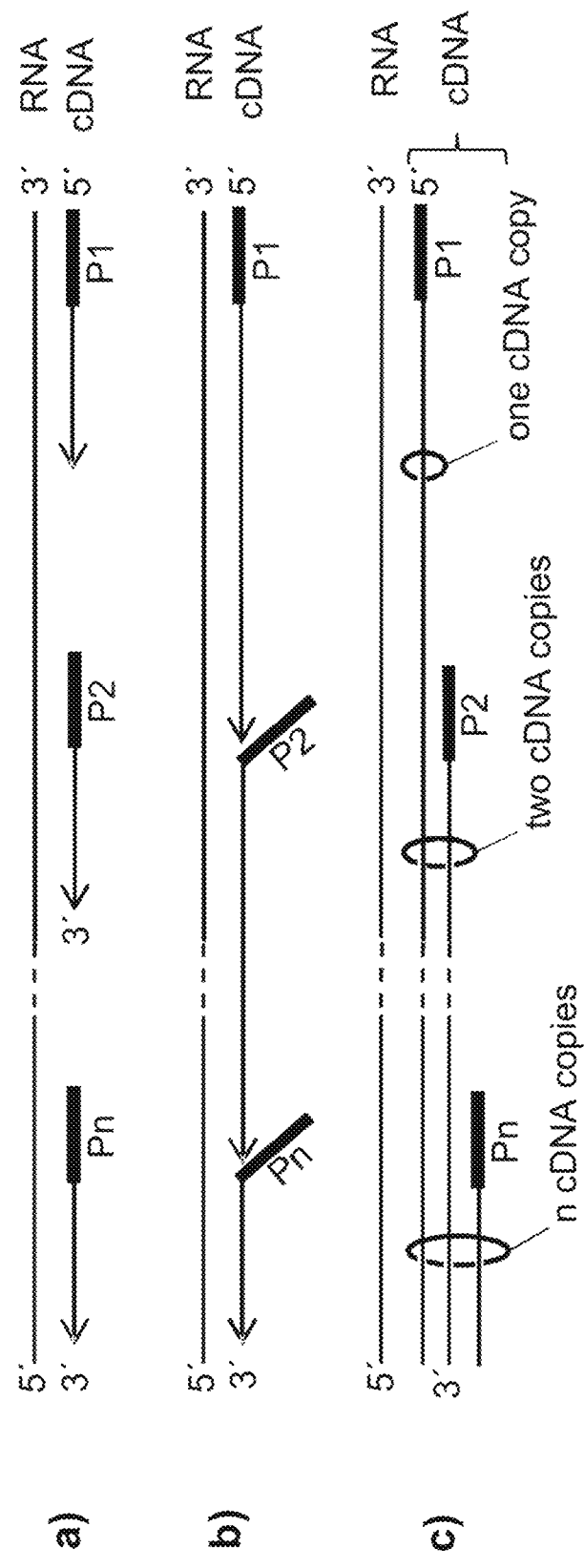
FIG. 1 is a schematic representation of the principle problem the invention seeks to solve.

The present invention provides a method for generating an amplified nucleic acid or amplifying nucleic acids. This generation can relate also to a single amplification reaction, e.g. one transcription cycle, or more. It includes the generation of RNA or DNA by RNA or DNA dependent polymerization. Thus, amplifying nucleic acids included polymerization of RNA nucleotides based on an RNA or a DNA template nucleic acid or the polymerization of DNA nucleotides based on an RNA or a DNA template nucleic acid. Preferably the method includes one step or cycle of reverse transcription, RNA dependent DNA polymerization.

The inventive methods include the use of at least two short oligonucleotides that hybridize with the template nucleic acid. At least one oligonucleotide has a primer function, i.e. it can act as nucleotide polymerization initiator for polymerase dependent amplification, i.e. transcription. The extension of primers by the addition of nucleotides in a template dependent fashion is referred herein as elongation or extension. The products of such reactions are called elongation products or extension products. RNA or DNA polymerases add nucleotides to given oligonucleotide strand which base pair to a nucleobase of a template strand. Hybridization and annealing is understood as base pairing of complementary nucleotides. Complementary nucleotides or bases are those capable of base pairing such as A and T (or U); G and C; G and U.

At least one further oligonucleotide has a stopper function. This means that as an elongation (extension) reaction that has been initiated at an upstream primer (in the direction of the extension products) reaches a downstream (in the direction of the extension products) oligonucleotide with a stopper function, said elongation reaction is prevented from further elongation. Relative to the nucleotide position on the template nucleic acid this means that once an elongation reaction that has been initiated from a primer that has annealed more to the 3' end of the template nucleic acid relative to the oligonucleotide with the stopper function, reaches that oligonucleotide (stopper), said elongation reaction is prevented from further elongation. The elongation reaction can be stopped by strong hybridization of the oligonucleotide with stopper function to the template nucleic acids so that it is not displaced by the polymerase.

The oligonucleotide with stopper function can also be a primer. It can hybridize downstream (in the direction of the elongation reaction, upstream in the direction of the template) to a first primer and stop the elongation reaction of said first primer. In turn (or simultaneously) it acts as elongation initiator itself to produce a transcription product—that in turn may also be stopped at the position of a further downstream (in relation to the direction of the elongation reactions) oligonucleotide with stopper function.

"Upstream" relates to the direction towards the 5' end (3'-5') of a given nucleic acid or oligonucleotide. "Downstream" relates to the direction towards the 3' end (5'-3') of a given nucleic acid or oligonucleotide. Since oligonucleotides hybridize in inverse fashion downstream for a primer relates to the upstream direction of a hybridized template nucleic acid. This means that a downstream oligonucleotide (or oligo, or primer or stopper or blocker) is an oligo that hybridized to a more upstream portion of a template nucleic acid in relation to an upstream oligonucleotide (or oligo, or primer or stopper or blocker) that has hybridized to a more downstream portion of a template nucleic acid. Therefore, when using the term "downstream oligonucleotide", or "upstream oligonucleotide" the directionality always refers to that of the extension product(s), except when stated otherwise. The polymerase dependent elongation reactions of the invention are in 5'-3' direction, downstream.

As used herein, "comprising" shall be understood as referring to an open definition, allowing further members of similar or other features. "Consisting of" shall be understood as a closed definition relating to a limited range of features.

As used herein "primer" may also refer to an oligonucleotide primer. "Stopper" refers also to oligonucleotide stopper. "Oligo" is used for both oligonucleotide primers and oligonucleotide stoppers.

An oligonucleotide stopper is an oligonucleotide that can stop an elongation reaction as described above and does not initiate a further elongation reaction, e.g. the oligonucleotide is incapable of accepting (covalently binding) a further nucleotide at its 3' position. Such nucleotides are known in the art and usually lack a 3' OH, as e.g. in ddNTS (dideoxynucleotides).

Thus, the present invention essentially provides two methods, one utilizing oligonucleotide stoppers and one further oligonucleotide primers. Apart from this difference, the methods comprise the inventive similarity to provide limited and well defined amplification products that can be amplified in well controlled fashion and most importantly, with a unitary concentration distribution over the length of the template nucleic acid. The inventive amplification products can be further characterized and used. They are the desired products that are obtained and not discarded, like in template suppression methods. The present invention generates amplified nucleic acid products that better represent the template molecules that need to be analyzed and prepares those for seamless integration with subsequent analysis methods such as next generation sequencing or as sequence library. If the stoppers are at the same time primers, it is possible to provide one continuous sequence based on only one template molecule. This continuous sequence of the amplified product can be provided as single molecule when the individual product sequences are covalently connected, e.g. ligated. Such connection or ligation reaction can be performed while hybridized to the template strand to secure that the products are connected in the same order as the template strand (while of course being the reverse complement strand).

The advantages of the present invention are most prominent with long template nucleic acids that are amplified according to the invention. Such templates may be at least 100 bases, at least 1000 bases (1 kb), at least 2 kb, at least 4 kb, at least 6 kb, at least 10 kb, at least 20 kb, at least 30 kb, at least 40 kb, at least 50 kb, in length.

In case of a reverse transcription an embodiment of the present invention relates to a method of reverse transcribing an RNA molecule comprising hybridizing at least two primers to a template RNA molecule and extending primers utilizing an RNA dependent DNA polymerase, wherein the extension product of an upstream primer (downstream in the direction of the template) does not displace the extension product of a downstream primer (upstream in the direction of the template). This embodiment in general essentially comprises a primer extension reaction using a first primer that is extended but stops at (does not displace) a second primer that is also extended.

However, for a complete representation of a given template by the elongation product, direct connection of the elongated nucleotides is not necessarily required. A sample of template nucleic acids usually contains many template molecules that have the same sequence. By using many, more than one, primer and stopper combinations it is possible to have a complete representation of such a sequence by the many elongation products. Having many short elongation products is often a requirement of a nucleic acid library that fully represents the template. Thus the present invention provides the method of preparing a nucleic acid library by providing the elongation products. The library may contain the elongation products in a mixture. Preferably the elongation products, especially of templates of the same sequence, contain overlapping sequence portions. Overlapping sequence portions are easier for complete sequence assembly, as e.g. required in NGS methods and are desired to provide a library that can be used to clone any specific sequence therein without or with limited interruptions by reaching the size limits of an individual elongated nucleic acid.

In case of a reverse transcription such an embodiment of the present invention relates to a method of reverse transcribing an RNA molecule comprising hybridizing at least two oligonucleotides, one a primer the other a stopper, to a template RNA molecule and extending the primer utilizing an RNA dependent DNA polymerase, wherein the extension product of the upstream primer (downstream in the direction of the template) stops at (does not displace) the position of the downstream stopper (upstream in the direction of the template). Said stopper is not extended. This embodiment in general essentially comprises a primer extension reaction using a first primer that is extended but stops at (does not displace) an oligonucleotide stopper that is not extended.

It is possible to combine the inventive embodiments, e.g. by using at least two primers and a stopper, a first upstream primer that is extended downstream, which extension reaction stops at the position of a second, downstream primer that is also extended downstream, which extension reaction in turn stops at the position of the oligonucleotide stopper.

In special embodiments no oligonucleotide stoppers that cannot be extended are used. In such embodiments only extendable primers may be used during amplification/transcription.

In other embodiments it is desired to obtain amplification products that have been stopped at oligonucleotide stoppers. To this end a skilled man can e.g. select such elongated nucleic acids by well-known methods, such as by labeling, including immobilization onto a solid phase (e.g. beads or a solid surface) or by attaching a barcode sequence or sequence tag. The elongated products may also be ligated to the oligonucleotide stopper—similar to the ligation with primers with stopper function in order to provide one long product molecule as mentioned above. Labeling and ligating to the oligonucleotide stopper can be combined, e.g. by labeling the oligonucleotide stopper and ligating the extension product to a labeled oligonucleotide stopper. Of course, labeling of the oligonucleotide stopper can be performed after ligation with the extension product. Such labeling allows the easy handling, selection and/or amplification of the elongated products. E.g. a sequence tag can be used for further selected amplification of said elongated and so labeled elongation products by using primers that hybridize to such a tag and can initiate an amplification reaction, e.g. PCR, of said (previously) elongated nucleic acid product. This is particularly advantageous if a multitude of different elongation products are obtained and many are labeled with the same sequence tag. In case of sequence libraries this method allows an easy amplification of an entire library—still with a consistent representation of the amount of all sequences over the entire length of the original template.

In preferred embodiments more than one oligonucleotide primer is used, which functions similar as the first primer but has a different primer sequence, the sequence that anneals to a target template. In particular the inventive method according to this embodiment further comprises annealing an additional oligonucleotide primer to said template nucleic acid and elongating said additional oligonucleotide primer until the elongating product nucleic acid reaches the position of another oligonucleotide primer or an oligonucleotide stopper. In especially preferred embodiments at least 1, at least 2, at least 3, at least 4, at least 5, at least 6, at least 7, at least 8, at least 9, at least 10, at least 15, at least 20, at least 30, at least 40, at least 50 or more different oligonucleotide primers are used. "Different oligonucleotide primers" is understood that they differ in a primer sequence but, of course, may share other similar sequence portions, such as sequence tags. Such sequence tags are preferably used in a further amplification reaction of the elongated products by using primers that anneal to the sequence tags. Thus, with one primer all potentially different products can be amplified. In a special embodiment the oligonucleotide primers are random primers. "Random primers" is to be understood as a mixture of different primers with different primer sequence portions, with a high variance due to a random synthesis of at least a portion of the primer sequence. Random primers potentially cover the entire combinatory area for said sequence. The random sequence primer portion of the random primer may cover 1, 2, 3, 4, 5, 6, 7, 8 or more nucleotides which are randomly selected from A, G, C or T (U). In terms of hybridizing sequences of primer sequences T and U are used interchangeably herein. The full combinatory possible area for a random sequence portion is $m^n$, wherein m is the number of nucleotide types used (preferably all four of A, G, C, T(U) and n is the number of the random nucleotides. Therefore a random hexamer, wherein each possible sequence is represented, consists of $4^6=4096$ different sequences.

Likewise it is also possible to use more than one oligonucleotide stopper in any one of the inventive methods. Said additional stoppers act similar as the first stopper, but differ in the sequence aligned to the template. The same as described above for additional primers applies for the additional stopper—of course with the difference that the stoppers are not suitable for elongation reactions. Therefore, for consistency the region of the oligonucleotide stopper that hybridizes to the template is also referred to as "primer sequence". Said primer sequence may be 4, 5, 6, 7, 8, 9, 10, 11, 12, 13, 14, 15, 16, 17, 18, 19, 20, 21, 22 or more nucleotides long. The invention thus provides a method as defined above further comprising annealing an additional oligonucleotide stopper to said template nucleic acid and wherein in said elongation reaction said additional oligonucleotide stopper is not elongated. In preferred embodiments at least 1, at least 2, at least 3, at least 4, at least 5, at least 6, at least 7, at least 8, at least 9, at least 10, at least 15, at least 20, at least 30, at least 40, at least 50 or more different oligonucleotide stoppers are used. The oligonucleotide stoppers may be random oligonucleotide stoppers, comprising a random primer sequence that anneals to the template. As described above for oligonucleotide primers, also oligonucleotide stoppers may share similar sequence portions, such as tags or barcodes that may be used for amplification or identification of the products. Such kinds of labels allow easy identification in a sequence library comprising the inventive amplification products.

As described in the introduction a (randomly) primed cDNA library without control of the elongation reaction (and its stop) distorts the actual RNA representation of sequence portions. Even on e.g. short mRNA templates (200-1000 nt) multiple priming events can occur and with the strand displacement the 5' side of RNA molecules will be present in more copies than the 3' side (see also FIG. 1). Therefore when measuring the concentration of a certain gene transcript different values will be obtained when probing for sequence portions at the 5' or 3' end. Short random probes are commonly used in microarray and quantitative PCR analysis. This leads to severe distortions of the concentration measured. Furthermore, this distortion will be greater when comparing long and short transcripts, as the 5' ends of high abundant long transcripts will be even higher represented than the 5' ends of shorter transcripts. When globally analyzing the concentration of transcripts such as in high throughput sequencing (e.g. next generation sequencing) in addition to distorting concentrations detecting rare short transcripts becomes even less likely than detecting rare long transcripts. As the differential expression of gene transcripts and their splice variants is an important part of phenotype analysis, it is important that each sequence portion of a transcript is represented in the generated cDNA library at the correct abundance.

These problems are solved by the present invention. Applying the inventive methods to provide well defined transcripts, stopped at a primer or stopper position (preferably with inhibited strand displacement of the reverse transcriptase) during the generation of cDNA from a multitude of RNA molecules as for instance in the generation of a cDNA library of mRNA molecules, enables the equal representation of each portion of the RNA molecules. For instance mRNA can be primed with random primers such as random hexamers that are modified to ensure that the random primer does not get displaced by the reverse transcriptase. Any random primer can be used that can start reverse transcription from multiple sites from the template RNA molecules.

The present invention also provides for methods that enable the covalent joining (e.g.: through a ligation) of the obtained elongated products as they are provided in a hybrid with the template (see also FIG. 2c). This enables the generation of a full length amplified nucleic acid molecule.

Figure 15:
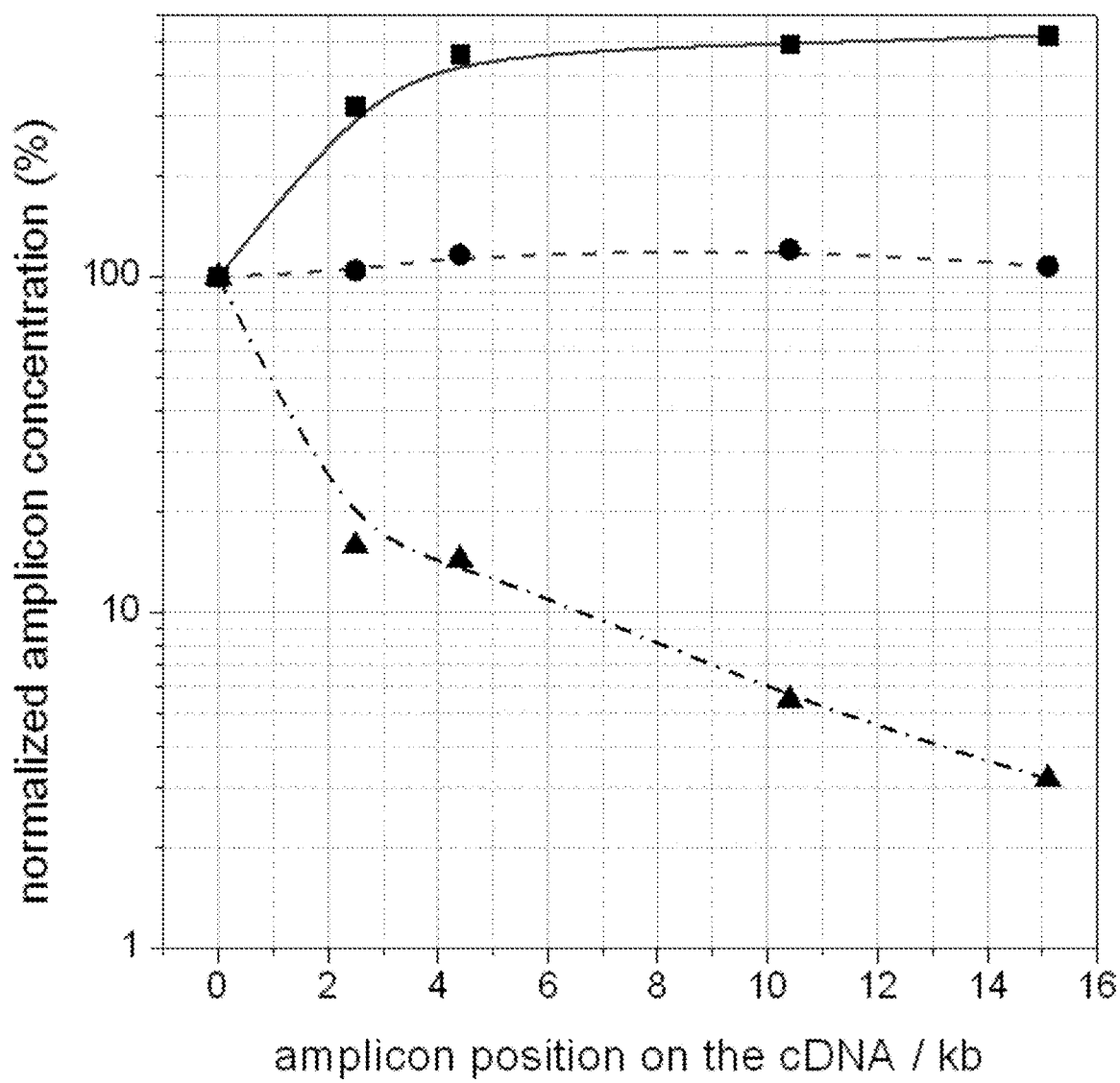
FIG. 15 is a graph depicting cDNA length comparison of SDS/ligation vs oligo dT priming on a 15 kb cDNA.

Using primers that provide for a 5' phosphate, it has been found that the "short" elongated nucleic acids—that are essentially fragments of the complementary strand to the template strand—can be ligated while still being hybridized to the template. This will result in long and in most cases full length amplified nucleic acid molecules that are a direct representation of the template. Being able to preserve the information of the full length sequence of a template is, for instance, important when splice variants of a gene need to be analyzed. Especially when splicing of multi exonic genes is complex the analysis of single splice junctions alone will not yield unambiguous information towards the full length sequence of the transcript variant involved. However, only oligo dT priming in case of mRNA or priming from a 3' ligated universal linker from any nucleic acid template will lead to an underrepresentation of the 5' side of the template. In other words, the longer the template is the less likely it becomes that the molecule will be reverse transcribed to full length. As can be seen in FIG. 15, when a standard oligo dT primed RT is used on average after 6 kb only ~10% of RNA molecules are reverse transcribed to full length. As the present invention provides—in one embodiment—for methods that will start the polymerization from two or more positions of a template molecule with an elongation reaction that is stopped at the position of a downstream primer, the extension product of the upstream primer can be ligated to the 5' end of the downstream primer. By covalently joining both extension products when in hybrid with the template a longer sequence is created. In continuation when many different primers are used potentially all templates present in the sample can be transcribed and by ligating the short extension products a full length amplified copy of the template can be created (see also FIG. 2c, d).

Likewise, according to the inventive embodiments utilizing oligonucleotide stoppers, a ligation with the elongated product can be performed to obtain well defined amplified nucleic acids of an amplification of a sequence between the primer and the stopper.

In preferred embodiments the oligonucleotide primers and/or oligonucleotide stoppers are phosphorylated or adenylated on the 5' end. This measure helps to easily ligate the oligonucleotide primers or stoppers to another nucleic acid, such as the elongation product, in one or few steps using a ligase. In some embodiments, especially when mixtures of many primers and stoppers are used, it is possible to only provide the stoppers with such a modification to ensure ligation of elongated nucleic acids with stoppers and prevent ligation with other primers.

Any ligase known in the art can be used, such as T4 RNA ligase, T4 DNA ligase, T4 RNA ligase 2, Taq DNA ligase and E. coli ligase.

To prevent any non-hybridized primers or stoppers from being ligated a preferred embodiment of the invention uses a double strand specific ligase such as T4 RNA ligase 2 or T4 DNA ligase. Double stranded DNA is the natural substrate of T4 DNA ligase and DNA-RNA hybrids are poor substrates [29]. In order to overcome this inefficiency $Mg^{2+}$ can be replaced with $Mn^{2+}$ as a divalent ion for the enzyme [30]. In one embodiment of this invention the addition of PEG to the ligation reaction is shown to increase the ligation efficiency of DNA molecules in an RNA hybrid even in a $Mg^{2+}$ containing ligase buffer.

Optionally a T4 RNA ligase, which is deficient of adenylation (e.g. truncated), can be used for ligation which relies on the presence of adenylated DNA fragments that are in the hybrid with the RNA (adenylation with T4 DNA ligase occurs exclusively in double stranded nucleic acids). It can be added additionally to the ligation reaction to further increase the efficiency. The ligation happens exclusively in the hybrid and was previously considered very inefficient form of ligation [31]. In U.S. Pat. No. 6,368,801 a ligation of 2 DNA molecules (with ribonucleotides at their 3' and 5' ends) in an RNA hybrid by T4 RNA ligase is described. However T4 RNA ligase is not specific for hybrids since it ligates all single stranded nucleic acids containing deoxyribonucleotides at their 5' or 3' end (RNA to DNA, RNA to RNA, DNA to DNA providing there is one deoxyribonucleotide at the 3' and 5' end) as well. The present invention includes the addition of PEG in the ligation reaction, which allows the ligation to take place in the RNA hybrid. PEG has been used in single stranded ligation reactions as a molecular crowding agent, increasing the likelihood of the donor oligonucleotide ligase complex interacting with the acceptor (3'OH) by decreasing the effective reactive volume [32]. Here in contrast the donor oligonucleotide ligase complex is already next to the acceptor and PEG serves to change the conformation of the RNA:DNA hybrid by condensing the double helix into a conformation that is more reminiscent of a DNA:DNA helix, so that the T4 DNA ligase that normally is specific for ligating two DNA molecules in a hybrid with a DNA strand, can ligate two DNA molecules that are in a hybrid with an RNA molecule. Alternatively T4 RNA ligase 2, which is a double strand-specific ligase can be used.

Other additives such as Tween-20, NP-40 could be added additionally or instead of PEG for efficient ligation in the RNA hybrid. Within the scope of the invention the ligation reaction requires 12%-25% final PEG-8000 (v/v). A variety of PEG molecular weights and compounds can be used, and the skilled experimenter will appreciate that the identity and concentration of the additive can be varied to optimize results. In the context of the present invention, an effective amount of PEG is an amount sufficient to permit ligation activity in an RNA hybrid. In a 20 µl RT reaction the optimal PEG concentration for a ligation in an RNA hybrid was found to be 20%. However, it is apparent to the skilled in the art that optionally the reaction volume and the PEG concentration can be increased or decreased (e.g. decrease in volume, increase in PEG amount or concentration) to potentially further optimize the ligation efficiency of 2 DNA molecules in an RNA hybrid by T4 DNA ligase or T4 RNA ligase 2. Other additives such as 1 mM HCC and/or pyrophosphatase can further increase the ligation efficiency in an RNA hybrid.

Pre-adenylated oligonucleotides can be inserted into the reaction and used with truncated T4 RNA ligase, provided that any unhybridized oligonucleotides have been removed prior to the ligation reaction. As mentioned before in another embodiment of this invention truncated T4 RNA ligase 2 can be added in addition to T4 DNA ligase to further boost the ligation of DNA fragments in an RNA hybrid.

Therefore it is preferred that the ligase is a double strand specific ligase such as T4 DNA ligase or T4 RNA ligase 2 and wherein it is preferred that Polyethylene glycol is used at a concentration between 12% and 25%.

Apart from a representative template amplificate synthesis an additional benefit of the present invention is the improved efficiency of generating long product nucleic acids, especially cDNA synthesis, resulting in higher sensitivity of detection and longer products (see Example 5 and 6).

In preferred embodiments any one of the oligonucleotide primers may comprise a sequence tag. Such a sequence tag is a label in form of a unique pre-selected nucleic acid sequence that can be used to detect, recognize or amplify a sequence labelled with said tag. Preferably a uniform sequence tag is attached to more than one of the oligonucleotide primers, especially preferred to all of the oligonucleotide primers. Such a sequence tag is preferably prevented from annealing to the template, e.g. by being hybridized to a complementary nucleic acid. Sequence tags can be attached to the 5' end of the oligonucleotide stopper—so as not to prevent the elongation reaction of the primer at its 3' end.

In preferred embodiments any one of the oligonucleotide stoppers may comprise a sequence tag. Such a sequence tag is a label in form of a unique pre-selected nucleic acid sequence that can be used to detect, recognize or amplify a sequence labelled with said tag. Preferably a uniform sequence tag is attached to more than one of the oligonucleotide stoppers, especially preferred to all of the oligonucleotide stoppers. Such a sequence tag is preferably prevented from annealing to the template, e.g. by being hybridized to a complementary nucleic acid. Sequence tag can be attached to the 3' end of the oligonucleotide stopper. At this position the tag does not hinder the contact of the elongating product nucleic acid to the 5' end of the stopper—resulting in well-defined products. It also allows ligation of the elongated product to the oligonucleotide stopper. Alternatively the tag may be on the 5' end of said stopper, however, prevented from hybridization to the template so that the elongation reaction still reaches the 5' end of the primer region of the stopper. Said tag preferably comprises a free 5' end so that the elongated product can be ligated to the tag for labelling of the elongated product by said tag. A free 5' end of the tag that can be easily ligated to the product is preferably provided in the vicinity of the 3' end of the elongated product. This can be achieved by e.g. providing the tag hybridized to a complementary region of the oligonucleotide stopper, said complementary region being hybridized with the tag and attached to the 5' end of the primer region of the oligonucleotide stopper (for an example see FIG. 4).

The inventive labelling step of the elongated product when it reaches the position of the oligonucleotide stopper (or another primer), preferably a stopper, can be achieved with any known means readily available in the art. Such means include attaching a chromophore, fluorophore or simple phase separation by binding to a solid phase and washing of said solid phase to remove all non-bound nucleic acids, thereby isolating the labelled nucleic acid. In preferred embodiments said labeling step comprises ligation with a sequence tag. A sequence tag may be attached to said oligonucleotide primers or oligonucleotide stoppers. Labelling may also comprise ligation with said oligonucleotide primers or oligonucleotide stoppers, which comprise a sequence tag.

For many downstream analyses it is preferred that oligonucleotides, such as primers, stoppers, blockers or linkers get depleted. Especially, when an amplification of the library utilizing the universal linker sequences is necessary or desired it is preferable to deplete the un-ligated linkers.

This can be achieved through for instance a size exclusion, retaining the oligonucleotides (shorter) in an appropriate bed, and recovering the library (longer). Another possibility is to bind the longer library to a silica based carrier while not retaining the shorter oligos. Such discrimination can also be carried out to distinguish between the single strandedness of the oligo and the double strandedness of the library when still in hybrid with the template. Another possibility for length based purification are methods based on PEG precipitation. The higher the PEG concentration the shorter the nucleic acids that can be precipitated. For instance, it was found that using a 12.5% PEG precipitation, all small fragments (below 60 nts) will stay in the solution and only the cDNA and the linker ligated library will precipitate.

In a preferred embodiment a beads-based clean-up approach is used. Oligo dT coupled beads or Streptavidin beads to isolate biotin labeled oligodT primers are commercially available. A beads based clean up has the additional advantage that both RT and ligation can be performed on the beads. After hybridizing the mRNA to the oligo dT (biotin tagged or on beads) and to the starter and stoppers, any non-hybridized starter and stopper excess can be washed off before starting the RT reaction. Thus in preferred embodiments of the invention the template nucleic acid is immobilized on a solid phase or solid support, preferably beads. The amplified nucleic acids hybridized to said template nucleic acid may then be washed.

Another embodiment of the invention is that RT and ligation can be performed in one reaction step, simply by adding Ligase (e.g.: T4 DNA ligase or T4 RNA ligase 2), 10% PEG, and 0.4 µM ATP to the reverse transcription reaction in a regular reverse transcription reaction buffer. Although 30 min incubation can be used, a better yield was obtained using 2 h incubation at 37° C. Following another washing step (4 washes) the RNA can then be hydrolyzed to obtain the di-tagged cDNA library, which can then be inserted into a PCR reaction. RT and ligation can also be performed in two successive reaction steps, re-buffering the reaction simply by washing the beads. However, in a preferred embodiment of the invention a simultaneous RT/ligation reaction is performed since this resulted in similar yield as the two step protocol, but has the advantage of reduced hands on and incubation times. Simultaneous RT and ligation can be performed by addition of a DNA polymerase and ligase in one reaction mixture with the template nucleic acid.

In preferred methods of the invention said elongated products are amplified. Amplification may comprise using tag specific primers to amplify elongated products that comprise a 5' and/or 3' tag, stemming from the tag-labelled oligonucleotide primer and/or stopper, respectively. Amplification is preferably by PCR. Sequence tags suitable for primer hybridization in a following amplification cycle are also referred to herein as "linkers".

Currently any preparation of small cDNA fragments for high throughput sequencing such as NGS involves fragmentation of RNA and in most cases a multistep procedure to introduce the 5' and 3' linker tags for amplification and bar-coding. For instance Epicentre's ScriptSeq™ mRNA-Seq Library Preparation Kit uses terminal-tagging technology (US 2009/0227009 A1) and random-priming on chemically fragmented RNA (depleted of ribosomal RNA). However, any fragmentation of mRNA (chemical or physical) introduces an undefined and not foreseeable bias. In addition during fragmentation protocols a portion of the RNA is degraded or gets lost. Therefore the present invention is ideally suited to generate cDNA libraries of a rather defined short size without the need of RNA fragmentation.

In addition when the RNA is fragmented many additional 5' ends are created. Reverse transcriptases have the tendency to add a few non-template nucleotides when they reach the 5' end of the template RNA and use these nucleotides for priming second strand synthesis. Therefore when RNA is fragmented more 5' ends are generated and therefore more second strand synthesis is initiated. One important question during RNA sequencing is the question from which DNA strand an RNA was transcribed. Especially in the analysis of sense and antisense transcription a high strandedness (conservation of strand information) of the library sequenced is required. Therefore as no RNA digestion is needed in the present invention a much higher degree of strandedness can be achieved in the cDNA library generated (see also example 9) compared to library preparation methods that include RNA fragmentation.

Of course this method can be employed for the generation of fragments to any kind of template nucleic acid and is not limited to RNA. Such fragments are provided by the inventive elongated products or amplified nucleic acid portions. The template nucleotide sequence could also be DNA. Hence a library preparation using the techniques described in this invention can also be started from genomic DNA or PCR products. Since reverse transcriptases are also accepting DNA templates [33], all steps can basically be performed as described within this invention. Optionally also DNA dependent polymerases can be used if DNA is used as template.

As for many analysis methods such as NGS, it is preferable to have defined universal linker sequences present on the 3' and/or 5' end of the cDNA. Such linker sequences can for instance serve as priming sites for PCR amplification to enrich for a library or priming sites for bridge amplification on a solid surface or to prime a sequencing reaction. Therefore it is within the scope of the invention that linker sequences are ligated to the amplified nucleic acid portions. However it is preferred that the 5' linker sequence is directly introduced with the primers (see also FIG. 3 (L1)). Here the 5' linker sequence is a 5' extension to the sequence that is used for priming the polymerase.

Figure 3:
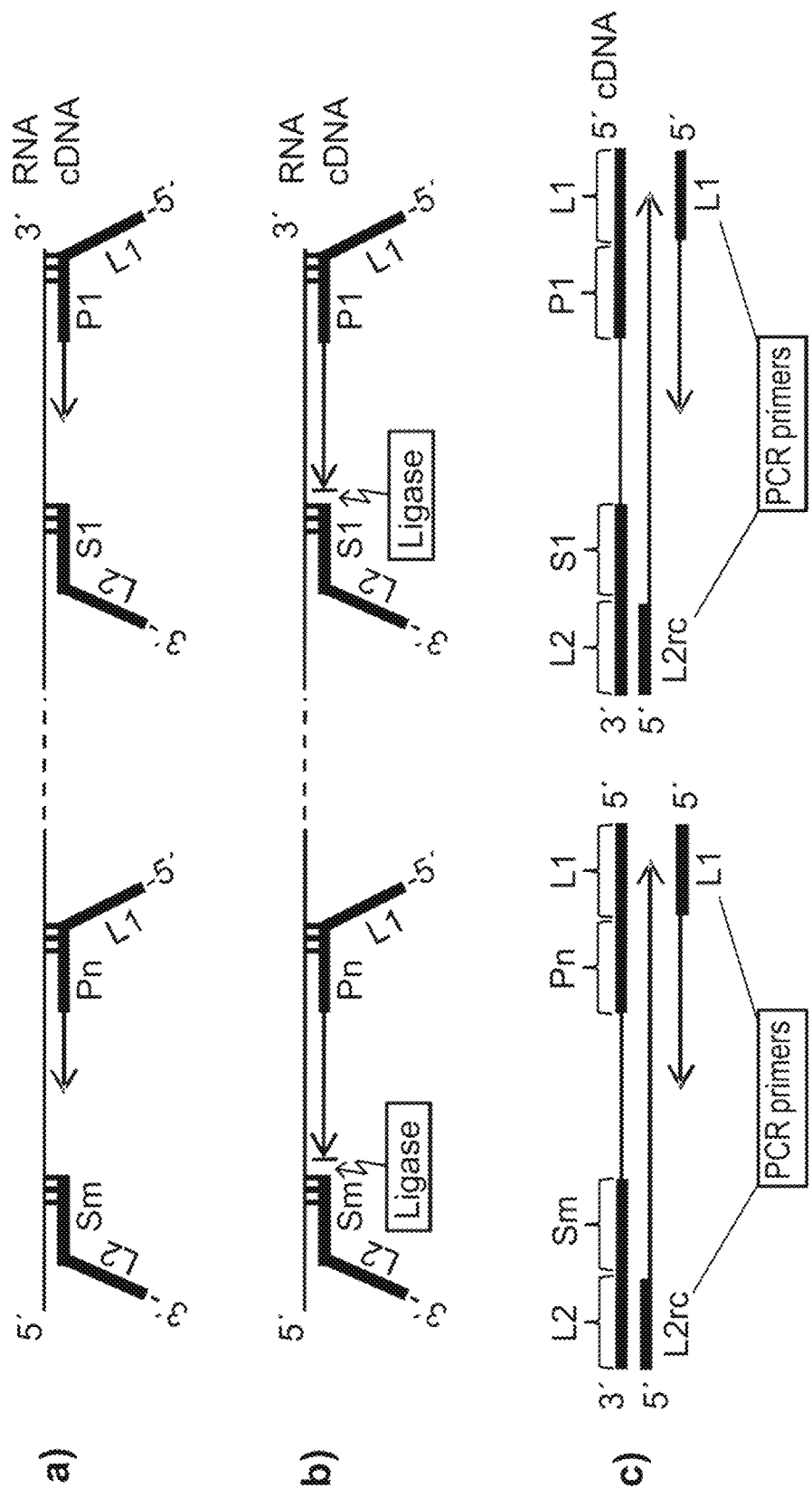
FIG. 3 is a schematic representation of creating a linker tagged short cDNA library.

Alternatively or in addition a linker sequence can be introduced on the 3' end of the elongated nucleic acid product, e.g. by using a stopper oligo (FIG. 3. (S1, Sm)) that has a linker sequence added on its 3' end (FIG. 3. (L2)). The 5' end of the stopper oligo can be ligated to the 3' end of the extension product (FIG. 3*b*). The specific ligation reaction ensures that the 5' end of the stopper oligo is not strand displaced. Therefore in a preferred embodiment a stopper oligonucleotide is added to the reverse transcription reaction and wherein the stopper oligonucleotide has a 3' linker sequence extension.

Figure 5:
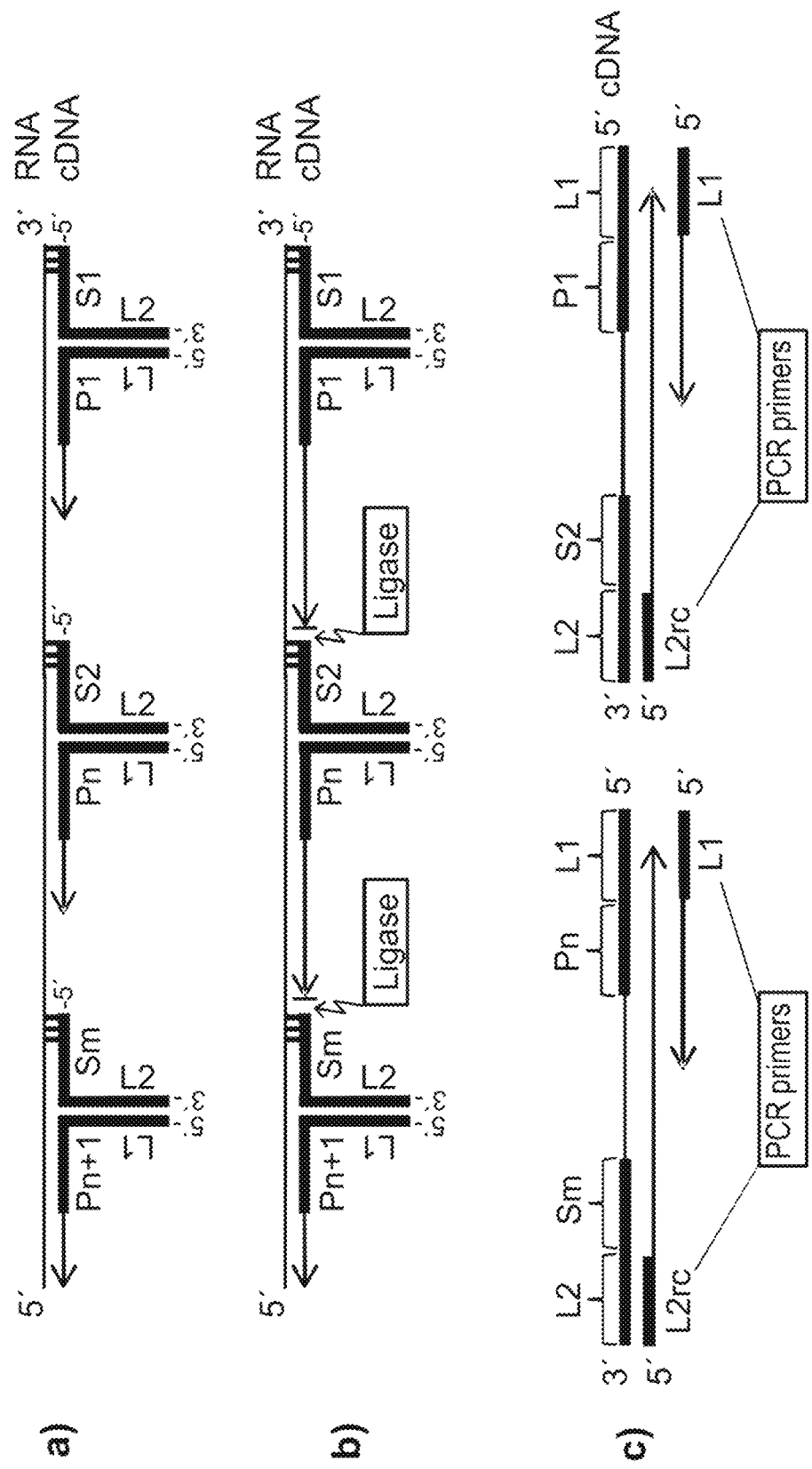
FIG. 5 is a schematic representation of creating a linker tagged short cDNA library using an alternative stopper oligo concept.
Figure 8:
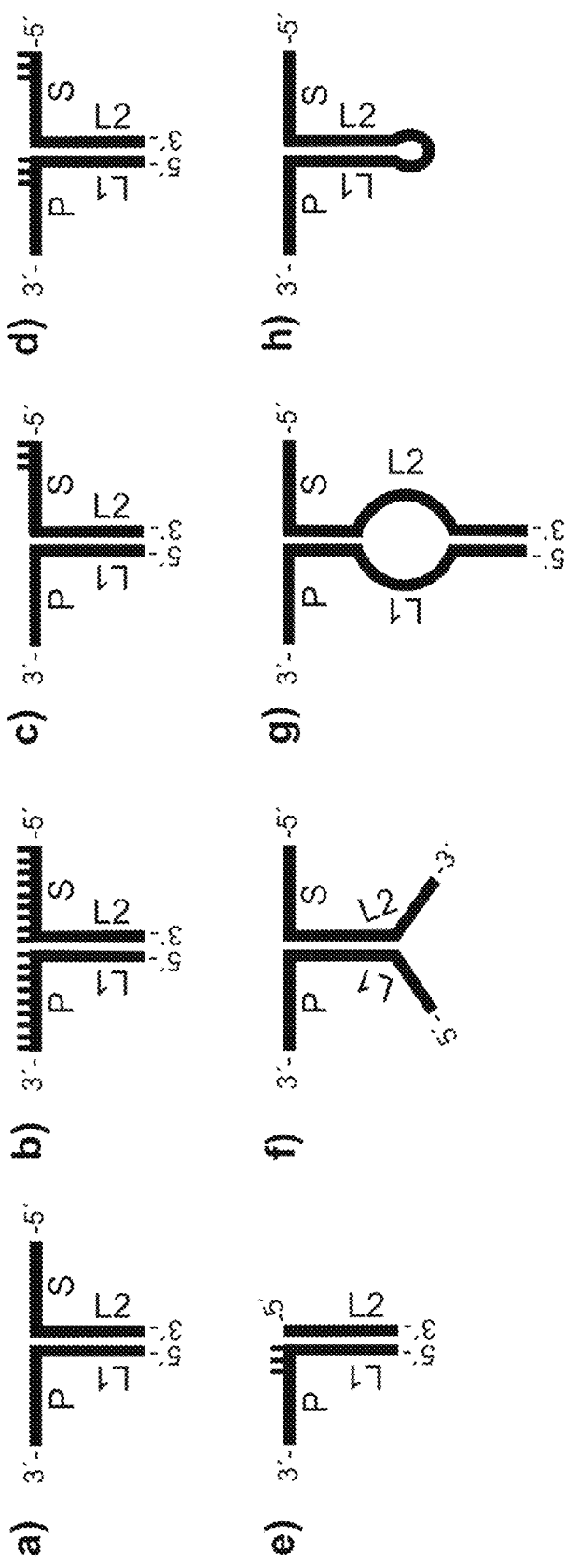
FIG. 8 is a schematic representation of the most preferred oligo starter and stopper combinations.

In an alternative version—as illustrated in FIGS. 5 and 8—the starter and stopper oligonucleotide are at least partially hybridized to each other. The 5' phosphorylated stopper oligonucleotide can either still hybridize to the template strand (as shown in FIG. 8*a-d,f-h*) or not have any hybridization to the template strand (see FIG. 8*e*). In this case the extended oligo referred to as a starter has to be the actual oligo stopping the strand displacement and hence contains preferably modifications that stop strand displacement. The extended strand from a more upstream starter will be stopped at the next starter and the phosphorylated oligo previously referred to as the stopper that is hybridized to the starter will be ligated to the extended cDNA strand.

In 8*e* an even more elaborate starter/stopper combination is shown. The details on the linker sequence L1 and L2 can be found in the description of FIG. 9.

Finally the sequence tag ("linker") of the starter and stopper oligo can be joined (see FIG. 8*h*) in order to introduce sequence tags into the cDNA, but keep the sequence of the individual extension products in order as they are now covalently linked to each other through their starter stopper sequence tags.

It is preferred that a polymerase is used during elongation that has low or no terminal transferase activity, as to not add non templated nucleotides to the 3' end of the extension product upon reaching the position of the 5' end of the stopper oligo, as a 3' overhang would reduce the specificity and efficiency of the ligation reaction. Reverse transcriptases with low terminal transferase activity are for instance Superscript III (Invitrogen); RTs with no terminal transferease activity are e.g. AMV-RT.

Alternatively or in addition terminal transferase activity and hence also second strand synthesis can be inhibited by the addition of Actinomycin D. Actinomycin D can be added to the polymerisation reaction in sufficient amounts to avoid second strand synthesis and/or to reduce strand displacement of the polymerase as compared without actinomycin addition. In a preferred embodiment Actinomycin D is added to the RT reaction at a final concentration of about 50 µg/ml, also higher or lower concentrations can also be used, such as e.g. 5 µg/ml to 200 µg/ml.

In addition or alternatively an overhang can be digested by a single strand specific nuclease, preferably a 3'-5' exonuclease, such as but not limited to Exonuclease I (3'-5' ssDNA digestion), Exo T5 (3'-5' ss or dsDNA digestion).

One of the goals of the invention is to control for any bias introduced into the sequence library obtained by the amplified nucleic acid products, and this means in most cases to minimize bias. Linker sequences that are introduced as an extension to random or semi-random priming sequences can also participate in the hybridization to the template. This will add a bias to the library generated. It is therefore preferred that at least the nucleotides of the linker that lay next to the primer or the stopper sequence are inhibited from participating in the hybridization to the template. This can be achieved through different means. For instance an oligonucleotide with a reverse complement sequence to the linker sequence can be added to the reaction (see also FIG. 6c-f; FIG. 7c-f). In that case the reverse complement will compete with the template for hybridization to the linker sequence and by using excess of reverse complement the participation of the linker sequence in priming the RT or hybridizing the stop oligo can be effectively quenched.

It is preferred to provide the reverse complement with nucleotide modifications that enhance the stability of linker:reverse complement hybrid, by using for instance LNAs. However, any other modification can be used that enhances the binding energy (see also FIG. 6e; FIG. 7e).

Furthermore, it is preferred that the primer and/or stopper are added as a premade adapter to the reverse transcription. This means that essentially all linker sequences are in a hybrid with their reverse complement strands and so the linker sequence is inhibited from participation in the hybridization reaction.

Therefore, in a preferred embodiment a reverse complement sequence to the linker sequence part of the oligonucleotides is added to the reaction, preferably already in a hybrid with the oligonucleotide primer and it is further preferred that the Tm of the reverse complement oligo is raised by e.g. introducing modifications such as LNAs, 2' fluoronucleotides or PNAs.

In a preferred embodiment the reverse complement sequence is covalently linked to the linker sequence (see FIG. 6g; 7 g). This can be either in direct continuation to the linker sequence or through a nucleotide hairpin or spacers such as C3, C6, C12, or any other moiety. In addition this moiety can be a modification that enhances adapter formation. As described before it is preferred that the nucleotides of the reverse complement are modified to enhance hybridization to the linker sequence. Therefore it is preferred that the reverse complement to the linker sequence is either directly connected to the linker sequence or through a nucleotide hairpin or spacer such as C3, C6, C12 or any other moiety.

In a most preferred embodiment a sequence tag on the primer (L1) and a sequence tag on the stopper (L2) comprise at least partially complementary sequences which allow starter and stopper to form hybrids (see FIGS. 5 and 8). In that manner the sequence tag ("linker") sequences will not hybridize to the template strand and as an added benefit a stopper-ligation will happen in immediate proximity to the next starting event, minimizing any gaps between starting and stopping events. Thus; in preferred embodiments of the invention at least one or more or all oligonucleotide stopper(s) is/are hybridized to at least one further oligonucleotide primer. In an alternative embodiment or additional embodiment in combination, at least one or more, preferably all, oligonucleotide primer(s) is/are hybridized to an oligonucleotide stopper. Especially preferred, any one of the oligonucleotide stoppers and any one of the oligonucleotide primers comprises a sequence tag each, and preferably wherein the sequence tag of the oligonucleotide primers is at least partially complementary with the sequence tag of the oligonucleotide stopper thereby enabling hybridization of the oligonucleotide stoppers and the oligonucleotide primers with each other at least in a part of the respective sequence tag.

As any free 3' OH can potentially serve as an acceptor during polymerization or ligation, it is preferred that any free 3' OH (except the one on the oligonucleotide primer) is blocked (see also FIG. 6f; FIG. 7f). Many blocking groups are known in the art. Provided for reference but not limiting are dideoxynucleotides, C-spacers and phosphate groups. In addition, the 3' end of the reverse complement in the priming adapter can also be provided with an overhang (see FIG. 6d). Correspondingly, the linker sequence of the stopping adapter can be provided with a 3' overhang (see FIG. 7d). Therefore it is preferred that the 3'OH of the oligonucleotides that do not participate in the primer extension reaction are blocked and/or where provided in a hybrid that the 3' end has an overhang over the 5' end.

Figure 4:
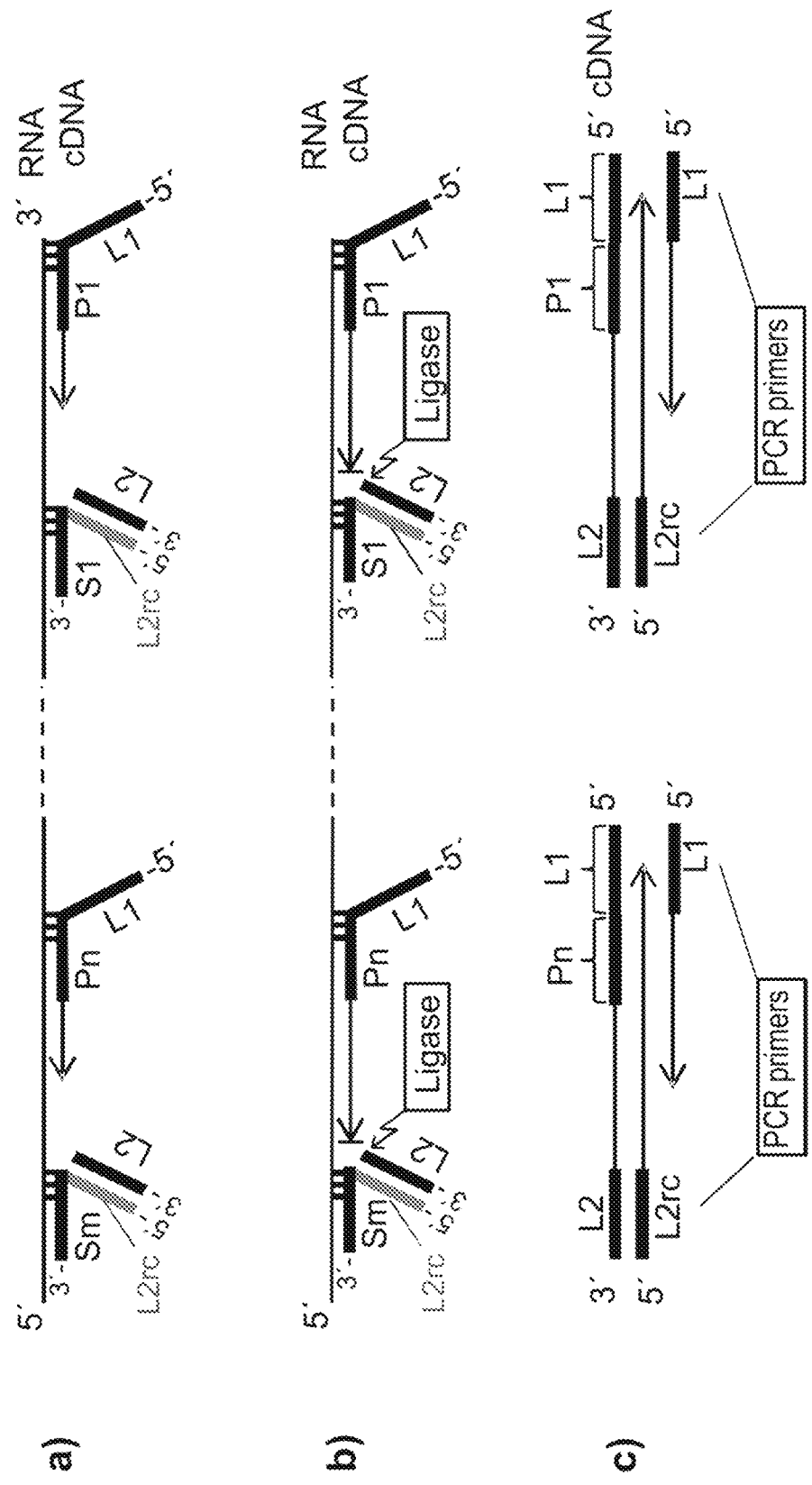
FIG. 4 is a schematic representation of creating a linker tagged short cDNA library using an alternative stopper oligo concept.

When introducing the linker sequences together with the primer and/or the stopper oligonucleotides the sequence between the linker sequences reflects the template RNA sequence. As a mis-hybridization of the primer or the stopper to the template is much more likely than the incorporation of a wrong nucleotide during polymerization, the primer sequence and/or the stopper sequence are more likely to contain an error than the polymerized sequence. Therefore, when e.g. sequencing the library in an NGS experiment, it would be preferable that the linker sequence that contains the sequencing primer is next to the primer extension product. A solution to this problem is shown in FIG. 4. Here the L2 sequence is in a hybrid with its reverse complement that has been introduced at the 5' side of the stopper oligonucleotide. In this manner the L2 sequence can be ligated to the primer extension product once the polymerase reaches and stops at the stopping oligo. However, the sequence of the stopping sequence of the oligo is not included into the library. Therefore, starting any sequencing reaction from the L2 sequence will not include a potentially mis-hybridized stopper sequence. Therefore, it is preferred that the linker sequence is on the 5' end of the stopping oligonucleotide and the 5' end of a reverse complement to the linker sequence is ligated to the 3' end of a strand displacement stopped extension product as a sequence tag. The same principle applies for the starter-"stopper" combination shown in FIG. 8e with the sole difference that the oligo responsible for stopping is actually the starter of the next library fragment.

Thus in preferred embodiments the oligonucleotide primer or oligonucleotide stopper is hybridized with a sequence tag as oligonucleotide label. Especially preferred said sequence tag is preferably hybridized to a portion on the 5' end of said oligonucleotide primer or oligonucleotide stopper. The next, e.g. 1, 2, 3, 4, 5, 6 or more, nucleotides of said primer or stopper in 3' direction next to the nucleotides of said primer or stopper that are hybridized to said sequence tag are hybridized to the template. This allows positioning of the 5' end of the tag near the 3' end of an elongation product of another primer, that is located upstream of the oligonucleotides primer or oligonucleotide stopper with the hybridized sequence tag so that the elongated 3' end of said further primer can be ligated to the 5' end of said sequence tag. Such tags may also be used for subsequent amplifications reactions of the ligated products and are also referred to as "linkers" herein.

In preferred embodiments the oligonucleotide primer and/or oligonucleotide stopper comprises a nucleotide modification increasing the Tm or stiffening the sugar phosphate backbone of said oligonucleotide. These modifications to increase the Tm are to strengthen hybridization to the template to secure stopping of the elongation reaction and prevent displacement of the primer or stopper. Such modifications are known in the art from oligonucleotide blockers, such as described in GB 2293238, US 2002/0076767 A1, U.S. Pat. No. 6,391,592 B1, WO 99/61661, WO 02/086155, U.S. Pat. No. 5,849,497, WO 2009/019008. Suitable modifications include one or more of the modifications selected from 2' fluoro nucleosides, LNA (locked nucleic acid), ZNA (zip nucleic acids), PNA (Peptide Nucleic Acid). Further the Tm can be increased by using intercalators or additives that specifically bind to nucleic acids, such as Ethidiumbromid, Sybr Green. Preferred intercalators are specific for RNA: DNA hybrids. The number of modified nucleotides may vary, depending on other measures taken to increase the Tm. Preferably 1, 2, 3, 4, 5 or 6 nucleotides are modified. Preferably the modified nucleic acids are on the 5' side of the primer sequence portion, the portion of the oligonucleotide primer or stopper that can hybridize or anneal to the template. Preferably 1, 2 or 3 5' nucleotides are modified. DNA polymerases may have an intrinsic strand displacement activity, especially reverse transcriptases to denature secondary RNA structures. A polymerase having nucleotide strand displacement activity may be used for the elongation.

As DNA polymerases, especially reverse transcriptases, can displace a DNA oligonucleotide from a template strand of RNA at least as good as dissolving secondary or tertiary structure, the hybridization of the oligonucleotide has to be enhanced in order to stop strand displacement of the reverse transcriptase. This can be achieved by using modifications to the oligonucleotide itself or by using additives that either stabilize the hybridization of the oligonucleotide or that stop the reverse transcriptase. Modifications to the oligonucleotides that reduce or inhibit the strand displacement activity of the reverse transcriptase are for instance 2' fluoro nucleosides [15], PNAs [16, see FIG. 2; 17], ZNAs [18, 19], G-Clamps (U.S. Pat. No. 6,335,439, a cytosine analogue capable of Clamp Binding to Guanine) or LNAs (US 2003/0092905; U.S. Pat. No. 7,084,125) [20, 21]. These modifications in general increase the melting temperature of the oligonucleotide, by increasing the local hybridization energy of the oligonucleotide to the template RNA strand. Some also stiffen the sugar phosphate backbone further inhibiting strand displacement by the reverse transcriptase.

Alternatively or in addition, the hybridization of the oligo to the RNA template can be altered by using different additives that bind or intercalate to the nucleic acids. For instance, ethidiumbromide, SybrGreen (U.S. Pat. Nos. 5,436,134; 5,658,751; 6,569,627) or acricidine can be used. Other compounds that can bind to dsNA are actinomycin D and analogues [22]. However they potentially also stabilize RNA secondary structure.

Therefore, it is preferred that such intercalators or additives specifically bind to RNA:DNA hybrids. Examples are aminoglycosides of the Neomycin family (Neomycin, Ribostamycin, Paromomycin and Framycetin [23]). Additives that alter the hybridization properties of the oligonucleotide can also be covalently included into the oligonucleotide structure [23].

The hybridization energy and kinetics can be changed to inhibit the strand displacement by the reverse transcriptase by the addition of nucleic acid binding proteins such as single stranded binding protein such as TtH SSB [24] or Tth RecA [25].

It will be apparent to those skilled in the art that those additives are just examples and any other compound, base modification or enzyme leading to an increased hybridization of the oligonucleotide to RNA can be used to increase the Tm and hence inhibit strand displacement.

The increase in the Tm should be strong enough to prevent a displacement of any one of the 5' end nucleotides of the primer region annealed to the template by an elongating polymerase. In particular, the inventive Tm increase prevents displacement of the $3^{rd}$, $2^{nd}$ and/or $1^{st}$ nucleotide downstream to the 5' end of the primer region.

In certain embodiments of the invention the strand displacement needs to be stopped right at the first 5' nucleotide of the downstream primer, especially when the cDNA fragments are ligated to each other or to a linker as described below. The strand displacement of an oligonucleotide is reduced or inhibited by using nucleotide modifications that increase the Tm or stiffen the sugar phosphate backbone of oligonucleotide, by e.g. including 2' fluoro nucleosides LNAs, PNAs, ZNAs or PNAs or by using intercallators or additives that specifically bind to nucleic acids such as Ethidiumbromid, Sybr gold, SybrGreen, preferably intercalators that are specific for RNA:DNA hybrids.

Therefore it is preferred that the binding of the oligonucleotide primers are specifically Tm enhanced at their 5' ends to prevent the elongating polymerase from displacing them. Such modifications include but are not limited to LNAs, PNAs, ZNAs, acridine or fluorophores.

Oligonucleotides with an increased Tm at their 5' end such as LNA-modified oligonucleotides enable a stop right at the start of the next primer. It is within the scope of the invention to combine the strand displacement stop by using the LNA-modified oligos together with the displacement synthesis deficient mutants such as Y64A M-MLV or F61W HIV or any other reverse transcriptase with impaired displacement synthesis as well as lowering the reaction temperature and using different additives to increase the binding of oligonucleotides to the RNA.

Preferably C and/or G nucleotides are modified. Even unmodified these nucleotides have a higher Tm than A or T due to increased hydrogen bridge formation when complementary annealed. In preferred embodiments the oligonucleotide primer and/or oligonucleotide stopper comprises at least one, at least 2, at least 3, at least 4, at least 5, at least 6 modified nucleotides being selected from G or C. These modified nucleotides are preferably at the 5' end of the primer sequence as mentioned above.

Most efficient strand displacement stop is achieved by G or C bases as they increase the local Tm of the primer or stopper. Hence semi-random primers or stoppers (hexamers, heptamers, octamers, nonamers, etc.) containing at least two, more preferably three or more Gs or Cs or a combination of Gs and Cs. It is most preferred if these Gs or Cs are modified to increase the local melting temperature, as is the case when using LNA modified bases. It is most preferred that at least 1, at least 2 or at least 3 LNA modified bases are used at the 5' end of the primer. Therefore, it is preferred that at least two, at least 3 modified nucleotides are used optionally chosen from G or C.

Several methods and means exist to ensure that the elongation reaction is stopped when the elongation reaction reaches the position of an oligonucleotide stopper or further or additional primer annealed to the template. This stopping is also referred to as a prevention of strand displacement herein. Strand displacement is a particular problem for reverse transcription due to increased or high strand displacement activities of reverse transcriptases. The inventive step of inhibiting the reverse transcriptase to strand displace the cDNA of an already copied RNA portion ensures that any portion of an RNA molecule that already got copied is not copied again. Therefore, no copied portion of the RNA gets overrepresented in the cDNA library synthesized. This inhibition of strand displacement can be achieved through different means, such as decreasing the reaction temperature, using a reverse transcriptase without strand displacement activity, increasing the melting temperature or the hybridization energy of the primer:RNA hybrid or increasing the rigidity of the RNA or primer or stabilizing the helix. In practice, usually a combination of these means is selected to achieve optimal reaction conditions without strand displacement. A person skilled in the art is well enabled to select suitable parameters as described herein or known in the art to suit a particular template and reaction conditions.

One option is to modify the reaction temperature. In general, a reaction temperature above 37° C. is favored during RT for better dissolving secondary structures in the RNA template that leads to a more efficient displacement synthesis. In one embodiment stopping of strand displacement of the primer is achieved by decreasing the reaction temperature. Reaction temperatures below 37° C. and down to 4° C. are used to reduce strand displacement. It is preferred that the polymerization during RT is carried out between 20° C. to 37° C. However, even at these low reaction temperatures the strand displacement stop will not be complete when reverse transcripases are used that have strand displacement activity and/or a simple stopper oligonucleotide is used that has no modifications that alter its melting temperature.

In one embodiment instead of or in addition to decreasing the reaction temperature to achieve a better stop of the elongation at said position of a further primer or a stopper (and reduce strand displacement) reverse transcriptases that are deficient in strand displacement such as the Y64A M-MLV mutant [12] or the F61W (Phe61-Trp) HIV mutant [13, 14] can be used. Strand displacement deficient mutants are able to displace the next primer or stopper for up to 3 nts when unmodified. It is within the scope of the invention to combine the strand displacement stop by decreasing the reaction temperature with the usage of displacement synthesis deficient mutants such as Y64A M-MLV or F61W HIV or any other reverse transcriptase with impaired displacement synthesis.

A drawback of decreasing the reaction temperature during the RT or using a reverse transcriptase that has a reduced or impaired strand displacement activity is that the reverse transcriptase will have difficulties reading through regions of RNA secondary structure. The more stable the secondary structure is the less likely it is that this portion of the RNA gets copied into cDNA. This means that though no part of one RNA molecule gets copied more than once parts of the RNA that form a secondary structure will not be copied. This means that some parts of the RNA will be underrepresented in the cDNA library produced.

Therefore, in a preferred embodiment a reverse transcriptase is used that has strand displacement activity and/or the reverse transcription is carried out at elevated temperatures that sufficiently dissolve secondary RNA structure. Under these conditions every portion of the RNA is accessible to the reverse transcriptase. However as RNA:RNA hybrids are generally more stable than RNA:DNA hybrids, also the cDNA copy can be again strand displaced if no further modifications are used. Therefore, in preferred embodiments the reverse transcription is carried out under conditions that do not allow for secondary or tertiary structure formation of the RNA template (RNA:RNA hybrids) or under conditions that allow for these secondary structures to be strand displaced by the reverse transcriptase, while at the same time the primer extension product (cDNA copy) cannot be displaced.

Increasing the concentration of monovalent counter-ions also will stabilize the hybrid (but also the RNA secondary structure), as it has been reported for HIV-RT that at 75 mM KCl the strand displacement activity is impaired though not inhibited [26, 27]. In a preferred embodiment the concentration of monovalent positive ions is preferably selected from at least 20 mM, at least 30 mM, at least 40 mM, at least 50 mM, at least 60 mM, at least 70 mM. Similar concentrations can be independently selected for single negatively charged ions.

The reverse transcriptase used during the elongation reaction may be a viral reverse transcriptase, and may be selected from the group consisting of AMV RT (and mutants thereof such as Thermoscript RT), MMLV RT (and mutants thereof including but not limited to Superscript I, II or III, Maxima RT, RevertAid, RevertAid Premium, Omniscript, GoScript), HIV RT, RSV RT, EIAV RT, RAV2 RT, Tth DNA polymerase, C. hydrogenoformans DNA polymerase, Avian Sarcoma Leukosis Virus (ASLV) and RNase H—mutants thereof. Mixtures of any of these reverse transcriptases may be used. In particular, mixtures of viral RT enzymes may be used, such as mixtures of MMLV and ASLV, and/or their RNase H reduced or RNase H minus analogs may be used. In any of these methods and compositions, two or more reverse transcriptases may be used, including any reverse transcriptase as described above.

It is within the scope of the invention to combine the strand displacement stop by decreasing the reaction temperature with the usage of displacement synthesis deficient mutants such as Y64A MMLV or F61W HIV or any other reverse transcriptase with impaired displacement synthesis and increasing the Tm of the oligonucleotide to the RNA.

In any of these methods and compositions a thermostable DNA polymerase may also be used, although with regard to RNA stability and hybridization kinetics of the primers this is not recommended in all situations.

Especially for but not limited to optimal representation in a randomly primed cDNA library the random primers may be present in a concentration from 50 nM to 100 µM, and more preferred at about 2.5 µM but can also be at least 300 nM. In preferred embodiments the ratio (w/w) of primer to template nucleic acids is between 5:1 and 1:1000, preferably between 2:1 and 1:500, preferably between 1:1 and 1:300, preferably between 1:2 and 1:250, preferably between 1:5 and 1:150, preferably between 1:10 and 1:100, preferably between 1:12 and 1:50. The molar ratio of primer to template nucleic acids may be between 1,000:1 to 5,000,000:1, preferably between 5,000:1 to 1,000,000:1, between 10,000:1 to 500,000:1, or between 20,000:1 to 300,000:1. In one example, using 150 ng of mRNA starting material and assuming an mRNA length of 500-5000 nt this would mean primers added at 2.5 µM final concentration are added in a molar excess of 1:280,000-1:28,000. In preferred embodiments the molar or (w/w) ratio of primers to stoppers is between 2:1 and 1:10, preferably between 1:1 and 1:5, especially about 1:1.

However lowering the oligo concentration is possible e.g.: using 34 ng of mRNA starting material and assuming an mRNA length of 500-5000 nt this would mean primers added at 300 nM final concentration are added in a molar ratio of 1:33-1:3.3, with the template being in a molar excess. A preferred reduced nucleotide concentration during the polymerization reaction can help to reduce strand displacement and spurious second strand synthesis of the polymerase. In preferred embodiments the molar or (w/w) ratio of primers to stoppers is between 2:1 and 1:10, preferably between 1:1 and 1:5, especially about 1:1.

When mRNA is reverse transcribed an oligo dT primer can be added to better cover also the poly A tail of the mRNA. Optionally, the addition of the oligo dT primer can be omitted as it is part of the random primer mix, although in a preferred embodiment to guarantee equal representation of the mRNA it should be added. The length of oligo dT can vary from 8 bases to 27 bases, but preferably an 25 nt long oligo dT primer is used. Other types of primers with different composition can be used in place of oligo dT. Examples of such compositions include, but are not limited to, oligo dT where the 3' base is A, or C, or G (anchored dT). Furthermore, other sequences or moieties that can base pair with poly A sequences of mRNA can also be used. An example, without limitation, is deoxy uridine, (dU).

The oligo(dT) may consist essentially of between about 12 and about 25 dT residues, and may be an anchored oligo(dT) molecule containing a terminal non-T nucleotide. The oligo(dT) may be oligo(dT) 18-25 nt long or anchored equivalents thereof.

The oligo(dT) may be present in a concentration of between about 20 nM and about 1 µM, most preferably 500 nM are being used. The random primers may be between 5 and 15 nucleotides long, and may be random hexamers with at least 3 LNAs or at least three 2' Fluoro-modified bases at the 5' site to efficiently stop strand displacement.

An additional feature is that depending on the concentration of the random primer the average length of the product nucleic acids can be influenced. By increasing the concentration of the random primers the resulting elongated product size can be decreased. The desired fragment size depends on the subsequent application. If the desired amplified nucleic acid portions should be below 300 nt (as is currently desired for next generation sequencing) the random primer concentrations should range from 125 nM to 350 nM final concentration.

According to the methods of the invention the concentration of oligo dT can be 44 nM to 750 nM, for example, or intermediate values. It is evident to those skilled in the art that various ratios of random primers and oligo dT can be used.

When mRNA is under investigation, preferably mRNA enriched RNA samples should be used. Several methods for mRNA enrichment are well documented and known to those skilled in the art. The most commonly used is poly A+ enrichment either by oligodT paramagnetic beads or oligodT cellulose [28]. A number of commercial kits for mRNA enrichment are available. Alternatively mRNA can be enriched by Terminator treatment (Epicentre). Additionally, several companies offer commercially available mRNAs from a number of organisms and tissues.

The concentration and combinations of modified-random primers and oligo dT used in this invention provides efficient and representative conversion of mRNA sequences into cDNA. This method provides superior and non-biased conversion of mRNA sequences into cDNA regardless of the distance from the 3' end of the mRNA. Additionally it guarantees that any RNA molecule is reverse transcribed only once by inhibiting the strand displacement of the reverse transcriptase.

The present invention therefore relates to methods of increasing equal representation of mRNA, and more particularly, to increasing the accuracy of quantification of gene expression. Thus, the present invention provides improved cDNA synthesis useful in gene discovery, genomic research, diagnostics and identification of differentially expressed genes and identification of genes of importance to disease.

In another embodiment oligonucleotide stoppers can be used to specifically block the reverse transcription of unwanted such as but not limited to high abundant or ribosomal transcripts during the reverse transcription process. This step can be used to suppress specific templates to generate a normalized mixture of products. A practical use is in suppressing abundant mRNA to generate a normalized cDNA library. Oligonucleotide stoppers that are used to suppress a template, i.e. are not used to generate a well-defined elongation product are referred herein as blocking oligonucleotides or blockers. Blocking oligonucleotides are known from GB 2293238, US 2002/0076767 A1, U.S. Pat. No. 6,391,592 B1, WO 99/61661, WO 02/086155, U.S. Pat. No. 5,849,497, WO 2009/019008 and can be employed according to the present invention. Preferably such blocking oligonucleotides would be highly specific for those transcripts which should be prevented from being reverse transcribed, hence are preferentially longer than 15 nt. Longer oligonucleotides have a higher Tm, hence are harder to be displaced by the reverse transcriptase. In a preferred embodiment the blocking oligonucleotides also have an increased Tm at the 5' end by the introduction of modifications such as but not limited to LNAs, ZNAs, PNAs or acridine. These blocking oligonucleotides will need to be blocked at the 3' end to prevent them from being extended. Such blockages include but are not limited to C3, C6, C12 spacers or dideoxynucleotides. The blocking oligonucleotides should preferentially be designed against a sequence that is located near the 3' end of the RNA, but upstream of the poly A tail.

It is within the scope of the invention to combine the inventive methods by using the above described blocking oligos together with the strand displacement synthesis deficient mutants such as Y64A M-MLV or F61W HIV or any other reverse transcriptase with impaired displacement synthesis as well as lowering the reaction temperature and using different additives to increase the binding of oligonucleotides to the RNA.

Alternatively, if the sequences of the high abundant transcripts are not known, hence specific blocking oligos cannot be designed, the strand displacement stop can also be used for library normalization. A driver library would be synthesized with SDS oligonucleotides (preferentially such with increased local Tm at the 5' end such as LNA, PNA or ZNA modified oligonucleotides).

With a terminal transferase dideoxynucleotides can be added to those amplified nucleic acid portions in order to generate the blocking oligos. This library can then be hybridized to a tester template sample. High abundant transcripts will have an advantage and the single stranded amplified nucleic acid portion from the driver will be faster and more efficient in hybridizing to the corresponding template. Product synthesis can then be initiated using a primer, such as oligodT primer for mRNA, and since most of the high abundant transcripts are hybridized to blocking oligonucleotides, the low abundant transcripts have a far greater chance of being reverse transcribed. If a template switch or oligo capping protocol is also used, the resulting cDNA of the low abundant transcripts can even be inserted into a PCR reaction with the primers corresponding to the oligo-dT primer and the template switch or oligo capping nucleotide. Alternatively selective terminal tagging (US 2009/0227009 A1) can be used to tag the 3' end of the newly synthesized cDNA. Since high abundant transcripts are most likely to have never reached full length due to the blocking oligonucleotides only low abundant transcripts will be amplified in a PCR with primers corresponding to the oligodT primer and the 3' cDNA tag.

Alternatively, if the 3' end of the cDNA is not tagged, an oligo-dT primer with a double stranded T7 RNA polymerase promoter could be used to prime the RT reaction of the normalized cDNA libraries and a linear amplification by in vitro transcription can be used.

Therefore a blocking oligonucleotide can be added to the elongation to stop unwanted sequence portions of a template molecule to be elongated. Pre-selected sequences of the unwanted template sequence are selected for use as blockers.

In preferred embodiments of the invention the template nucleic acid, e.g. the RNA template, is single stranded. In particular it is possible that the obtained template nucleic acid lacks a complementary strand over at least 30% of its length and/or lacks a complementary strand of at least 100 nucleotides in length, preferably lacks a complementary nucleic acid over its entire length. The inventive method also encompasses separating possibly existing complementary strands from the inventive template nucleic acid strand and introducing the so purified template nucleic acid without a complementary strand to the inventive method.

In particular preferred, the inventive one or more primers and one or more stoppers bind to the template strand—and particularly not to a complementary strand.

In a further aspect the present invention relates to the use of the above described methods for generating one or more template nucleic acids to generate a sequence library comprising a mixture of amplified nucleic acid portions of said template nucleic acids. Preferably, the amplified nucleic acid portions provide overlapping sequence portions of the template. This can e.g. be facilitated by using a multitude of different primers that generate various elongated products that in turn are used as amplified nucleic acid portions for the library.

The invention further provides a kit for generating amplified nucleic acid portions of a template nucleic acid as described herein or for generating a sequence library as described herein comprising a DNA polymerase, random oligonucleotide primers which comprise a modification that increases the Tm and random oligonucleotide stoppers that are unsuitable for nucleotide extension and comprise a modification that increases the Tm, optionally further one or more of reaction buffers comprising $Mn^{2+}$ or $Mg^{2+}$, a ligase, preferably DNA ligase or RNA ligase with DNA ligating activity, a crowding agent suitable for ligase reactions, like PEG. The ligase may also be a RNA ligase, especially a RNA ligase that has DNA ligating activity such as T4 RNA ligase 2. Crowding agents are inert molecules that can be used in high concentrations and can be used to mimic the effects of macromolecular crowding inside a cell. Examples are PEG (polyethylene glycol), PVP (polyvinylpyrrolidone), trehalose, ficoll and dextran. Crowding agents are e.g. disclosed in U.S. Pat. No. 5,554,730 or 8,017,339. The kit may alternatively comprise DNA polymerase and a ligase and optionally any further compound mentioned above.

Further kits of the invention that are suitable for generating amplified nucleic acid portions of a template nucleic acid comprise or contain a) random oligonucleotide primers which comprise a modification that increases the Tm and b) random oligonucleotide stoppers that are unsuitable for nucleotide extension and comprise a modification that increases the Tm. The kit may further comprise one or more of reaction buffers comprising $Mn^{2+}$ or $Mg^{2+}$, a ligase, a crowding agent, such as PEG. The kit may also further comprise a DNA polymerase and/or a ligase.

Kits for use in accordance with the invention may also comprise a carrier means, such as a box or carton, having in close confinement therein one or more container means, such as vials, tubes, bottles and the like. The kit may comprise (in the same or separate containers) one or more of the following: one or more reverse transcriptases, suitable buffers, one or more nucleotides especially dNTPs, and/or one or more primers (e.g., oligo(dT, starters, stoppers, reverse complements, PCR primers) for reverse transcription and subsequent PCR reactions. The kits encompassed by this aspect of the present invention may further comprise additional reagents and compounds necessary for carrying out nucleic acid reverse transcription protocols according to the invention, such as oligodT beads or streptavidin coupled beads. Furthermore, the primers or stoppers may be immobilized on a solid surface.

The present invention is further illustrated in the following figures and examples, without being limited to these embodiments of the invention.

Discussion of the Drawings Figures

FIG. 1: Schematic representation of the principle problem the invention seeks to solve.

a) Primers P1, P2 up to Pn are hybridized to a template RNA. Primer P2 has hybridized to a more upstream (5') position of the template RNA than primer P1 and more generally primer Pn has hybridized to a more upstream position on the template RNA than primer P(n−1). Or in other words, primer P1 has hybridized to a more downstream (3') position on the template than P2 and more generally P(n−1) has hybridized to a more downstream position on the template RNA than Pn. Extension of each primer is initiated by a reverse transcriptase. b) When the reverse transcriptase while polymerizing the extension product of P2 reaches a primer P3, primer P3 and its extension product get strand displaced by the reverse transcriptase that continues to extend the primer P2 extension product. The same is true for the extension product of P1 that displaces primer P2 and its extension product. c) Therefore, when all extension products are finished, one cDNA copy of the template sequence between P1 and P2 is present, but two cDNA copies between P2 and P3 are present. This phenomenon leads to an overrepresentation of the 5' ends of RNA that is primed multiple times, as it happens during standard reverse transcription using random primers such as random hexamers. More generally speaking, when n primers have hybridized and were extended by the polymerase to the 5' end of the template RNA, then the 5' end of the RNA will be represented n times while the 3' end of the RNA will be represented only once.

Figure 2:
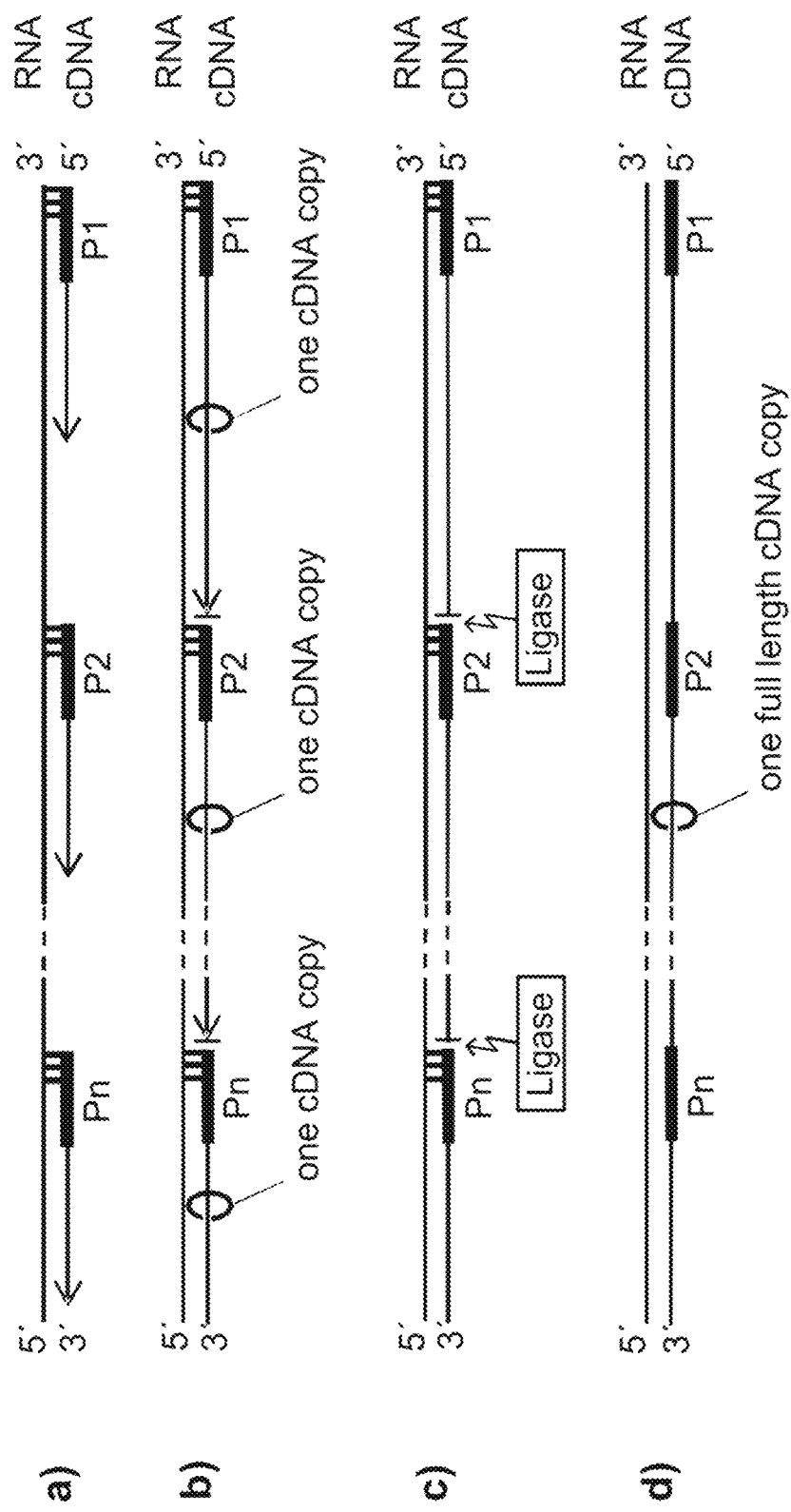
FIG. 2 is a schematic representation of one embodiment of the invention to create a 5'-3' balanced cDNA library and full length cDNA.

FIG. 2: Schematic representation of one embodiment of the invention to create a 5'-3' balanced cDNA library and full length cDNA.

a) The hybridization of primers P1, P2 to Pn is reinforced by using e.g.: locked nucleic acids (LNAs) to inhibit the strand displacement activity of the reverse transcriptase. Here three modifications on the very 5' end of the primers are used. b) Now upon extending a primer that lies more downstream on the template RNA the reverse transcriptase cannot displace the primer that has hybridized to a more upstream position on the template. Therefore, each portion of the RNA is only represented once as cDNA. In that manner no overrepresentation of RNA 5' ends will occur. c) When full length cDNA is desired the individual primer extension products are ligated to yield d) one full length cDNA copy of the template RNA.

FIG. 3: Schematic representation of creating a linker tagged short cDNA library.

For many downstream analyses of cDNA libraries a universal linker sequence is needed either on one or both ends of the cDNA, to for instance amplify the library or start a sequencing reaction. Here the preparation of a library that has two linkers is shown. a) Primers P1, P2 to Pn have a 5' universal linker sequence extension (L1). In addition stopper oligos S1, S2 to Sm are used that have a 3' universal linker sequence extension (L2). The stopper oligos are also modified (e.g. LNAs) so they also cannot be displaced by the reverse transcriptase. b) In a second reaction step the 3' end of the extension product is ligated to the 5' end of the stopper oligo. In that manner a cDNA library is created that has two linker sequences (L1, L2) available in order to c) amplify the whole library during e.g. a subsequent PCR.

FIG. 4: Schematic representation of creating a linker tagged short cDNA library using an alternative stopper oligo concept.

As the error rate that is introduced into the cDNA library through a mis-hybridization of the stopper oligo sequence is greater than if this portion would have been transcribed by a polymerase, an alternative stopper oligo concept is shown. a) Here in comparison to FIG. 3 the stopper oligo Sm is extended on its 5' side by an L2rc (reverse complement) sequence. This L2rc is hybridized with L2 to form an adapter. b) Again as in FIG. 3 the reverse transcriptase is extending the primers Pn until they reach the stopper oligos Sm. During ligation the extension product is now ligated to the L2 strand of the adapter. In this manner again a cDNA library is created that has two linker sequences (L1, L2) present on its ends. Here, however, no stopper oligo sequence is introduced. Therefore, when sequencing from the L2 side of the library no ambiguity towards the identity of the first nucleotides is introduced by a potential mis-hybridization of the stopper oligo. c) Finally, a PCR follows.

FIG. 5: Schematic representation of creating a linker tagged short cDNA library using an alternative stopper oligo concept.

In an alternative concept starter and oligo form a heterodimer over a complementary sequence in their respective linker sequences L1 and L2. Sequence gaps will be reduced since at any stop there is also a polymerization initiated by the starter. a) Starter/stopper hybrids are extended at the 3' end of the starter sequence P1 to Pn until the next starter/stopper hybrid is encountered. Stopper oligos S1, S2 to Sm have a 3' universal linker sequence extension (L2) which is in a hybrid with the L1 sequence of the starter. It is sufficient if the stopper is modified to prevent strand displacement although in an alternative subset of such starter/stopper hybrids shown in FIG. 8e the modification needs to be located at the starter if the L2 sequence has no 5' sequence extension that is hybridizing to the template nucleic acid. b) In a second reaction step the 3' end of the extension product is ligated to the 5' end of the stopper oligo. In that manner a cDNA library is created that has two linker sequences (L1, L2) available in order to c) amplify the whole library during e.g. a subsequent PCR.

Figure 6:
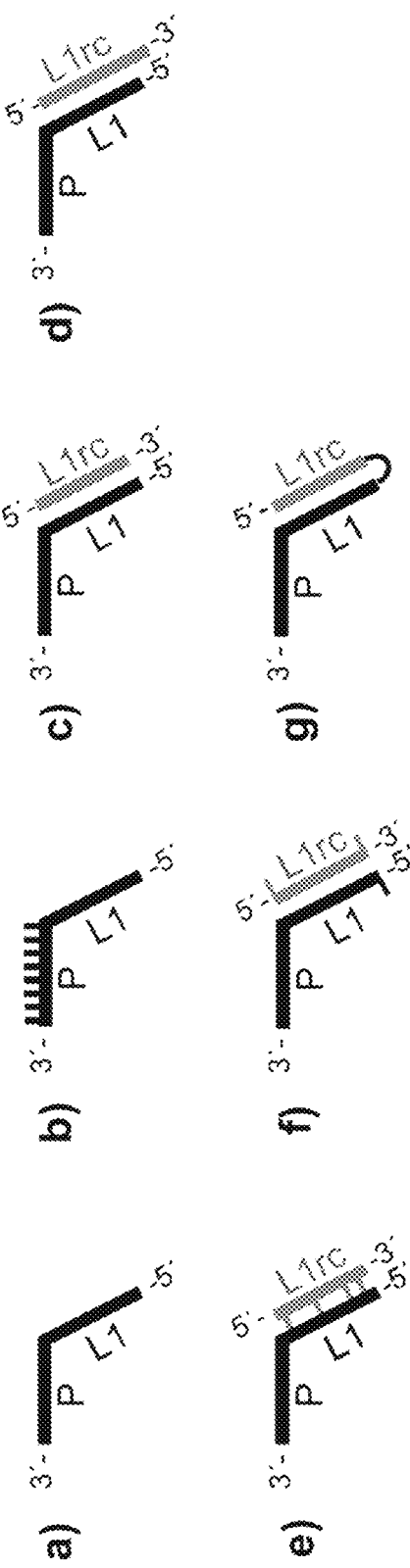
FIG. 6 is a schematic representation of preferred primer modifications.

FIG. 6: Schematic representation of preferred primer modifications.

Depicted are primer modifications that are preferred. These modifications can also be combined. a) General structure of priming oligo, with primer and linker sequence. When generating a randomly primed cDNA library the primer sequence is typically a random sequence such as, for instance, a random hexamer. b) The primer sequence part contains modified nucleotides. The modification reduces or inhibits the strand displacement activity of the reverse transcriptase. c) A reverse complement (L1rc) is introduced that inhibits the L1 sequence part of the oligo to participate in the hybridization to the template RNA strand. Therefore, a bias toward the L1 sequence is blocked. d) To prevent the reverse transcriptase from associating with the linker adaptors and hence lowering the efficiency of reverse transcription a 3' overhang is used at the 3' end of L1rc. e) The L1rc sequence is modified to increase hybridization strength to the L1 sequence to further reduce the likelihood of bias in the library towards the L1 sequence. f) Blocking of all ends that do not participate in polymerase extension or ligase reaction. g) The 5' end of the L1 sequence and the 3' end of the L1rc sequence are connected through a covalent bridge, e.g. a Cn spacer or a hairpin sequence.

Figure 7:
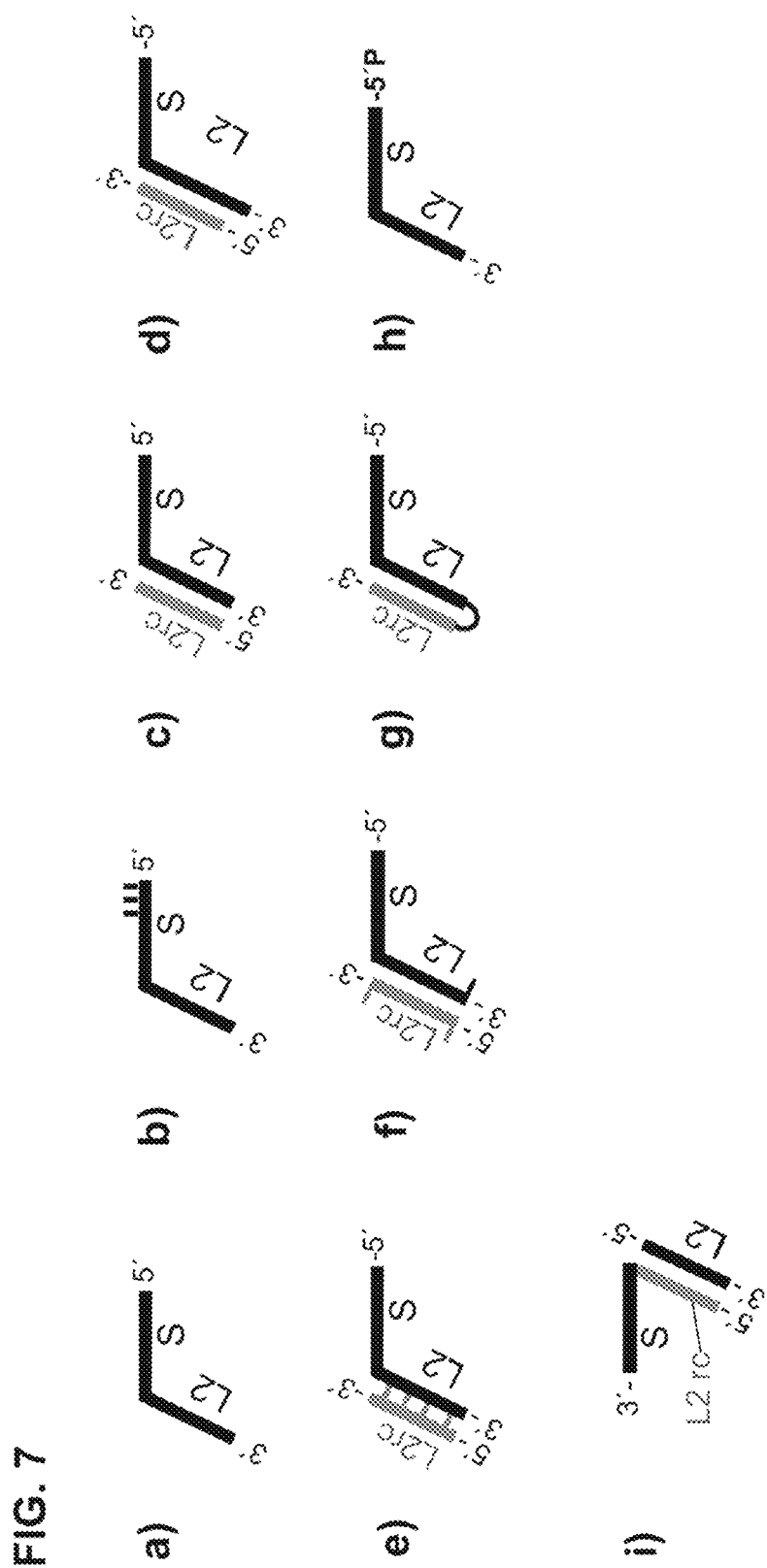
FIG. 7 is a schematic representation of preferred oligo stopper modifications.

FIG. 7: Schematic representation of preferred oligo stopper modifications.

Depicted are stopper oligonucleotide modifications that are preferred. These modifications can also be combined. a) General structure of stopper oligo, with stopper and linker sequence. The stopper sequence is typically a random sequence such as for instance a random nonamer. b) The stopper sequence part contains modified nucleotides. The modification reduces or inhibits the strand displacement activity of the reverse transcriptase. c) A reverse complement (L2rc) is introduced that inhibits the L2 sequence part of the oligo to participate in the hybridization to the template RNA strand. Therefore, a bias toward the L2 sequence is blocked. d) To prevent the reverse transcriptase from associating with the linker adaptors and hence lowering the efficiency of reverse transcription, a 3' overhang is used at the 3' end of L2. e) The L2rc sequence is modified to increase hybridization strength to the L2 sequence to further reduce the likelihood of bias in the library towards the L2 sequence. f) Blocking of all ends that do not participate in polymerase extension or ligase reaction. g) The 5' end of the L1 sequence and the 3' end of the L1rc sequence are connected through a covalent bridge, e.g. a Cn spacer or a hairpin sequence. h) The 5' end of the stopper oligo is phosphorylated to be able to act as a donor in the ligation reaction. Alternatively the 5' end is adenlyated. i) Depicts the general structure of the stopper oligo used in the alternative oligo stopper concept in FIG. 4. The 5' end of the L2 sequence can be phosphorylated to be able to act as a donor in a ligation reaction, or alternatively adenylated.

FIG. 8: Schematic representation of the most preferred oligo starter and stopper combinations.

Depicted are preferred starter/stopper combinations. Starters and stopper oligonucleotide contain a complementary (e.g. 14 nt) sequence stretch in their linker sequence, which allows them to hybridize with each other therefore making the addition of additional reverse complements obsolete. Starter and stopper designs from FIGS. 6 and 7 are still valid. The starter is blocked by a 5' OH. The stopper oligonucleotide is optionally blocked at the 3' end by e.g. dideoxynucleotides, dioxynucleotides, spacers or inverted nucleotides. a) General structure of a stopper oligonucleotide in a hybrid with a starter oligonucleotide. Oligos are hybridized with each over e.g. a 14 nt stretch. Both starter and stopper oligonucleotides hybridize to the template strand together. Starters and stoppers can have a hybridization base to the template nucleic acid of different lengths. The stopper oligonucleotide can have a longer or shorter hybrisation base compared to the starter and vice versa. b)

both the starter and stopper are modified to inhibit strand displacement by the polymerase. c) here only the 5' end nucleotides of the stopper are modified. This is enough as the polymerase needs to be inhibited to strand displace only at the 5' end of the stopper. In effect a single modification (such as LNA or 2'Fluoro) is enough. d) shows also a modification of the starter, as not all starters that are extended might be in a hybrid with a stopper that also has hybridized to the template. e) when the sequence of the stopper that hybridizes to the template is reduced to 0 then the starter needs to also provide for the stop and therefore a modification that stops strand displacement is desirable. f) The L1 and L2 sequence can have a part that does not hybridize. g) shows an alternative configuration where the linker sequences have portions that hybridize to each other and portions that don't. h) shows a configuration where the starter and stopper oligo are linked together forming in effect one oligonucleotide. Of course many more starter and stopper variations exist that can be used by someone skilled in the art.

Figure 9:
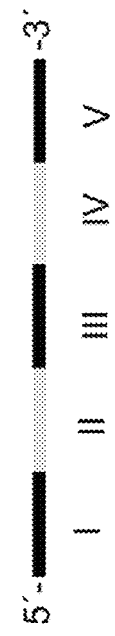
FIG. 9 is a schematic representation of the oligo starter and stopper structures.
Figure 9:
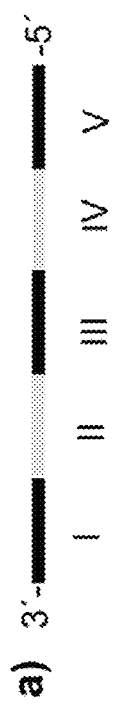

FIG. 9: Schematic representation of the oligo starter and stopper structures.

a) Starter oligonucleotides are depicted from 3' to 5' and b) stopper oligonucleotides are depicted from 5' to 3'. The starter (a) consist of (I) a priming sequence such as a random hexamer sequence binding to the template strand on the 3' side which preferably is modified to protect against strand displacement.

(II) Optionally a barcode sequence can be located 5' of the random priming sequence. The barcode sequence preferentially consists of 3-9 nucleotides, which allow a unique and specific identification of the library. Such barcodes enable for instance to mix libraries from different samples and sequence them together on a flow cell. After the sequencing run the reads can be demultiplexed according to the specific barcode.

(III) The sequencing primer binding site. This is the sequence used to bind the sequencing primer during sequencing.

(IV) a sequence for bridge amplification (e.g.: for Illumina NGS sequencing) or for attachment to a solid surface such as beads (e.g. for SOLiD NGS sequencing).

(V) a sequence tag which provides a hybridization basis for starter and stopper oligo.

A minimal starter can consist of a random priming part (I) and a sequencing primer binding site (III), in which case a reverse complement as described in FIG. 6c-g is preferred to prevent the sequencing primer part from taking place in the hybridization process. Alternatively a starter can consist of a random priming part (I) and a sequencing primer binding site(III), and a hybridization basis with the stopper, whereby III and V could be completely or partially identical e.g. if the sequencing primer binding site is complementary to a sequence part III in the stopper region. Alternatively starters can consist of I, II, III, and V, whereby again III and V could be completely or partially identical e.g. if the sequencing primer binding site is complementary to a sequence part III in the stopper region. Starters can also consist of I, II, III, IV, and V.

If a starter with a shorter linker sequence is used sequences corresponding to sequence primer binding site (III), barcodes (II) and/or surface attachment (IV) can be introduced during amplification of the generated libraries e.g.: during a PCR reaction by introducing these sequence tags with the PCR primers.

Stopper oligonucleotides are depicted from 5' to 3' in b). The stopper (b) may consist of (I) a random sequence binding to the template on the 5' side which is preferably modified to protect against strand displacement.

(II) Optionally a barcode sequence or a sequence that is reverse complementary to the barcode sequence on the starter(II) can be located 3' of the random priming sequence. The barcode sequence preferentially consists of 3-9 nucleotides, which allow a unique and specific identification of the library.

(III) The sequencing primer binding site.

(IV) Optionally a sequence tag for surface attachment for bridge amplification (e.g.: for Illumina NGS sequencing) or for attachment to a solid surface such as beads (e.g. for SOLiD NGS sequencing) as well as (V) a sequence tag which provides a hybridization basis for starter and stopper oligo. A minimal stopper can consist of a random priming part (I) and a sequencing primer binding site(III), in which case a reverse complement as described in FIG. 7c-g is preferred to prevent the sequencing primer part from taking place in the hybridization process. Alternatively a stopper can consist of a random priming part (I) and a sequencing primer binding site(III), and a hybridization basis with the starter, whereby III and V could be completely or partially identical e.g.: if the sequencing primer binding site is complementary to a sequence part III in the stopper region. In an alternative embodiment this minimal stopper may also lack the random sequence as shown in FIG. 4 or 8e. Alternatively stoppers can consist of I, II, III, and V, whereby again III and V could be completely or partially identical e.g.: if the sequencing primer binding site is complementary to a sequence part III in the stopper region. Starters can also consist of I, II, III, IV, and V.

If a stopper with a shorter linker sequence is used sequences corresponding to sequence primer binding site (III), barcodes (II) and/or surface attachment (IV) can be introduced during amplification of the generated libraries e.g.: during a PCR reaction by introducing these sequence tags with the PCR primers.

Figure 10:
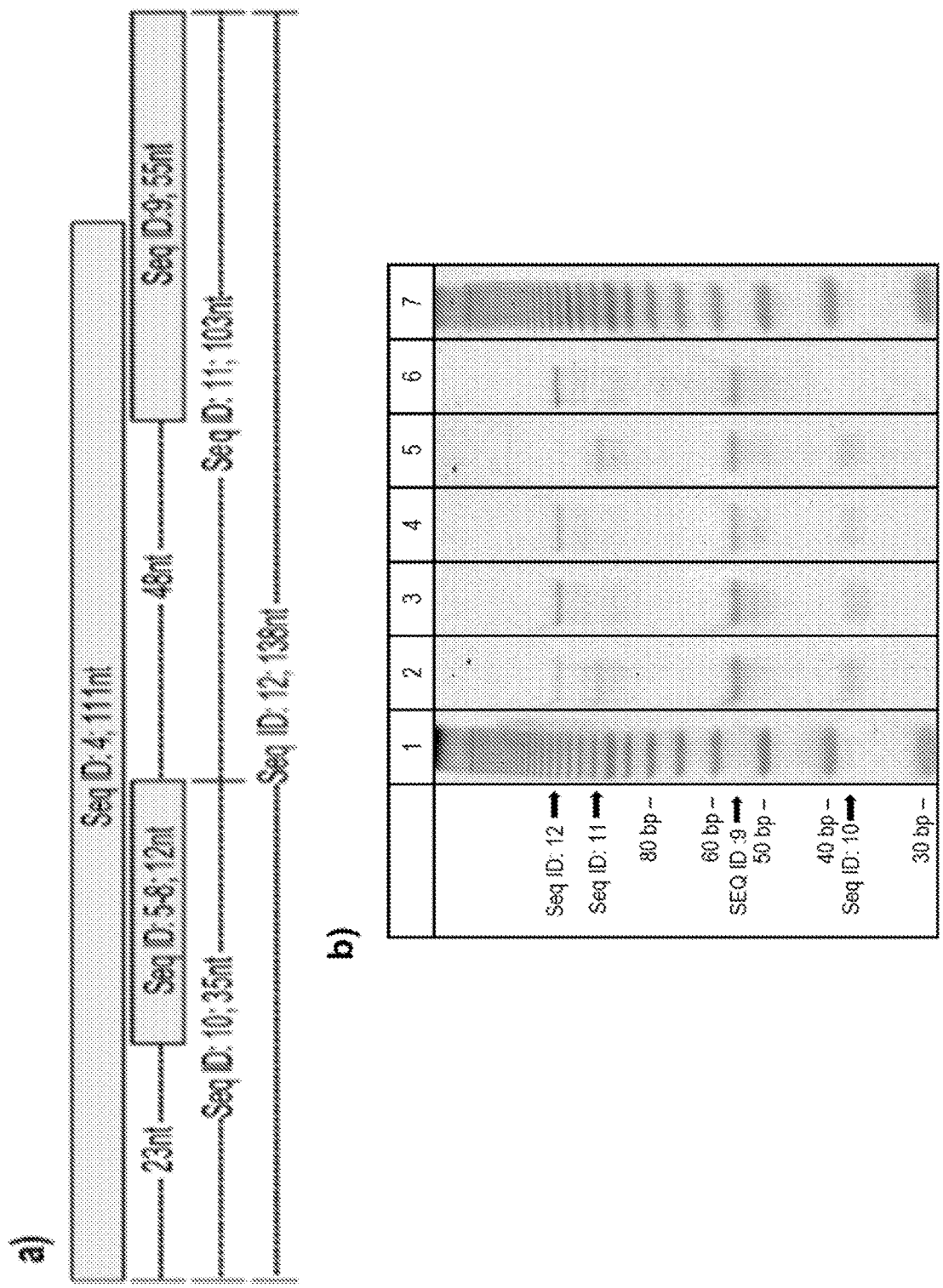
FIG. 10 shows stopping of strand displacement during reverse transcription.

FIG. 10: Stopping of strand displacement during reverse transcription.

a) Illustrates the assay set up for determining the ability of modified or non-modified oligonucleotides (Seq ID No: 5-8) to inhibit the strand displacement activity of the reverse transcriptases which are used in addition to an oligo dT primer (Seq ID No: 9). The extension of the strand displacement stop oligo is 35 nt (Seq ID No:10), the strand displacement stop product is 103 nt (Seq ID No:11) and the full length cDNA product is 138 nt (Seq ID No:12).

b) Shows the results of Example 1.

Figure 11:
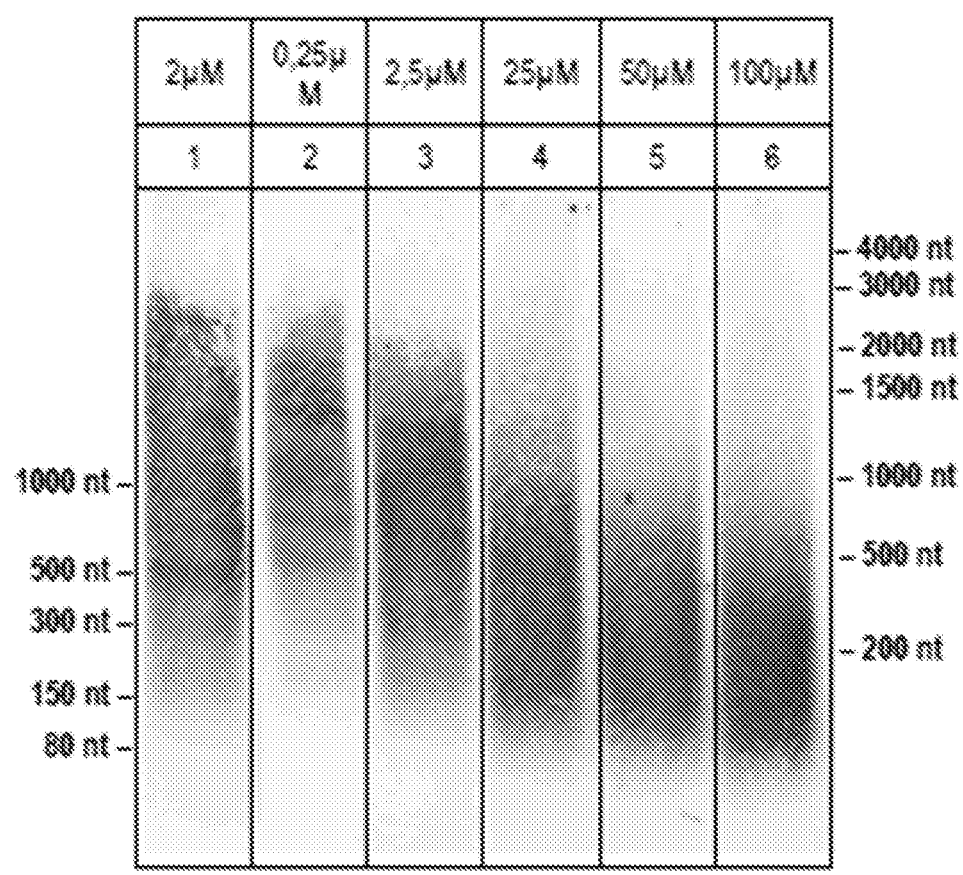
FIG. 11 is an imaging depicting regulation of cDNA fragment size by amount of stop oligos inserted into the RT.

FIG. 11: Regulation of cDNA fragment size by amount of stop oligos inserted into the RT.

Shows the results of Example 2. cDNA fragments are obtained by random primed cDNA synthesis with or without strand displacement stop oligos and analyzed on an immunoblot.

Figure 12:
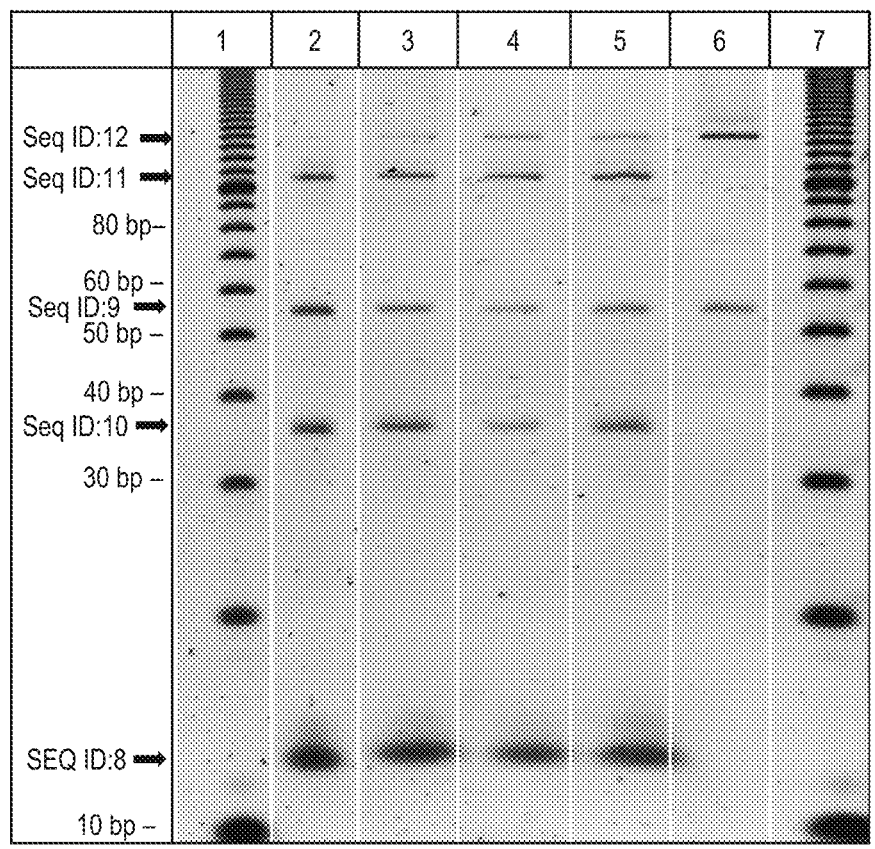
FIG. 12 is an image depicting stopping strand displacement during reverse transcription plus ligation of the cDNA fragments to a full length product

FIG. 12: Stopping strand displacement during reverse transcription plus ligation of the cDNA fragments to a full length product Shows the results of Example 3. Here the strand displacement stop is induced by an oligo with 3 LNAs at the 5' end and the subsequent ligation of the resulting 2 DNA fragments (35 nt, Seq ID No: 10 and 103 nt, Seq ID No: 11) to the 138 nt full-length product (Seq ID No: 12) using either T4 DNA ligase (lane 3), T4 RNA ligase 2 truncated (lane 5) or a combination of both (lane 4). In lane 6 a control reaction omitting the SDS oligo is shown. In lane 2 the SDS oligo was added, but no ligase was added to the ligation reaction.

Figure 13:
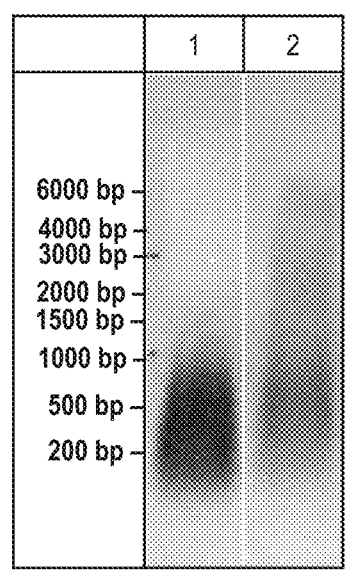
FIG. 13 is an image depicting validation of SDS/Ligation on mRNA.

FIG. 13: Validation of SDS/Ligation on mRNA.

Shows the results of Example 4. The immunoblot shows a significant length increase if the short strand displacement stop cDNA fragments are ligated using T4 DNA ligase.

Figure 14:
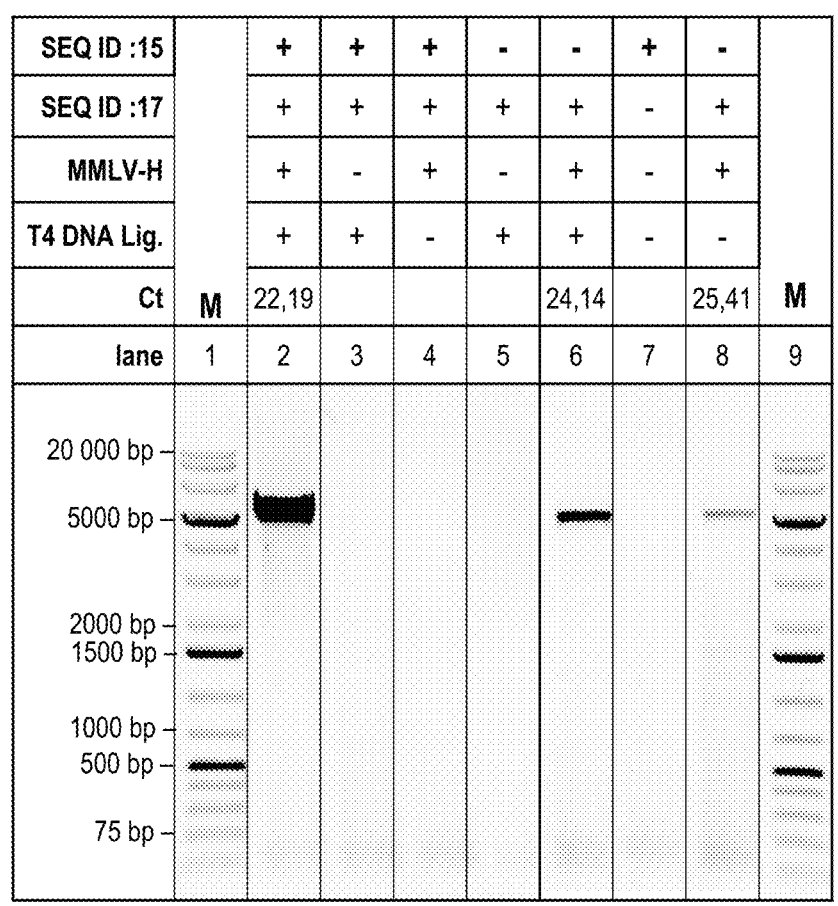
FIG. 14 is a table and image depicting strand displacement stop during reverse transcription plus ligation of the cDNA fragments to a full length product results in more product of a selected cDNA.

FIG. 14: Strand displacement stop during reverse transcription plus ligation of the cDNA fragments to a full length product results in more product of a selected cDNA.

The results of Example 5 are illustrated. qPCR results of a 5 kb fragment from Dync1 h1 (NM 030238) amplified from different reverse transcriptions (RTs) are shown. An RT using a SDS oligo (Seq ID No: 15) and an oligo dT primer (Seq ID No: 17) or oligo dT primer (Seq ID No: 17) by itself was performed. T4 DNA ligase was added or in control reactions not added and a qPCR was performed on the resulting cDNAs. Only in case of ligation the SDS oligos were able to produce the 5 kb fragment in a PCR reaction (primers Seq ID No:18 and Seq ID No:19). There is more PCR product in reactions performed on SDS/Ligation cDNA (i.e.: more cDNA template available) than in a regular oligo dT primed cDNA (compare lane 2 to lane 6 and 8, respectively).

FIG. 15: cDNA length comparison of SDS/ligation vs oligo dT priming on a 15 kb cDNA.

FIG. 15 shows the results of Example 6, a qPCR assay designed to judge the cDNA length generated in an RT reaction. Triangles: oligodT primed reverse transcription, squares: random hexamer primed transcription, circles: inventive transcription with stopped elongation at downstream primers plus ligation.

Figure 16:
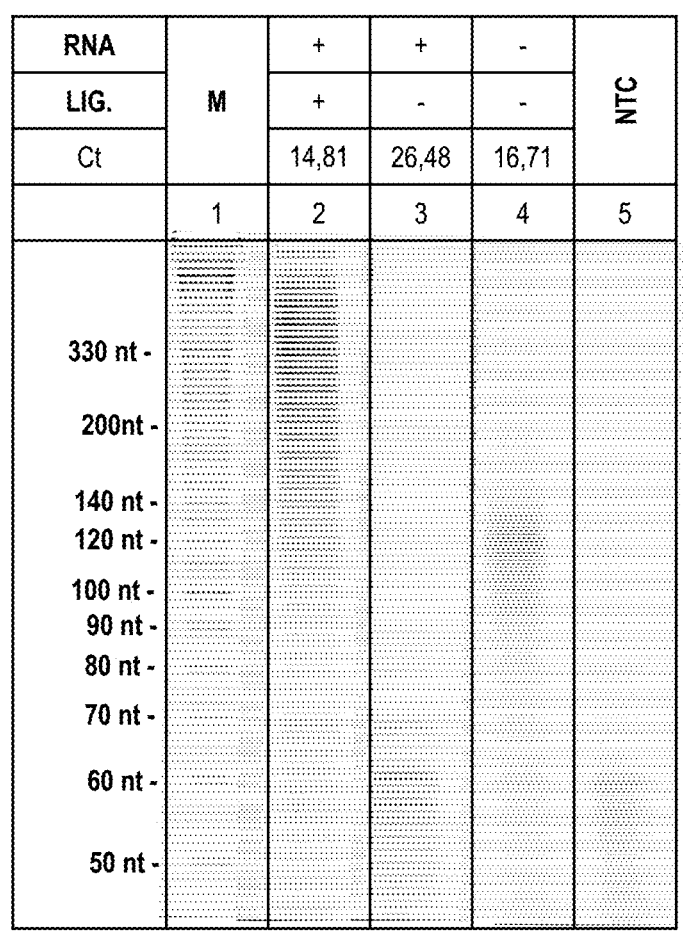
FIG. 16 is a table and image depicting generation of a di-tagged DNA libray from mRNA.

FIG. 16: Generation of a di-tagged DNA library from mRNA.

Shows a DNA library generated using the SDS/ligation approach (see lane 2), whereas the no ligation control stays empty (see lane 3). Without the addition of RNA template some linker-linker byproducts can be generated since the oligo dT primer will then serve as a template for hybridization (see lane 4). PCR no template controls are clean (see lane 5).

Figure 17:
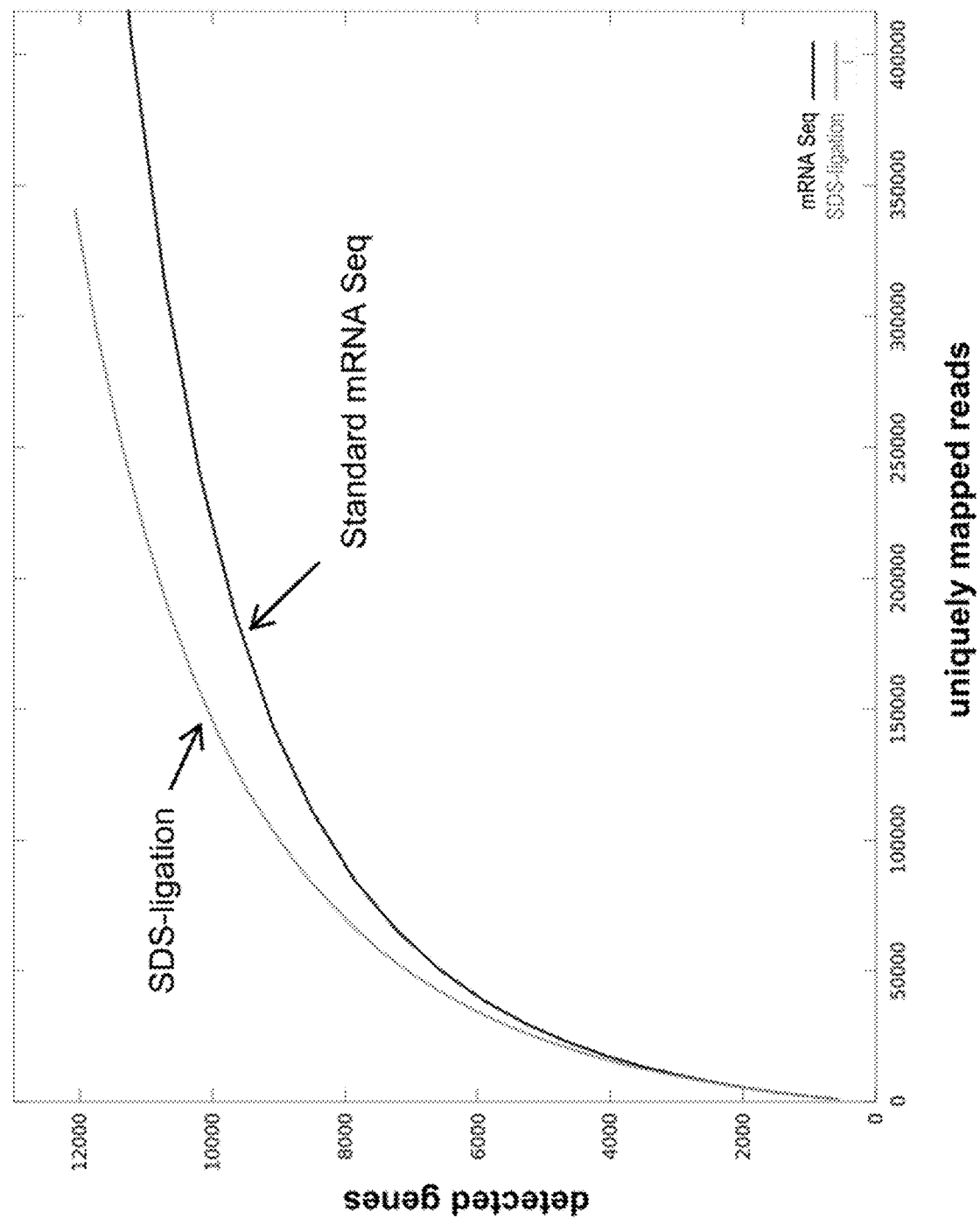
FIG. 17 is a graph depicting a discovery blot comparing a library preparation using the new strand displacement stop and ligation protocol (SDS-ligation) with a standard mRNA Seq protocol (TRUSEQ) RNA sample prep kit, Catalog # RS-930-20 01).

FIG. 17: Discovery blot comparing a library preparation using the new strand displacement stop and ligation protocol (SDS-ligation) with a standard mRNA Seq protocol (TruSeq™ RNA sample prep kit, Catalog # RS-930-20 01). Both were sequenced on an Illumina GAIIx sequencer (single read, 72 bp). The X-axis shows the number of reads that uniquely mapped to the annotated genome vs the number of genes discovered on the Y-axis. The comparison of the graphs shows that the SDS-ligation protocol is feasible and actually needs less reads to detect the same amount of genes than the standard protocol.

ABBREVIATIONS qPCR: quantitative polymerase chain reaction
SDS: strand displacement stop
RT: reverse transcription or reverse transcriptase (depending on the context)
LNA: locked nucleic acid
PNA: peptide nucleic acid
rc: reverse complement
Tm: melting temperature
SNP: single nucleotide polymorphism
CGH: comparative genomic hybridization
CNV: copy-number variation
PTO: phosphorothioate bond
Phos: phosphorylation Definitions Starter: Starters are molecules that can prime a templated polymerase extension reaction. Usually starters have an oligonucleotide sequence commonly referred to as a primer. Starters can have 5' sequence extensions such as universal linker sequences described in FIGS. 6, 7, 8 and 9.

EXAMPLES

Example 1: Strand Displacement Stop of Reverse Transcriptases Using LNA Modified Oligonucleotides

```
Sequences:
SEQ ID No. 1: 5'-
GCTAATACGACTCACTATAGTTGTCACCAGCATCCC-3'

SEQ ID No. 2: 5'-
TTTTTTTTTTTTTTTTTTTTTTTTTCGAATGGGCCGCAGGA-3'

SEQ ID No. 3: 5'-
GCTAATACGACTCACTATAGTTGTCACCAGCATCCCTAGACCCGTACAG

TGCCCACTCCCCTTCCCAGTTTCCGACTGTCCCCGGCCTCCTGCGGCC

CATTCGAAAAAAAAAAAAAAAAAAAAAAAAAAA-3'

SEQ ID No. 4: 5'-
guugucaccagcaucccuagacccguacagugcccacuccccuuccccag uuuccgacugucccccggccuccugcggcccauucgaaaaaaaaaaaaa aaaaaaaaaaaaaa-3' (RNA)

SEQ ID No. 5: (Phos)(5'-+GGGCACTGTACG-3')

SEQ ID No. 6: (Phos)(5'-GGGCACTGTACG-3')

SEQ ID No. 7: (Phos)(5'-G*GGCACTGTAC*G-3')

SEQ ID No. 8: (Phos)(5'-+G+GGCACTGTAC*G-3')

SEQ ID No. 9: 5'-
A*CGGAGCCTATCTATATGTTCTTGACATTTTTTTTTTTTTTTTTT

TTTTT*T*V-3'

SEQ ID No. 10: 5'-
GGGCACTGTACGGGTCTAGGGATGCTGGTGACAAC-3'

SEQ ID No. 11: 5'-
A*CGGAGCCTATCTATATGTTCTTGACATTTTTTTTTTTTTTTTTTT

TTTTTTCGAATGGGCCGCAGGAGGCCGGGGACAGTCGGAAACTGGGAAG

GGGAGT-3'

SEQ ID No. 12: 5'-
A*CGGAGCCTATCTATATGTTCTTGACATTTTTTTTTTTTTTTTTTT

TTTTTTCGAATGGGCCGCAGGAGGCCGGGGACAGTCGGAAACTGGGAAG

GGGAGTGGGCACTGTAC-GGGTCTAGGGATGCTGGTGACAAC-3'

An asterix "*" denotes a phosphorothioate (PTO)
bond, a plus "+" in front of a nucleotide denotes
a locked nucleic acid (LNA). "Phos" denotes a
phosphorylation,
```

To investigate the feasibility of inhibiting the strand displacement activity of the reverse transcriptase under conditions that enable primer annealing and cDNA polymerization, a proof of concept experiment is shown. For an outline of the assay setup see FIG. 10*a*, and for results see FIG. 10*b*.

Generation of In Vitro Transcribed 111 nt RNA Template: A 75 bp fragment of GAPDH (NC_000072, 48 nt-122 nt) was PCR amplified with primers containing either a T7 promoter sequence (Seq ID No: 1) or a T27 tail (Seq ID No:

2). The resulting PCR product (SEQ ID No: 3) served as template for T7 in vitro transcription using Epicentre's AmpliScribe Flash T7 transcription kit. The in vitro transcribed 111 nt RNA (Seq ID No: 4) served as template for the strand displacement stop assay during reverse transcription.

cDNA Synthesis:

First-strand cDNA synthesis was carried out using MMLV-H from Promega (250 U/20 µl reaction). The strand displacement assay setup is depicted in FIG. 10a. Primers for cDNA synthesis, LNA-modified oligos (1 LNA-G (Seq ID No: 5), unmodified oligos (Seq ID No: 6), PTO-modified oligos (Seq ID No: 7), 3 LNA-G oligos (Seq ID No: 8) or oligo dT (Seq ID No: 9) were ordered from either Microsynth AG (Balgach Switzerland), or Eurogentec (Seraing, Belgium). 800 ng of in vitro transcribed 111 nt RNA (Seq ID No: 4) and oligos (Seq ID No: 5-9; 50 nM oligodT primer SEQ ID No:9 and 1.5 µM SEQ ID No: 5-8) were heated to 70° C. for 2 min with all required components (except for the reverse transcriptase) including: buffer (50 mM Bis-Tris-Methane pH 7.9, 75 mM KCl, 4 mM MgCl2, 0.6 M Trehalose and 7.5% glycerol), 0.5 mM each dNTP, 10 mM dithiothreitol (DTT), and slowly annealed by decreasing the temperature to 40° C. with 30 sec holds at every 2° C. decrease. At 40° C. 250 units of reverse transcriptase were added and the temperature was slowly raised to 45° C. with 1 min holds at each 1° C. increase followed by a 30 minute incubation at 46° C. Following first-strand synthesis, samples were heated to 95° C. for 5 min in 0.1 M NaOH, neutralized with equal molarities of HCl and purified by EtOH precipitation. After washing with 75% EtOH the pellets were dissolved in 5 µl 10 mM Tris, pH 8.0 and mixed with an equal volume of 100% formamide loading buffer, denatured at 95° C. for 2 min, cooled on ice and resolved by electrophoresis in a 15% acrylamide/7M urea.

Results are shown in FIG. 10b.

In the different lanes the second downstream oligo (that has hybridized to a more upstream portion of the template) was varied (Seq ID Nos: 5-8) using an oligo that had one LNA modification (Seq ID No: 5) in lane 2, no modification (Seq ID No: 6) in lane 3, one PTO (Seq ID No: 7) in lane 4 or three LNA modifications (Seq ID No: 8) in lane 5 and no second oligo in lane 6. Lane 1 and 7 show a size marker (10 bp marker, Invitrogen). It can be seen that the unmodified (lane 3) or the PTO modified (lane 4) oligonucleotides are completely strand displaced by MMLV-H reverse transcriptase since only the full length product (Seq ID No: 12) at 138 nt is visible and no strand displacement stop product at 103 nts (Seq ID No: 11). The second oligo has also been extended to 35 nts ((Seq ID No: 10) and hence the 5' end of the 111 nt RNA is represented twice (once in from of the full length product (138 nt) and once by the 35 nt extension product of the second oligo). Introducing 1 LNA at the 5' sequence of the 2nd oligo already causes some stop of strand displacement (138 nt and 103 nt product are visible), while 3 LNAs lead to an almost complete stop of strand displacement (no more 138 nt product, just the 103 nt strand displacement stop product (Seq ID No: 11).

Example 2: cDNA Fragment Size Regulation

This example shows that the size of a cDNA library that is generated from mRNA can be regulated by the concentration of a random primer that stops an elongation reaction. For results see FIG. 11.

RNA Isolation and Purification:

Total RNA from mouse liver was isolated using PeqLab Gold columns in combination with acidic phenol extraction (PeqLab, PEQLAB Biotechnologie GMBH, D-91052 Erlangen) according to manufacturer's recommendation. The amount of RNA was measured by optical absorbance at 260 nm and checked for integrity on a formaldehyde agarose gel or an Agilent Bioanalyzer.

Terminator Treatment of Total RNA to Enrich for mRNAs:

2-5 µg of total RNA was treated with Terminator™ 5'-Phosphate-Dependent Exonuclease (Epicentre Biotechnologies, Madison, Wis. 53713), according to manufacturer's instructions.

cDNA Synthesis and Immunoblotting:

cDNA synthesis was carried out in 20 µl reactions with 50 mM Tris-HCl (pH 8.3 at 25° C.), 75 mM KCl, 3 mM MgCl2, 10 mM DTT, 0.75 mM dNTPs with Digoxigenin-11-2'-deoxy-uridine-5'-triphosphate, alkali-stable. 135 ng of mRNA (terminator treated total RNA) was incubated at 70° C. for 2 min in the presence of primers and all the reaction components apart from the enzyme and the dNTPs. A slow annealing program was chosen with 30 seconds holds at the following temperatures: 45° C., 43° C., 40° C., 38° C., 35° C., 30° C., 28° C. and 1 minute at 25° C. 200 U of MMLV-H, point mutant (Promega) and dNTPs were added per 20 µl reaction and incubated for 2 min each at the following temperatures: 25° C., 28° C., 30° C., and 35° C. before a final extension at 37° C. for 10 min. Following first-strand synthesis, samples were heated to 55° C. for 15 min in 0.1M NaOH, neutralized with equal molarities of HCl, purified by EtOH precipitation. cDNA fragments were separated by formaldehyde agarose gel electrophoresis (0.8%), transferred to Zeta-Probe GT Genomic Blotting Membranes (BioRAD) by electroblotting for 1 h at 50V according to "Mini Trans-BlotR Electrophoretic Transfer Cell" instruction manual (BioRAD), then crosslinked and by UV-light.

Membranes were equilibrated in 1× blocking buffer (100 mM maleic acid/150 mM NaCl, pH 7.5) for 5 min, before blocking unspecific binding sites of the membrane in blocking solution (5% milk in blocking buffer) for 30 min. Anti Fab antibodies diluted 1:2,000 (Anti-Digoxigenin-AP FAB fragments, Roche cat #11 093 274 910); 30 ml blocking solution were incubated for 30 min at room temperature under shaking. Membranes were washed 2× for 15 min in 1× blocking buffer and then equilibrated for 5 min in 1× staining buffer (0.1 M Tris-HCl, pH 9.5 (20° C.), 0.1 M NaCl). Staining in staining solution (BCIP®/NBT Liquid Substrate, 800 µl à 30 ml 1× staining buffer) was done at room temperature (in the dark) overnight without shaking.

The results can be seen in FIG. 11.

In lane 1-5 an oligo (SDS-oligo) with three LNAs on its 5' side (SEQ ID No: 13: (Phos)(5'-+N+N+NNNN-3')) was used in increasing concentrations (Lane 2: 0.25 µM; lane 3: 2.5 µM; lane 4: 25 µM, lane 5: 50 µM and lane 6: 100 µM). In Lane 1 a control reaction with a non-modified random hexamer (SEQ ID No: 14: (Phos)(5'-NNNNNN-3')) at 2 µM is shown. By increasing the amount of SDS oligos the size of the generated cDNA fragments can be decreased.

Example 3: Ligation Using an Artificial Template

The example shows that an extension product of a more upstream primer (P1) can be stopped by a more downstream primer (P2) that has three LNA modifications on its 5' end and that the extension product of the upstream primer (P1) can by ligated to the downstream primer (P2) when all are in a hybrid with the template. For an overview of the sequences involved see FIG. 10a. For results see FIG. 12.

Reverse transcription was carried out using oligos, template and conditions as described in Example 1.

After the RT the samples were ethanol precipitated and inserted into a 15 µl ligation reaction with 1 mM HCC, 20% PEG-8000, 30 mM Tris-HCl (pH 7.8 at 25° C.), 10 mM MgCl$_2$, 10 mM DTT, 1 mM ATP and 1.5 µl of T4 DNA ligase (1-3 Weiss units/µl, Promega) and/or 1 µl of T4 RNA ligase 2 truncated (10 units/µl, NEB) and incubated 2 h at 37° C. Unligated small fragments and remaining oligos were removed by PEG precipitation. Therefore the volume of the reaction was increased to obtain 11.5% final PEG concentration and 2 µl of linear polyacrylamide (10 mg/ml) were added as carrier. Reactions were thoroughly vortexed before centrifugation at 20,000×g for 15 min at 18° C. The pellet was washed 2× in 75% EtOH, dissolved in 5 µl 10 mM Tris (pH 8.0), mixed with an equal volume of 100% formamide loading buffer, denatured at 95° C. for 2 min, cooled on ice and loaded onto a 15% acrylamide/7M urea gel. The results can be seen in FIG. 12. In lane 6 the artificial RNA was reverse transcribed using only an oligo dT primer (SEQ ID No: 9). When an SDS oligo (SEQ ID No: 8) is added in addition to the oligo dT primer (SEQ ID No: 9), there is a complete stop of strand displacement as seen by the appearance of a 103 nt SDS product (Seq ID No: 11, see FIG. 12, lane 2). Furthermore a 35 nt SDS oligo extension product (Seq ID No: 10) is generated. T4 DNA ligase (FIG. 12, lane 3) or T4 RNA ligase 2, truncated (FIG. 12, lane 5) as well as a combination of both enzymes (FIG. 12, lane 4) were tested for their efficiency to ligate the two cDNA fragments in an RNA hybrid. T4 RNA ligase 2, truncated, is deficient of an adenylation function and hence can only ligate already adenylated oligos i.e.: oligos that were previously adenylated by T4 DNA ligase in the hybrid. T4 RNA ligase 1 was not used due to the preferred ligation of single stranded molecules which would then also result in ligation of non-hybridized oligos preferentially to the RNA template. As can be seen in lane 3-5 the stopped products (103 nt, Seq ID No: 11) and the SDS oligo extension product (35 nt, Seq ID No: 10) can be ligated in the RNA hybrid, resulting in a full-length 138 nt cDNA (Seq ID No: 12).

Example 4: Ligation of cDNA Fragments Synthesized from Poly A-mRNA

The example shows that by ligating short cDNA fragments that were generated by the inventive method a size shift occurs on the immunoblot, indicating that longer cDNA was created by the ligation process. For methods see Example 2 and 3. For results see FIG. 13. Poly A selected mRNA (mouse liver polyA+mRNA, Stratagene) was used as a template. Short cDNA fragments (see FIG. 13, lane 1, fragments between 100-700 nt) that were generated using combination of oligo dT primer (SEQ ID No: 9) and a random dodecamer with 3 LNA modified nucleotides (SEQ ID No: 15: (Phos)(5'-+G+G+GHHHNNNNNN-3')) were ligated in the RNA hybrid using T4 DNA ligase, which results in long (full-length) cDNAs even longer than 6,000 nts (see FIG. 13, lane 2).

Example 5: In a Gene-Specific qPCR the SDS/Ligation Reverse Transcription Yields More Product than a Regular oligodT Primed RT A gene-specific PCR was carried in a 20 µl reaction containing 1 µl cDNA (synthesized from 800 ng total RNA, dissolved in 42 µl 10 mM Tris, pH 8.0 after purification), 50 mM Tris-Cl pH 9.2, 16 mM ammonium sulfate, 0.1% Tween 20, and 5.1 mM MgCl$_2$, 1.5M Betaine, 1.3% DMSO, 0.5×SYBRGreen I, 0.2 mM of each dNTP, 0.3 µM of each primer (SEQ ID No: 18: 5'-CTGGATGAATGGCTT-GAGTGT-3' and SEQ ID No: 19: 5'-GCAACTCCACGCT-CATAGAAG-3', primers designed for NM 030238), 0.8 units KlenTaq AC polymerase and 0.2 units Pfu polymerase. Samples were denatured at 95.8° C. for 15 sec, and cycled 20 times at 95.8° C. for 15 sec, 55° C. for 30 sec, 74° C. for 20 min (ramp speed at ABI9700: 50%). Subsequently, 19 cycles at 95.8° C. for 15 sec, 58° C. for 30 sec, 74° C. for 20 min (ramp speed at ABI9700: 10%) with a final extension step at 72° C. for 3 min followed. PCR products were purified using silica column and were loaded onto a 0.7% agarose gel. Results are shown in FIG. 14. Lane 8 shows the 5096 bp PCR product generated from a cDNA synthesized with an oligo dT primer (Seq ID NO: 17: 5'-G*GCGTTTTTTTTTTTTTTTTTTT*V-3'). As a control oligodT primed cDNA was also subjected to the ligation protocol that is usually applied for the strand displacement stop oligos (see lane 6). When Seq ID No: 15 (SDS oligos) and Seq ID No: 17 (oligo dT) were used to prime the RT reaction followed by a ligation protocol as described in Example 3, the amount of PCR product generated from such a cDNA was even more than from a regular oligo dT primed cDNA (compare FIG. 14, lane 2 to lane 6 and 8, respectively). This can be explained by the SDS oligos preventing secondary structure formation due to hybridization, whereas those secondary structures lead to premature polymerization stop events if only an oligo dT primer is used. With the SDS/ligation protocol the RT is started at multiple places and the resulting cDNA fragments are then ligated to give full-length cDNA products or in this case the selected 5 kb fragment from a randomly chosen specific transcript. Without ligation no PCR product is generated in the subsequent PCR of cDNA synthesized with SDS oligos (see lane 4). This clearly shows that the strand displacement was actually stopped and the generated cDNA fragments were not connected, hence no PCR product can be obtained, since there is no template containing both PCR primer binding sites. Lane 3, 5, and 7 are controls were no reverse transcriptase was added to the RT reaction, hence showing there was no genomic DNA contamination and that the SDS oligos do not result in any unspecific background.

Example 6: Long Transcripts are More Efficiently Reverse Transcribed Using a SDS/Ligation RT Protocol A long transcript was chosen (ubiquitin protein ligase E3 component n-recognin 4; Ubr4; NM_001160319) and 200 bp amplicons were designed along the cDNA. Amplicons were spaced approximately 2 kb apart from each other (primers Seq ID No: 20-29).

SEQ ID NO. 20: 5'-CCTTCCAGGAGGAGTTCATGCCAGT-3'

SEQ ID NO. 21: 5'-CACACGGAGAGATGAATGAGGGGAGA-3'

SEQ ID NO. 22: 5'-GCCTTCATGGCTGTGTGCATTGA-3'

SEQ ID NO. 23: 5'-CATCCTGCCCTGTAGAAAGTCCTCTTG-3'

SEQ ID NO. 24: 5'-CCAGTGTCACAAGTGCAGGTCCATC-3'

SEQ ID NO. 25: 5'-GCGGTCAGCTTTGTCCAGAAGTGTGT-3'

SEQ ID NO. 26: 5'-GTAAGATGGTGGATGGGGTGGGTGT-3'

SEQ ID NO. 27: 5'-TCGCTCTGAAATGCTGACTCCTTCA-3'

SEQ ID NO. 28: 5'-ACCCAGGTTCTACTGCGTCCTGTCC-3'

SEQ ID NO. 29: 5'-CCTCCAGGGCTGTCACGTTCTTCTT-3'

The delta Ct between the more 3' amplicons and the most 5' amplicon (complementary to the 3' end of the mRNA, close to the poly A tail) is used to calculate the fold difference (according to Pfaffl [34]) and hence shows the relative decrease in cDNA generated over the length of the mRNA template. Oligo dT (Seq ID No: 17) primed cDNA was compared to a cDNA primed with Seq ID: 15 and Seq ID No: 14 followed by a ligation of the resulting cDNA fragments in the RNA hybrid. Each of the reaction was performed in triplicates and the means are depicted in FIG. 15. Circles depict values that were measured using SDS-oligos (dashed line); Squares when random hexamers were used (continuous line) and triangles when oligo dT was used (dotted-dashed line). Only the SDS/ligation protocol guarantees a more equal cDNA synthesis over the length of the transcript having an almost perfect 3' to 5' ratio of 1.

Oligo dT primed cDNA (triangles, dotted-dashed line) shows a steady decline in cDNA generated over the length of the 15 kb mRNA. Only approximately 10% of the originally started cDNA synthesis reaches 6 kb. Random priming without strand displacement leads to an overrepresentation of the 5' end of the mRNA (squares, continuous line).

Example 7: Generation of a Di-Tagged DNA Library from mRNA 0.11 µM Biotin tagged oligo dT primer (SEQ ID NO. 30: (Biotin-TEG)(5'-TTTTTTTTTTTTTTTTTTTTTTTTTTT-3'), 2.5 µM tagged primer (SEQ ID NO. 31: (C12-Spacer) (5'-TCCCTACACGACGCTCTTCCGATCTGACTG+G+G+GNNN-3')+2.5 µM reverse complement to the primer tag (SEQ ID NO. 32: (C3-Spacer)(5'-CAGTCAGATCG+GAA+GA+GC+GTC+GT+GTAGGGA-3')(C3-Spacer)), 5 µM tagged stopper (SEQ ID NO. 33: (Phos)(5'-+G+G+GHHNNNNAGATCGGAAGAGCGGTTCAGCAGGA-3') (C3Spacer))+5 µM reverse complement to the stopper tag (SEQ ID NO. 34: (C12-spacer)(5'-TCCT+GCT+GAACC+GCTCTTCC+GATC-deoxyT-3'), deoxyT denotes a 3' blocked deoxyT), were hybridized to 150 ng of polyA+ mRNA (BioCat Heidelberg, Germany) hybridized in Tris, pH 7.0 (70° C., 1 min, then slowly cooled on ice). Assuming an mRNA length of 500-5,000 nt this would mean that the starters are added in a molar excess of 1:280,000-1:28,000, whereas the stoppers are added in a molar excess of 1:560,000-1:56,000. The hybridized nucleic acids were then bound (20 min at room temperature) to pre-washed 1.1 µl Streptavidin coated Dynabeads (M-280, 10 mg/ml). Non-hybridized nucleic acids were washed away (4 washes according to the manufacturer's instructions). Afterwards RT buffer was added to a final concentration of 1× (50 mM Tris-HCl (pH 8.3 at 25° C.), 75 mM KCl, 3 mM MgCl$_2$, 10 mM DTT), 0.5 mM dNTPs, 200 Units MMLV-H as well as 8 U of T4 DNA ligase plus 10% PEG and 0.4 µM ATP. The reverse transcription-ligation reaction was performed on beads by heating the reaction slowly raising the temperature (25° C. for 2 min, 28° C. for 1 min, 31° C. for 1 min, 34° C. for 1 min) before incubating for 2 hours at 37° C. Again the beads were washed (4×), before hydrolyzing the RNA (55° C. for 15 min in 0.1 N NaOH). After neutralization with 0.1 N HCl, samples were precipitated, dissolved in 20 µl and 4 µl were then inserted into an Illumina qPCR (primers: SEQ ID NO. 35: 5'-A*ATGATACGGCGACCACCGAGATCTACACT CTTTCCTACACGACGCTCTTCCGATC*T-3' and SEQ ID NO. 36: 5'-C*AAGCAGAAGACGGCATACGAGATC GGTCTCGGCATTCCTGCTGAACCGCTCTTCCGATC* T3'). Results are shown in FIG. 16. A library smear is generated using the SDS/ligation approach (see lane 2), whereas the no ligation control stays empty (see lane 3). Without the addition of RNA template some linker-linker byproducts can be generated since the oligo dT primer will then serve as a template for hybridization (see lane 4). PCR no template controls are clean (see lane 5).

Example 8

SDS-ligation samples were prepared as described in Example 7. For comparison a standard mRNA-Seq library was prepared according to an Illumina library prep protocol (TruSeq™ RNA sample prep kit, Catalog # RS-930-20 01). Both libraries were sent for NGS sequencing on an Illumina GAIIx machine (single read, 72 bp). To compare the performance of both libraries discovery blots were calculated showing the number of detected genes in relation to a given number of reads that mapped uniquely to the annotated genome. The discovery blots are shown in FIG. 17. They show the feasibility of the SDS-ligation protocol that actually outperforms the standard m-RNA Seq library preparation protocol.

Example 9

Di-tagged libraries were prepared from universal human reference RNA (Agilent Technologies, Catalog #740000) spiked in with ERCC RNA spike in control mix (Catalog #4456740) according to the manufacturer's instruction. Two NGS sample preparation methods were used: either ScriptSeq V2 kit (cat # SSV21106, Epicentre, WI) according to the manufacturer's instructions or a sample preparation as described in example 7 with the following modifications: oligodT25 magnetic beads from Dynazyme (taken from the mRNA direct kit Catalog #610-12) were used as well as LNA-N modified starters

```
SEQ ID No. 37: (5Sp9)
(5'-TCCCTACACGACGCTCTTCCGATCTAGC+N+N+NNNN-3')
and stoppers SEQ ID No. 38: (phos)
(5'-+N+N+NNNNNNNNAGATCGGAAGAGCGGTTCAGCAGGA-3')

(C3 spacer).
```

In Table 1 the results of the NGS sequencing run are listed.

TABLE 1

Determination of library strandednes on ERCC spike in transcripts.

| Method | total reads | % ERCCs | % strandedness median |
|---|---|---|---|
| a) SDS_Lig | 43399527 | 1.09% | 100% |
| b) ScriptSeq | 32709274 | 0.85% | 97.52% |

The strandedness (conservation of strand information) was determined for both methods using the ERCC RNA spike in controls. These controls provide an absolute measure of the strandedness since they only exist in one orientation i.e.: there is no antisense. Should a method detect antisense transcripts of the ERCCs it is a direct measure of the inherent error rate of said method. The strandedness is calculated as the median of 1000 reads/ERCC for both methods. The SDS-ligation method showed 100% strand specificity with no reads going into the wrong direction whereas with ScriptSeq the strandedness is determined to be 97.52%.

REFERENCES

[1] Seyfang A, Jin J H. Multiple site-directed mutagenesis of more than 10 sites simultaneously and in a single round. Anal Biochem. 2004 Jan. 15; 324(2):285-91.

[2] Hogrefe H H, Cline J, Youngblood G L, Allen R M. Creating randomized amino acid libraries with the QuikChange Multi Site-Directed Mutagenesis Kit. Biotechniques. 2002 November; 33(5):1158-60, 1162, 1164-5.

[3] Winshell J, Paulson B A, Buelow B D, Champoux J J. Requirements for DNA unpairing during displacement synthesis by HIV-1 reverse transcriptase. J Biol Chem. 2004 Dec. 17; 279(51):52924-33. Epub 2004 Sep. 30.

[4] Bustin S A, Nolan T. Pitfalls of quantitative real-time reverse-transcription polymerase chain reaction. J Biomol Tech. 2004 September; 15(3):155-66. Review.

[5] Lacey H A, Nolan T, Greenwood S L, Glazier J D, Sibley C P. Gestational profile of Na+/H+ exchanger and Cl—/HCO3-anion exchanger mRNA expression in placenta using real-time QPCR. Placenta. 2005 January; 26(1):93-8.

[6] Zhang J, Byrne C D. Differential priming of RNA templates during cDNA synthesis markedly affects both accuracy and reproducibility of quantitative competitive reverse-transcriptase PCR. Biochem J 1999; 337: 231-241.

[7] Feinberg, A. P., and Vogelstein, B. A technique for radiolabeling DNA restriction endonuclease fragments to high specific activity. Analytical Biochemistry, 132: 6-13 (1983).

[8] Feinberg, A. P., and Vogelstein, B. A technique for radiolabeling DNA restriction endonuclease fragments to high specific activity. Addendum. Analytical Biochemistry, 137: 266-7 (1984).

[9] Houldsworth, J., and Chaganti, R. Comparative Genomic Hybridization: an Overview. American Journal of Pathology 145: 1253-1260 (1994).

[10] Gresham, D., Dunham, M. J., and Botstein, D Comparing whole genomes using DNA microarrays. Nature Reviews Genetics 9(4):291-302 (2008).

[11] Metzker M L. Sequencing technologies—the next generation. Nat Rev Genet. 2010 January; 11(1):31-46. Epub 2009 Dec. 8. Review

[12] Paulson B A, Zhang M, Schultz S J, Champoux J J. Substitution of alanine for tyrosine-64 in the fingers subdomain of M-MuLV reverse transcriptase impairs strand displacement synthesis and blocks viral replication in vivo. Virology. 2007 Sep. 30; 366(2):361-76. Epub 2007 May 29.

[13] Fisher T S, Darden T, Prasad V R. Substitutions at Phe61 in the beta3-beta4 hairpin of HIV-1 reverse transcriptase reveal a role for the Fingers subdomain in strand displacement DNA synthesis. J Mol Biol. 2003 Jan. 17; 325(3):443-59.

[14] Fisher, T. S. & Prasad, V. R. (2002). Substitutions of Phe61 located in the vicinity of template 50-overhang influence polymerase fidelity and nucleoside analog sensitivity of HIV-1 reverse transcriptase. J. Biol. Chem. 277, 22345-22352.

[15] Kawasaki, A. M., et al., Uniformly modified 2'-deoxy-2'-fluoro phosphorothioate oligonucleotides as nuclease resistant antisense compounds with high affinity and specificity for RNA targets, Journal of Medicinal Chemistry (1993), 36: 831-841.

[16] Nielsen P E, Egholm M, Berg R H, Buchardt O. Sequence-selective recognition of DNA by strand displacement with a thymine-substituted polyamide. Science. 1991 Dec. 6; 254(5037):1497-500.

[17] Egholm M, Buchardt O, Christensen L, Behrens C, Freier S M, Driver D A, Berg R H, Kim S K, Norden B, Nielsen P E. PNA hybridizes to complementary oligonucleotides obeying the Watson-Crick hydrogen-bonding rules. Nature. 1993 Oct. 7; 365(6446):566-8.

[18] Voirin, E. et al. (2007) Versatile synthesis of oligodeoxyribonucleotide-oligospermine conjugates. Nat Protoc, 2, 1360-1367

[19] Moreau et al. (2009) Zip nucleic acids (ZNAs): new high affinity oligonucleotides as potent primers for PCR and reverse transcription. Nucl. Acids Res., 37: e130; doi:10.1093/nar/gkp661.

[20] Nielsen, P., Pfundheller, H. M., Olsen, C. E. and Wengel, J., Synthesis of 2'-O,3'-C-Linked Bicyclic Nucleosides and Bicyclic Oligonucleotides, J. Chem. Soc., Perkin Trans. 1, 1997, 3423;

[21] Singh, S. K.; Nielsen, P.; Koshkin, A. A.; Wengel, J. LNA (Locked Nucleic Acids): Synthesis and High-Affinity Nucleic Acid Recognition. Chem. Commun. 1998, 455-456.

[22] Takusagawa, F. (1997) Selectivity of F8-actinomycin D for RNA:DNA hybrids and its anti-leukemia activity. Bioorg. Med. Chem. 5, 1197-1207.

[23] Shaw Nicholas N., Arya Dev P. Recognition of the unique structure of DNA:RNA hybrid; review Biochimie 90 (2008), 1026e1039

[24] Perales C, Cava F, Meijer W J, Berenguer J. Enhancement of DNA, cDNA synthesis and fidelity at high temperatures by a dimeric single-stranded DNA-binding protein. Nucleic Acids Res. 2003 Nov. 15; 31(22):6473-80.

[25] Shigemori Y, Mikawa T, Shibata T, Oishi M. Multiplex PCR: use of heat-stable *Thermus thermophilus* RecA protein to minimize non-specific PCR products. Nucleic Acids Res. 2005 Aug. 8; 33(14):e126.

[26] Boyer P L, Sarafianos S G, Arnold E, Hughes S H. Analysis of mutations at positions 115 and 116 in the dNTP binding site of HIV-1 reverse transcriptase. Proc Natl Acad Sci USA. 2000 Mar. 28; 97(7):3056-61.

[27] Fuentes G M, Rodríguez-Rodríguez L, Palaniappan C, Fay P J, Bambara R A. Strand displacement synthesis of the long terminal repeats by HIV reverse transcriptase. J Biol Chem. 1996 Jan. 26; 271(4):1966-71.

[28] Sambrook J.& Russell D., Molecular Cloning: A Laboratory Manual (Third Edition, book 1, chapter 7.20) U.S. Pat. No. 6,335,439: Method of preparing phosphoramidites

[29] Engler, M. J. and Richardson, C. C. (1982) DNA ligases. In The Enzymes, vol. X V (Boyer, P. D., ed.), pp. 3-29, Academic Press, New York

[30] Hsuih T C, Park Y N, Zaretsky C, Wu F, Tyagi S, Kramer F R, Sperling R, Zhang D Y. Novel, ligation-dependent PCR assay for detection of hepatitis C in serum. J Clin Microbiol. 1996 March; 34(3):501-7.

[31] Bullard D R, Bowater R P. Direct comparison of nick-joining activity of the nucleic acid ligases from bacteriophage T4. Biochem J. 2006 Aug. 15; 398(1):135-44.

[32] Zimmerman S B, Pheiffer B H. Macromolecular crowding allows blunt-end ligation by DNA ligases from rat liver or *Escherichia coli*. Proc Natl Acad Sci USA. 1983 October; 80(19):5852-6.

[33] Gerard G. F., and D'Alessio J. M., Chapter 6 (73-93) From: Methods in Molecular Biology, Vol. 16: Enzymes of Molecular Biology Edited by: M. M. Burell 1993 Humana Press Inc. Totowa, N.J.

[34] Pfaffl M W. A new mathematical model for relative quantification in real-time R T-PCR. Nucleic Acids Res. 2001 May 1; 29(9):e45.

U.S. Pat. No. 6,335,439. Alessandra Eleuteri et al. (2002): Method of preparing phosphoramidites US20030092905. Alexei Kochkine (2003): Synthesis of [2.2.1]bicyclo nucleosides U.S. Pat. No. 7,084,125. Jesper Wengel (2006): Xylo-LNA analogues U.S. Pat. No. 5,436,134. Richard P. Haugland et al. (1995): Cyclic-substituted unsymmetrical cyanine dyes.

U.S. Pat. No. 5,658,751 Stephen T. Yue et al. (1997): Substituted unsymmetrical cyanine dyes with selected permeability. Dye No. 211.

U.S. Pat. No. 6,569,627. Carl T. Wittwer (2003): Monitoring hybridization during PCR using SYBR™ Green I US2009/0227009 A1. Roy R. Sooknanan (2009): SELECTIVE TERMINAL TAGGING OF NUCLEIC ACIDS U.S. Pat. No. 4,683,195
U.S. Pat. No. 4,683,202
U.S. Pat. No. 4,800,159
U.S. Pat. No. 5,804,375
U.S. Pat. No. 5,322,770
U.S. Pat. No. 5,310,652
US 2002/0076767 A1
U.S. Pat. No. 6,391,592 B1
WO 94/17210 A1
WO 98/02449 A1
WO 99/61661
WO 02/086155
U.S. Pat. No. 5,849,497
WO 2009/019008

The invention claimed is:

1. A method for generating an amplified nucleic acid portion of a template nucleic acid, which is RNA, the method comprising:
   obtaining template RNA,
   annealing at least one oligonucleotide primer comprising a sequence tag to said template RNA, wherein said sequence tag does not anneal to said template RNA,
   annealing at least one further oligonucleotide primer to said template RNA downstream from the annealed at least one oligonucleotide primer, wherein (i) said further primer is hybridized to an oligonucleotide stopper that is annealed to said template RNA and said stopper is not capable of priming an elongation reaction on said template RNA or (ii) said further primer is hybridized to a further sequence tag that does not anneal to said template RNA,
   elongating the annealed at least one oligonucleotide primer in a template specific manner until the elongating product nucleic acid reaches the annealed oligonucleotide stopper or the annealed further oligonucleotide primer thereby stopping elongation, and simultaneously elongating said further oligonucleotide primer in a template specific manner, and
   ligating the elongated product nucleic acid to the 5' end of the reached oligonucleotide stopper or to the further sequence tag that is hybridized to said further primer.

2. The method according to claim 1, wherein a portion of one of said at least one oligonucleotide stopper is hybridized to a portion of said further oligonucleotide primer and another portion of said one of said at least one oligonucleotide stopper and another portion of said further oligonucleotide primer are annealed to said template RNA.

3. The method according to claim 1, wherein at least one, optionally all, oligonucleotide primer(s) is/are hybridized to an oligonucleotide stopper.

4. The method according to claim 1, further comprising:
   annealing to a same strand within a same RNA molecule as the at least one annealed oligonucleotide primer and the annealed oligonucleotide stopper and/or further oligonucleotide primer, additional oligonucleotide primers, and
   elongating annealed additional oligonucleotide primers until each elongating product nucleic acid reaches another annealed oligonucleotide primer or annealed oligonucleotide stopper thereby stopping elongation, wherein said additional oligonucleotide primers comprise 3 or more different oligonucleotide primers, optionally wherein said additional oligonucleotide primers are random primers.

5. The method according to claim 1, further comprising annealing an additional oligonucleotide stopper that is not capable of priming an elongation reaction on said template RNA, wherein said additional oligonucleotide stopper optionally comprises 2, 3, 4, 5, 6, 7, 8, 9, 10, 15, 20, 30, 40, 50, or more different oligonucleotide stoppers, and are optionally random stoppers.

6. The method according to claim 1, wherein said at least one oligonucleotide stopper comprises a sequence tag.

7. The method according to claim 6, further comprising amplifying the elongated products comprising the sequence tag of said at least one oligonucleotide primer or the sequence tag of said at least one oligonucleotide stopper, optionally by PCR using tag specific primers.

8. The method according to claim 1, wherein:
   said at least one oligonucleotide primer comprising the sequence tag comprises more than one oligonucleotide primer comprising a same sequence tag that is optionally a same sequence tag to all of said oligonucleotide primers, or
   said at least one oligonucleotide primer comprising the sequence tag comprises the sequence tag attached to the 5' end of said oligonucleotide primer.

9. The method according to claim 1, wherein any one of said oligonucleotide stoppers and any one of said oligonucleotide primers comprises a sequence tag each, and wherein the sequence tag of said oligonucleotide primers is at least partially complementary with the sequence of the sequence tag of said oligonucleotide stoppers thereby enabling hybridization of said oligonucleotide stoppers and said oligonucleotide primers with each other at least in a part of the respective sequence tag.

10. The method according to claim 1, wherein a nucleic acid with a reverse complement sequence to the sequence tag of said at least one oligonucleotide primer is added during the annealing of said first oligonucleotide primer or said at least one further oligonucleotide primer, or is added during said elongation reaction, or is already hybridized to the sequence tag of said at least one oligonucleotide primer prior to said annealing of said at least one oligonucleotide primer to said template RNA.

11. The method according to claim 10, further comprising providing modified nucleotides that increase melting temperature of complementary nucleic acid sequences compared to unmodified nucleotides, wherein the modified nucleotides are optionally selected from one or more of the group consisting of LNA nucleotides, 2' fluoronucleotides, and PNA nucleotides, wherein the modified nucleotides increase melting temperature between the sequence tag of the at least one oligonucleotide primer and the reverse complement.

12. The method according to claim 10, wherein the nucleic acid with the reverse complement sequence is covalently linked to the sequence tag of said at least one oligonucleotide primer, or the further sequence tag is covalently linked to said further primer, or the sequence tag of said at least one oligonucleotide primer is covalently linked to a stopper oligonucleotide with which the at least one oligonucleotide primer is hybridized, wherein the covalent link is optionally via a spacer or hairpin loop.

13. The method according to claim 1, characterized in that said oligonucleotide primers and/or oligonucleotide stoppers are phosphorylated or adenylated on the 5' end.

14. The method according to claim 1, characterized in that said template RNA is immobilized on a solid phase or solid support.

15. The method according to claim 1, further comprising a step of washing elongated product nucleic acids.

16. The method according to claim 15, wherein the washed elongated product nucleic acids are hybridized to a template nucleic acid or hybridized to a template nucleic acid immobilized on a solid phase or solid support.

17. The method according to claim 1, wherein elongation and ligation reactions are performed concurrently in one reaction step.

18. The method according to claim 1, wherein said method is performed by addition of a DNA polymerase and/or a ligase, optionally wherein said DNA polymerase and ligase are added in one reaction mixture with said template RNA.

19. The method according to claim 1, wherein a polymerase having nucleotide strand displacement activity is used for the elongation.

20. The method according to claim 1, wherein a nucleotide concentration during the elongation reaction is lower than the template concentration, optionally the molar ratio of nucleotide concentration to template concentration is in the range of 1:33 to 1:3.3.

21. The method according to claim 1, wherein actinomycin D is added to the elongation reaction in sufficient amounts to avoid second strand synthesis and to reduce strand displacement of a polymerase.

22. The method according to claim 1, wherein said template RNA is single stranded.

23. The method according to claim 1, wherein said obtained template RNA lacks a complementary strand over at least 30% of its length and/or lacks a complementary strand of at least 100 nucleotides in length.

24. A method of generating a sequence library of one or more template nucleic acids comprising amplifying one or more ligated elongated product nucleic acids produced from one or more template RNAs according to claim 1.

25. The method according to claim 1, wherein said at least one oligonucleotide primer and/or oligonucleotide stopper comprises at least one, optionally at least 2, optionally at least 3 modified nucleotides being selected from G or C, optionally at the 5' end of the oligonucleotide sequence.

26. The method according to claim 1, wherein the elongated product nucleic acid is ligated to the sequence tag that is hybridized to said further primer.

27. A method for generating a sequence library of one or more template nucleic acids comprising conducting the method of claim 1, with a plurality of different oligonucleotide primers and further primers.

28. The method according to claim 1, wherein said at least one oligonucleotide primer and/or at least one oligonucleotide stopper comprises a nucleotide modification increasing the Tm or stiffening the sugar phosphate backbone of oligonucleotides, optionally selected from 2'fluoro nucleosides, LNAs, ZNAs, PNAs.

29. The method according to claim 28, wherein said at least one oligonucleotide primer and/or at least one oligonucleotide stopper comprises at least one, optionally at least 2, optionally at least 3 modified nucleotides being selected from G or C, optionally at the 5' end of the oligonucleotide sequence.

30. The method according to claim 1, further comprising providing modified nucleotides that increase melting temperature of complementary nucleic acid sequences compared to unmodified nucleotides, wherein the modified nucleotides are optionally selected from one or more of the group consisting of LNA nucleotides, 2' fluoronucleotides, and PNA nucleotides, wherein the modified nucleotides increase melting temperature between the further sequence tag and the further primer.

31. The method according to claim 1, wherein the at least one oligonucleotide primer is further hybridized to an oligonucleotide stopper, further comprising providing modified nucleotides that increase melting temperature of complementary nucleic acid sequences compared to unmodified nucleotides, wherein the modified nucleotides are optionally selected from one or more of the group consisting of LNA nucleotides, 2' fluoronucleotides, and PNA nucleotides, wherein the modified nucleotides increase melting temperature between the sequence tag of the at least one oligonucleotide primer and the stopper.

32. The method according to claim 1, wherein said at least one oligonucleotide primer and/or at least one oligonucleotide stopper comprises intercalators or additives that specifically bind to nucleic acids to increase the Tm.

* * * * *